United States Patent
Takahashi et al.

(10) Patent No.: US 12,265,329 B2
(45) Date of Patent: Apr. 1, 2025

(54) ACTINIC RAY-SENSITIVE OR RADIATION-SENSITIVE RESIN COMPOSITION, ACTINIC RAY-SENSITIVE OR RADIATION-SENSITIVE FILM, PATTERN FORMING METHOD, AND METHOD FOR MANUFACTURING ELECTRONIC DEVICE

(71) Applicant: FUJIFILM Corporation, Tokyo (JP)

(72) Inventors: Kotaro Takahashi, Haibara-gun (JP); Yasunori Yonekuta, Haibara-gun (JP); Taro Miyoshi, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 457 days.

(21) Appl. No.: 17/393,889

(22) Filed: Aug. 4, 2021

(65) Prior Publication Data

US 2021/0373438 A1 Dec. 2, 2021

Related U.S. Application Data

(63) Continuation of application No. PCT/JP2020/008780, filed on Mar. 3, 2020.

(30) Foreign Application Priority Data

Mar. 28, 2019 (JP) ................................. 2019-063688

(51) Int. Cl.
| | | |
|---|---|---|
| G03F 7/004 | (2006.01) | |
| C07D 235/18 | (2006.01) | |
| C07D 263/57 | (2006.01) | |
| C07D 277/66 | (2006.01) | |
| C08F 212/14 | (2006.01) | |

(52) U.S. Cl.
CPC ......... *G03F 7/0045* (2013.01); *C07D 235/18* (2013.01); *C07D 263/57* (2013.01); *C07D 277/66* (2013.01); *C08F 212/24* (2020.02)

(58) Field of Classification Search
None
See application file for complete search history.

(56) References Cited

U.S. PATENT DOCUMENTS

| | | | | |
|---|---|---|---|---|
| 7,276,324 B2 * | 10/2007 | Watanabe | ............ | G03F 7/0382 430/326 |
| 7,629,108 B2 * | 12/2009 | Watanabe | ............ | C07D 233/60 546/1 |
| 10,942,455 B2 | 3/2021 | Kamimura | | |
| 2004/0234884 A1 * | 11/2004 | Watanabe | ............ | G03F 7/0382 430/141 |
| 2011/0269071 A1 * | 11/2011 | Fujimori | ............... | G03F 7/0045 430/325 |
| 2015/0004533 A1 | 1/2015 | Hirano et al. | | |
| 2018/0040474 A1 | 2/2018 | Zi et al. | | |

FOREIGN PATENT DOCUMENTS

| | | |
|---|---|---|
| JP | 2007-240631 A | 9/2007 |
| JP | 2011-232657 A | 11/2011 |
| JP | 2013-228681 A | 11/2013 |
| JP | 2015-075551 A | 4/2015 |
| TW | 200839437 A | 10/2008 |
| TW | 201819585 A | 6/2018 |

OTHER PUBLICATIONS

Communication issued on Jun. 16, 2023 by the Taiwan Intellectual Property Office for Taiwanese Patent Application No. 109107033.
International Preliminary Report on Patentability dated Sep. 28, 2021 in International Application No. PCT/JP2020/008780.
Written Opinion of the International Searching Authority dated Apr. 7, 2020 in International Application No. PCT/JP2020/008780.
International Search Report dated Apr. 7, 2020 in International Application No. PCT/JP2020/008780.
KR Communication issued Aug. 8, 2023 from the Korean Patent Office in KR Application No. 10-2021-7026844.

* cited by examiner

*Primary Examiner* — Sean M DeGuire
*Assistant Examiner* — Andrew Preston Traywick
(74) *Attorney, Agent, or Firm* — Sughrue Mion, PLLC

(57) ABSTRACT

An actinic ray-sensitive or radiation-sensitive resin composition includes a resin having a solubility in a developer, which changes by the action of an acid, a compound that generates an acid upon irradiation with actinic rays or radiation; and an acid diffusion control agent, in which a molecular weight of the acid diffusion control agent is 420 or more, and a distance Ra between a Hansen solubility parameter of the acid diffusion control agent and a Hansen solubility parameter of the air satisfies $15 \leq Ra \leq 45$.

5 Claims, No Drawings

ACTINIC RAY-SENSITIVE OR RADIATION-SENSITIVE RESIN COMPOSITION, ACTINIC RAY-SENSITIVE OR RADIATION-SENSITIVE FILM, PATTERN FORMING METHOD, AND METHOD FOR MANUFACTURING ELECTRONIC DEVICE

CROSS-REFERENCE TO RELATED APPLICATIONS

This application is a Continuation of PCT International Application No. PCT/JP2020/008780 filed on Mar. 3, 2020, which claims priority under 35 U.S.C § 119(a) to Japanese Patent Application No. 2019-063688 filed on Mar. 28, 2019. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition, an actinic ray-sensitive or radiation-sensitive film, a pattern forming method, and a method for manufacturing an electronic device.

2. Description of the Related Art

In processes for manufacturing semiconductor devices such as an integrated circuit (IC) and a large scale integration circuit (LSI), microfabrication by lithography using a photoresist composition has been performed in the related art. In recent years, along with the high integration of integrated circuits, the formation of ultrafine patterns in a submicron region or quarter micron region has been required. In accordance with this, a tendency that an exposure wavelength becomes shorter, for example, from a g-ray to an i-ray, and further to KrF excimer laser light or ArF excimer laser light, can be seen, and development of lithography using electron beams (EB), X-rays, extreme ultraviolet rays (EUV), and the like in addition to the excimer laser light, is also now in progress. Along with this, chemically amplified resist compositions that are effectively sensitive to various actinic rays and radiations have been developed.

Various compounds have also been found for an acid diffusion control agent that is one of main components of a chemically amplified resist composition, and for example, JP2007-240631A and JP2011-232657A describe a chemically amplified resist composition that contains a basic compound (acid diffusion control agent) having a benzimidazole skeleton.

SUMMARY OF THE INVENTION

However, along with a demand for formation of fine patterns in recent years, there has been a desire for further improvement in a pattern resolution. In addition, in a case where exposure is performed at a high vacuum degree, it is desired to prevent device contamination by a compound included in a resist composition.

An object of the present invention is to provide an actinic ray-sensitive or radiation-sensitive resin composition which has a high resolution and is capable of preventing device contamination; and an actinic ray-sensitive or radiation-sensitive film, a pattern forming method, and a method for manufacturing an electronic device, each using the actinic ray-sensitive or radiation-sensitive resin composition.

As a result of intensive examinations, the present inventors have found that it is possible to suppress a pattern collapse by using an acid diffusion control agent having a controlled affinity for air in an actinic ray-sensitive or radiation-sensitive resin composition, thereby obtaining a good resolution.

That is, the present inventors have found that the object can be accomplished by the following configurations.

<1> An actinic ray-sensitive or radiation-sensitive resin composition comprising:
a resin having a solubility in a developer, which changes by an action of an acid;
a compound that generates an acid upon irradiation with actinic rays or radiation; and
an acid diffusion control agent,
in which a molecular weight of the acid diffusion control agent is 420 or more, and
a distance Ra between a Hansen solubility parameter of the acid diffusion control agent and a Hansen solubility parameter of air is from 15 $MPa^{0.5}$ to 45 $MPa^{0.5}$.

<2> The actinic ray-sensitive or radiation-sensitive resin composition as described in <1>,
in which the acid diffusion control agent is a compound, represented by General Formula (Q-1).

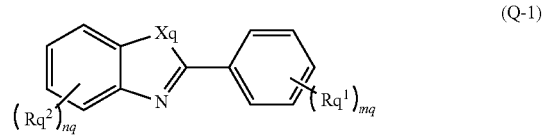

In General Formula (Q-1),
$Rq^1$ and $Rq^2$ each independently represent a substituent. Xq represents $-NR^N-$, $-S-$, or $-O-$. $R^N$ represents a hydrogen atom or a monovalent organic group.
mq represents an integer of 0 to 5, In a case where mq is 2 or more, a plurality of $Rq^1$'s may be the same as or different from each other. In addition, in a case where mq is 2 or more, the plurality of $Rq^1$'s may be bonded to each other to form a ring structure.
nq represents an integer of 0 to 4. In a case where nq is 2 or more, a plurality of $Rq^2$'s may be the same as or different from each other. In addition, in a case where nq is 2 or more, the plurality of $Rq^2$'s may be bonded to each other to form a ring structure.

<3> The actinic ray-sensitive or radiation-sensitive resin composition as described in <2>,
in which Xq in General Formula (Q-1) is $-NH-$.

<4> The actinic ray-sensitive or radiation-sensitive resin composition as described in <2> or <3>,
in which the compound represented by General Formula (Q-1) is a compound represented by General Formula (Q-11).

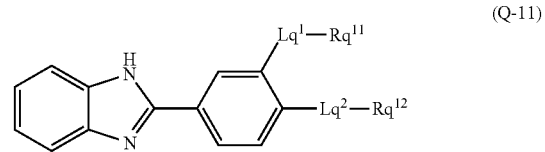

In General Formula (Q-11),
Rq$^{11}$ to Rq$^{12}$ each independently represent an alkyl group or an aryl group.
Lq$^1$ and Lq$^2$ each independently represent a single bond, or —O—, —(C=O)—, an alkylene group, or a divalent linking group formed by combination of these groups.
<5> The actinic ray-sensitive or radiation-sensitive resin composition as described in any one of <1> to <4>,
in which Ra is from 17 MPa$^{0.5}$ to 42 MPa$^{0.5}$.
<6> An actinic ray-sensitive or radiation-sensitive film formed of the actinic ray-sensitive or radiation-sensitive resin composition as described in any one of <1> to <5>.
<7> A pattern forming method comprising:
a resist film forming step of forming a resist film using the actinic ray-sensitive or radiation-sensitive resin composition as described in any one of <1> to <5>;
an exposing step of exposing the resist film; and
a developing step of developing the exposed resist film using a developer.
<8> A method for manufacturing an electronic device, comprising the pattern forming method as described in <7>.

According to the present invention, it is possible to provide an actinic ray-sensitive or radiation-sensitive resin composition which has a high resolution and is capable of preventing device contamination; and an actinic ray-sensitive or radiation-sensitive film, a pattern forming method, and a method, for manufacturing an electronic device, each using the actinic ray-sensitive or radiation-sensitive resin composition.

DESCRIPTION OF THE PREFERRED EMBODIMENTS

Hereinafter, the present invention will be described, in detail.

Description of configuration requirements described below may be made on the basis of representative embodiments of the present invention in some cases, but the present invention is not limited to such embodiments.

"Actinic rays" or "radiation" in the present specification means, for example, a bright line spectrum of a mercury lamp, tar ultraviolet rays typified by an excimer laser, extreme ultraviolet rays (EUV), X-rays, soft X-rays, electron beams (EB), or the like. "Light" in the present specification means actinic rays or radiation. Unless otherwise specified, "exposure" in the present specification encompasses not only exposure by a bright line spectrum of a mercury lamp, far ultraviolet rays typified by an excimer laser, extreme ultraviolet rays (EUV), X-rays, or the like, but also lithography by particle rays such as electron beams and ion beams.

In the present specification, a numerical range expressed using "to" is used in a meaning of a range that includes the preceding and succeeding numerical values of "to" as the tower limit value and the upper limit value, respectively.

In the present specification, (meth)acrylate represents at least one of acrylate or methacrylate. In addition, (meth) acrylic acid represents at least one of acrylic acid or methacrylic acid.

In the present specification, the weight-average molecular weight (Mw), the number-average molecular weight (Mn), and the dispersity (also referred to as a molecular weight distribution) (Mw/Mn) of a resin are each defined as a value expressed in terms of polystyrene by means of gel permeation chromatography (GPC) measurement (solvent: tetrahydrofuran, flow amount (amount of a sample injected): 10 µL, columns: TSK gel Multipore HXL-M manufactured by Tosoh Corporation, column temperature: 40° C., flow rate: 1.0 mL/min, detector: differential refractive index detector) using a GPC apparatus (HLC-8120 GPC manufactured by Tosoh Corporation).

In notations for a group (atomic group) in the present specification, in a case where the group is cited without specifying that it is substituted, or unsubstituted, the group includes both a group having no substituent and a group having a substituent. For example, an "alkyl group" includes not only an alkyl group having no substituent (unsubstituted alkyl group), but also an alkyl group having a substituent (substituted alkyl group). In addition, an "organic group" in the present specification refers to a group including at least one carbon atom.

Furthermore, in the present specification, the types of substituents, the positions of substituents, and the number of substituents in a case where it is described that "a substituent may be contained" are not particularly limited. The number of the substituents may be, for example, one, two, three, or more. Examples of the substituent include a monovalent non-metal atomic group from winch a hydrogen atom has been excluded, and the substituent can be selected from the following substituent T, for example.
(Substituent T)

Examples of the substituent T include halogen atoms such as a fluorine atom, a chlorine atom, a bromine atom, and an iodine atom; alkoxy groups such as a methoxy group, an ethoxy group, and a tert-butoxy group; aryloxy groups such as a phenoxy group and a p-tolyloxy group; alkoxycarbonyl groups such as a methoxycarbonyl group, a butoxycarbonyl group, and a phenoxycarbonyl group; acyloxy groups such as an acetoxy group, a propionyloxy group, and a benzoyloxy group; acyl groups such as an acetyl group, a benzoyl group, an isobutyryl group, an acryloyl group, a methacryloyl group, and a methoxalyl group; alkylsulfanyl groups such as a methylsulfanyl group and a tert-butylsulfanyl group; arylsulfanyl groups such as a phenylsulfanyl group and a p-tolylsulfanyl group; an alkyl group; a cycloalkyl group; an aryl group; a heteroaryl group; a hydroxyl group; a carboxyl group; a formyl group; a sulfo group; a cyano group; an alkylaminocarbonyl group; an arylaminocarbonyl group; a sulfonamide group; a silyl group; an amino group; a monoalkylamino group; a dialkylamino group; an arylamino group; and a combination thereof.

[Actinic Ray-Sensitive or Radiation-Sensitive Resin Composition]

The actinic ray-sensitive or radiation-sensitive resin composition to the present invention (hereinafter also referred to as the "composition of an embodiment of the present invention") is an actinic ray-sensitive or radiation-sensitive resin composition including a resin having a solubility in a developer, which changes by the action of an acid, a compound that generates an acid upon irradiation with actinic rays or radiation, and an acid diffusion control agent, in which a molecular weight of the acid diffusion control agent is 420 or more, and a distance Ra between a Hansen solubility parameter of the acid diffusion control agent and a Hansen solubility parameter of air is from 15 MPa$^{0.5}$ to 45 MPa$^{0.5}$.

The composition of the embodiment of the present invention is preferably a resist composition, and may be either a positive tone resist composition or a negative tone resist composition. In addition, the resist composition may be either a resist composition for alkali development or a resist composition for organic solvent development. Among those, the positive tone resist composition is preferable, and a resist composition for alkali development is also preferable.

Furthermore, the composition of the embodiment of the present invention is preferably a chemically amplified resist composition, and more preferably a chemically amplified positive tone resist composition.

<Acid Diffusion Control Agent>

The acid diffusion control agent used in the present invention has a molecular weight of 420 or more, and a distance Ra between a Hansen solubility parameter ($HSP_1$) of the acid diffusion control agent and a Hansen solubility parameter ($HSP_2$) of air (simply also referred, to as "Ra") is from 15 $MPa^{0.5}$ to 45 $MPa^{0.5}$.

(Distance Ra Between Hansen Solubility Parameters)

The Hansen solubility parameter (HSP) is formed of three components: a dispersion force term δd, a dipole-dipole force term δp, and a hydrogen bond force term δh, In the present invention, the Hansen solubility parameter ($HSP_1$) of the acid diffusion control agent (that is, each value of $δd_1$, $δp_1$, and $δh_1$) is calculated by a Y-MB method using HSPiP (4th edition 4.1.07), which is software for computation of an HSP value from a chemical structural formula of a compound.

In addition, the Hansen solubility parameter ($HSP_2$) of air (that is, each value of $δd_2$, $δp_2$, and $δh_2$) is calculated by weighted-averaging HSP's of nitrogen and oxygen described in an HSPiP manual (ver. 4 e-Book Chapter 19).

The distance Ra between $HSP_1$ and $HSP_2$ is calculated by Expression (1).

$$Ra=\{4(δd_1-δd_2)^2+(δp_1-δp_2)^2+(δh_1-δh_2)^2\}^{0.5} \quad (1)$$

It should be noted that $δd_1$ represents a dispersion force term δd of the acid diffusion control agent.

$δd_2$ represents a dispersion force term δd of air.

$δp_1$ represents a dipole-dipole force term δp of the acid diffusion control agent.

$δp_2$ represents a dipole-dipole force term δp of air.

$δh_1$ represents a hydrogen bond, force term δh of the acid diffusion control agent.

$δh_2$ represents a hydrogen bond force term δh of air.

As a result of intensive examinations, the present inventors have found that by using an acid diffusion control agent that has a distance Ra between the Hansen solubility parameter ($HSP_1$) of the acid diffusion control agent and a Hansen solubility parameter ($HSP_2$) of air is from 15 $MPa^{0.5}$ to 45 $MPa^{0.5}$, for example, a pattern collapse in a line-and-space pattern (LS pattern) can be suppressed, and as a result, a good resolution can be obtained.

Details of the mechanism that makes it possible to suppress the pattern collapse have not been clarified, but are presumed to be as follows by the present inventors.

In a case where an upper part of the pattern has an overhanging shape in the cross-sectional shape of the pattern, the collapse easily occurs. Accordingly, the present inventors have contemplate to manufacture a pattern having a rectangular or round-shaped cross-sectional shape with a slightly rounded upper part in order to suppress the collapse. Furthermore, in general, although it is considered that the cross-sectional shape of an LS pattern is preferably rectangular, but from the viewpoint of preventing the LS pattern from collapsing, it is considered that a round-shaped cross-section with a slightly rounded upper part is also preferable.

By setting Ra to 15 $MPa^{0.5}$ or more and lowering the affinity between the acid diffusion control agent and the air, an amount of acid diffusion control agent present on the air interface side of a film can be reduced in a case where the composition of the embodiment of the present invention is applied onto a substrate in the atmosphere to form the film. Therefore, in a case where the composition of the embodiment of the present invention is a positive tone resist composition, acid quenching occurs by the acid diffusion control agent in the lower part of the film (substrate side) but the quenching is less likely to occur in the upper part of the film (air interface side) in a case where an acid generated in the exposed area diffuses to the unexposed area in the exposing and developing steps. As a result, the cross-sectional shape of the LS pattern obtained by development is a rectangular or round cross-sectional shape with a slightly rounded upper part, and a pattern collapse can be suppressed.

In addition, by setting Ra to 45 $MPa^{0.5}$ or less, the solubility of the acid diffusion control agent in the solvent can be ensured and the coating properties are improved.

Ra is preferably from 17 $MPa^{0.5}$ to 42 $MPa^{0.5}$.

(Molecular Weight)

The molecular weight of the acid diffusion control agent used in the present invention is 420 or more. By setting the molecular weight to 420 or more, the acid diffusion control agent is less likely to volatilize even in a case where exposure is performed at a high vacuum degree such as electron beam (EB) exposure and extreme ultraviolet ray (EUV) exposure, for example, and it is thus possible to prevent device from contamination. In a case where the molecular weight is less than 420, for example, a difference in the prebaking (PB) temperature and time, and a difference in the post exposure baking (PEB) temperature cause a difference in the volatilization amount, and thus, it is susceptible to a process such as a change in the sensitivity.

The molecular weight of the acid diffusion control agent is preferably from 420 to 800, and more preferably from 450 to 600.

(Compound Represented by General Formula (Q-1))

The acid diffusion control agent in the present invention is preferably a compound represented by General Formula (Q-1).

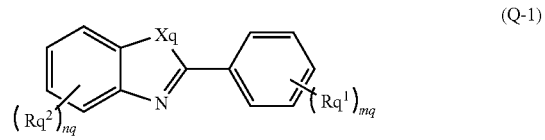

In General Formula (Q-1), $Rq^1$ and $Rq^2$ each independently represent a substituent.

Xq represents —$NR^N$—, —S—, or —O—. $R^N$ represents a hydrogen atom or a monovalent organic group.

mq represents an integer of 0 to 5. In a case where mq is 2 or more, a plurality of $Rq^1$'s may be the same as or different from each other. In addition, in a case where mq is 2 or more, the plurality of $Rq^1$'s may be bonded to each other to form a ring structure.

nq represents an integer of 0 to 4. In a case where nq is 2 or more, a plurality of $Rq^2$'s may be the same as or different from each other. In addition, in a case where nq is 2 or more, the plurality of $Rq^2$'s may be bonded, to each other to form a ring structure.

In General Formula (Q-1), $Rq^1$ and $Rq^2$ each independently represent a substituent.

The total number of carbon atoms in the substituents represented by $Rq^1$ and $Rq^2$ is not particularly limited, but is preferably 1 to 20, more preferably 3 to 15, and still more preferably 5 to 10.

$Rq^1$ and $Rq^2$ are not particularly limited, but are each preferably a monovalent organic group. The monovalent organic group is not particularly limited, but examples thereof include an alkyl group (which may be linear or branched, and preferably has 1 to 20 carbon atoms, more preferably has 3 to 15 carbon atoms, and still more preferably has 5 to 10 carbon atoms), an alkoxy group (which may be linear or branched, and preferably has 1 to 20 carbon atoms, more preferably has 3 to 15 carbon atoms, and still more preferably has 5 to 10 carbon atoms), an alkylcarbonyl group (which may be linear or branched, and preferably has 2 to 20 carbon atoms, more preferably has 4 to 15 carbon atoms, and still more preferably has 6 to 10 carbon atoms), an alkylcarbonyloxy group (which may be linear or branched, and preferably has 2 to 20 carbon atoms, more preferably has 4 to 15 carbon atoms, and still more preferably has 6 to 10 carbon atoms), an alkyloxycarbonyl group (which may be linear or branched, and preferably has 2 to 20 carbon atoms, more preferably has 4 to 15 carbon atoms, and still more preferably has 6 to 10 carbon atoms), an aryl group (which preferably has 6 to 20 carbon atoms, more preferably has 6 to 15 carbon atoms, and still more preferably has 6 to 10 carbon atoms), an aryloxy group (which preferably has 6 to 20 carbon atoms, more preferably has 6 to 15 carbon atoms, and still more preferably has 6 to 10 carbon atoms), an arylcarbonyl group (which preferably has 7 to 20 carbon atoms, more preferably has 7 to 15 carbon atoms, and still more preferably has 7 to 10 carbon atoms), an arylcarbonyloxy group (which preferably has 7 to 20 carbon atoms, more preferably has 7 to 15 carbon atoms, and still more preferably has 7 to 10 carbon atoms), an aryloxycarbonyl group (which preferably has 7 to 20 carbon atoms, more preferably has 7 to 15 carbon atoms, and still more preferably has 7 to 10 carbon atoms), a cycloalkyl group (which preferably has 3 to 20 carbon atoms, more preferably has 4 to 15 carbon atoms, and still more preferably has 5 to 10 carbon atoms), a cycloalkyloxy group (which preferably has 3 to 20 carbon atoms, more preferably has 4 to 15 carbon atoms, and still more preferably has 5 to 10 carbon atoms), a cycloalkylcarbonyl group (which preferably has 4 to 20 carbon atoms, more preferably has 5 to 15 carbon atoms, and still more preferably has 6 to 10 carbon atoms), a cycloalkyloxycarbonyl group (which preferably has 4 to 20 carbon atoms, more preferably has 5 to 15 carbon atoms, and still more preferably has 6 to 10 carbon atoms), or a group formed by combination of these groups. These monovalent organic groups may have a substituent, and examples of the substituent include the substituents T, preferably a hydroxyl group, an alkyl group, an alkoxycarbonyl group, or a group formed by combination of these groups.

In General Formula (Q-1), Xq represents $-NR^N-$, $-S-$, or $-O-$, $R^N$ represents a hydrogen atom or a monovalent organic group.

In a case where $R^N$ represents the monovalent organic group, examples of the monovalent organic group include an alkyl group (preferably an alkyl group having 1 to 10 carbon atoms), a cycloalkyl group (preferably a cycloalkyl group having 3 to 20 carbon atoms), and an aryl group (preferably an aryl group having 6 to 20 carbon atoms). $R^N$ is preferably the hydrogen atom.

Xq is preferably $-NR^N-$, and more preferably $-NH-$.

In General Formula (Q-1), mq represents an integer of 0 to 5, In a case where mq is 2 or more, a plurality of $Rq^1$'s may be the same as or different from each other.

mq is preferably 2 or 3, and more preferably 2.

In General Formula (Q-1), nq represents an integer of 0 to 4, In a case where nq is 2 or more, a plurality of $Rq^2$'s may be the same as or different from each other.

nq is preferably 0 to 2, and more preferably 0.

The compound represented by General Formula (Q-1) is preferably the compound of General Formula (Q-1) in which Xq is $-NH-$, and more preferably a compound represented by General Formula (Q-11).

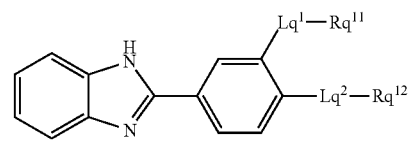

(Q-11)

In General Formula (Q-11), $Rq^{11}$ to $Rq^{12}$ each independently represent an alkyl group or an aryl group.

$Lq^1$ and $Lq^2$ each independently represent a single bond, or $-O-$, $-(C=O)-$, an alkylene group, or a divalent linking group formed by combination of these groups.

In General Formula (Q-11), $Rq^{11}$ to $Rq^{12}$ each independently represent an alkyl group or an aryl group.

In a case where $Rq^{11}$ to $Rq^{12}$ each represent the alkyl group, the alkyl group is preferably an alkyl group having 1 to 20 carbon atoms, more preferably an alkyl group having 3 to 15 carbon atoms, and still more preferably an alkyl group having 5 to 10 carbon atoms. The alkyl group may have a substituent.

In the case where $Rq^{11}$ to $Rq^{12}$ each represent the aryl group, the aryl group is preferably an aryl group having 6 to 20 carbon atoms, more preferably an aryl group having 6 to 15 carbon atoms, and still more preferably an aryl group having 6 to 10 carbon atoms. The aryl group may have a substituent.

In General Formula (Q-11), $Lq^1$ and $Lq^2$ each independently represent a single bond, or $-O-$, $-(C=O)-$, an alkylene group, or a divalent linking group formed by combination of these groups.

$Lq^1$ and $Lq^2$ are each independently preferably $-O-$, $-O(C=O)-$*, or $-(C=O)O-$*, more preferably $-O-$ or $-O(C=O)-$*, and still more preferably $-O-$. Here, * represents a bonding site with $Rq^{11}$ or $Rq^{12}$ in General Formula (Q-11).

Specific examples of the compound represented by General Formula (Q-1) are shown below, but the present invention is not limited thereto. Furthermore, in the following structural formulae, "n" described before the alkyl group indicates that the alkyl group is a linear alkyl group.

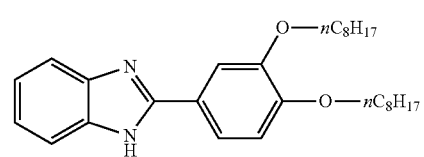

(q-1)

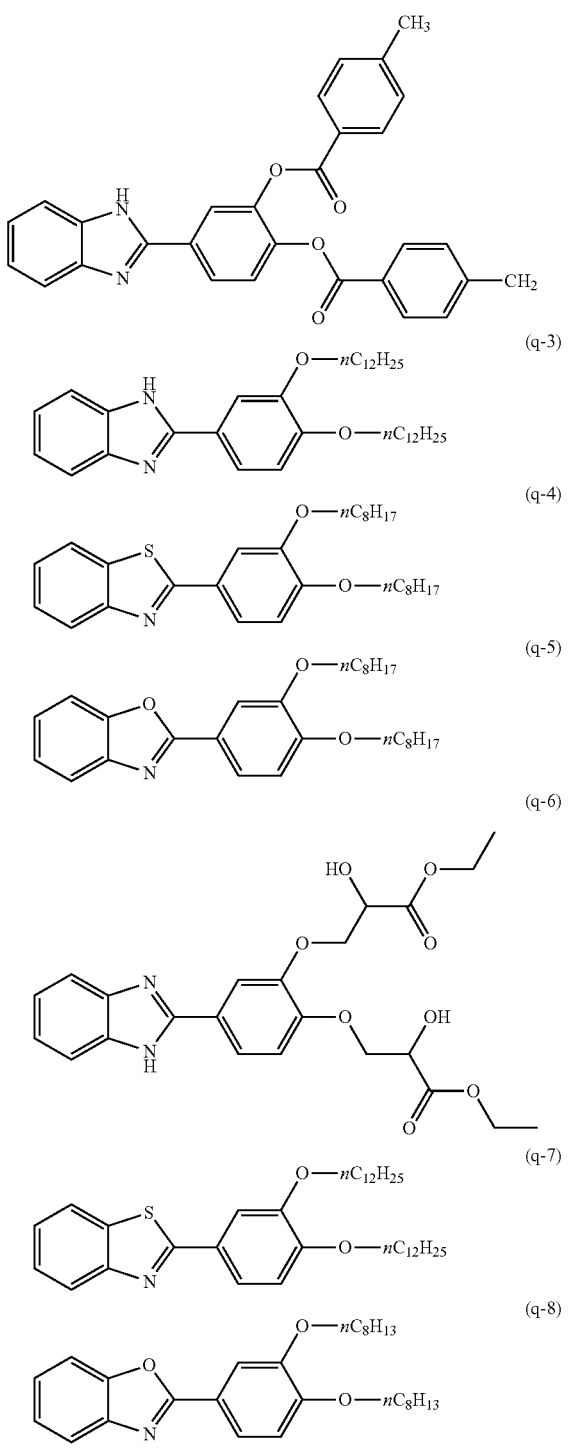

In the composition of the embodiment of the present invention, the acid diffusion control agents may be used alone or in combination of two or more kinds thereof.

The content of the acid diffusion control agent (in a case where a plurality of kinds of the acid diffusion control agents are present, a total content thereof) in the composition of the embodiment of the present invention is preferably 0.001% to 20% by mass, and more preferably 0.01% to 10% by mass with respect to the total solid content of the composition of the embodiment of the present invention.

In addition, the total solid content of the composition of the embodiment of the present invention means other components (components that can constitute an actinic ray-sensitive or radiation-sensitive film) excluding the solvent.

<Resin Having Solubility in Developer, Which Changes by Action of Acid>

The actinic ray-sensitive or radiation-sensitive resin composition of the embodiment of the present invention contains a resin having a solubility in a developer, which changes by the action of an acid.

The resin having a solubility in a developer, which changes by the action of an acid may be either a resin having a solubility in a developer, which is increased by the action of an acid or a resin having a solubility in a developer, which is decreased by the action of an acid.

Examples of the resin having a solubility in a developer, which changes by the action of an acid include a resin having a group (hereinafter also referred to as an "acid-decomposable group") having a polarity which is increased upon decomposition by the action of an acid (hereinafter also referred to as an "acid-decomposable resin" or a "resin (A)"), or a resin having a structure which changes by the action of an acid to decrease the solubility in a developer (for example, a resin having a structure which changes by a crosslinking reaction with a crosslinking agent by the action of an acid and a resin having a structure which changes by a crosslinking reaction between resins having crosslinkable groups).

In a case where the resin having a solubility in a developer, which changes by the action of an acid is the resin (A), in the pattern forming method of an embodiment of the present invention, typically, a positive tone pattern is suitably formed in a case where an alkali developer is adopted, as the developer, and a negative tone pattern is suitably formed in a case where an organic developer is adopted as the developer.

In a case where the resin having a solubility in a developer, which changes by the action of an acid is a resin having a structure which changes by the action of an acid to decrease the solubility in a developer, in the pattern forming method of the embodiment of the present invention, typically, a negative tone pattern is suitably formed in a case where an alkali developer is adopted as the developer, and the negative tone pattern is also suitably formed in a case where an organic developer is adopted, as the developer.

Hereinbelow, the resin (A) which is a preferred embodiment will be described below.

The resin (A) preferably has a repeating unit having an acid-decomposable group.

As the resin (A), a known resin can be appropriately used. For example, the known resins disclosed in paragraphs <0055> to <0191> of the specification of US2016/0274458A1, paragraphs <0035> to <0085> of the specification of US2015/0004544A1, and paragraphs <0045> to <0090> of the specification of US2016/0147150A1 can be suitably used as the resin (A).

The acid-decomposable group preferably has a structure in which a polar group is protected with a group that is eliminated through decomposition by the action of an acid (eliminable group).

Examples of the polar group include an acidic group (typically a group which dissociates in a 2.38%-by-mass aqueous tetramethylammonium hydroxide solution), such as a carboxyl group, a phenolic hydroxyl group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, and a tris(alkylsulfonyl)methylene group, and an alcoholic hydroxyl group.

Moreover, the alcoholic hydroxyl group refers to a hydroxyl group bonded to a hydrocarbon group, which is a hydroxyl group other than a hydroxyl group (phenolic hydroxyl group) directly bonded to an aromatic ring, from which an aliphatic alcohol group (for example, a hexafluoroisopropanol group) having the α-position substituted with an electron-withdrawing group such as a fluorine atom is excluded as a hydroxyl group. The alcoholic hydroxyl group is preferably a hydroxyl group having an acid dissociation constant (pKa) from 12 to 20.

Among those, as the polar group, the carboxyl group, the phenolic hydroxyl group, the fluorinated alcohol group (preferably the hexafluoroisopropanol group), or the sulfonic acid group is preferable.

Examples of the group that is eliminated through decomposition by the action of an acid (eliminable group) include groups represented by Formulae (Y1) to (Y4).

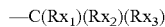   Formula (Y1):

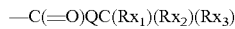   Formula (Y2):

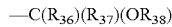   Formula (Y3):

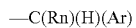   Formula (Y4):

In Formula (Y1) and Formula (Y2), $Rx_1$ to $Rx_3$ each independently represent an (linear or branched) alkyl group or a (monocyclic or polycyclic) cycloalkyl group. Furthermore, in a case where all of $Rx_1$ to $Rx_3$ are (linear or branched) alkyl groups, it is preferable that at least two of $Rx_1$, $Rx_2$, or $Rx_3$ are methyl groups.

Among those, it is preferable that $Rx_1$ to $Rx_3$ each independently represent a linear or branched alkyl group, and it is more preferable that $Rx_1$ to $Rx_3$ each independently represent a linear alkyl group.

Two of $Rx_1$ to $Rx_3$ may be bonded to each other to form a monocycle or a polycycle.

As the alkyl group of each of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the cycloalkyl group formed by the bonding of two of $Rx_1$ to $Rx_3$, a monocyclic cycloalkyl group such as a cyclopentyl group and a cyclohexyl group, and a polycyclic cycloalkyl group such as a norbornyl group, a tetracyclodecanyl group, a tetracyclododecanyl group, and an adamantyl group are preferable, and a monocyclic cycloalkyl group having 5 or 6 carbon atoms is more preferable.

In the cycloalkyl group formed by the bonding of two of $Rx_1$ to $Rx_3$, for example, one of the methylene groups constituting the ring may be substituted with a heteroatom such as an oxygen atom or a group having a heteroatom, such as a carbonyl group.

With regard to the group represented by Formula (Y1) or Formula (Y2), for example, an aspect in which $Rx_1$ is a methyl group or an ethyl group, and $Rx_2$ and $Rx_3$ are bonded to each other to form a cycloalkyl group is preferable.

In Formula (Y3), $R_{36}$ to $R_{38}$ each independently represent a hydrogen atom or a monovalent organic group. $R_{37}$ and $R_{38}$ may be bonded to each other to form a ring. Examples of the monovalent organic group include an alkyl group, a cycloalkyl group, an aryl group, an aralkyl group, and an alkenyl group. It is also preferable that $R_{36}$ is the hydrogen atom.

As Formula (Y3), a group represented by Formula (Y3-1) is preferable.

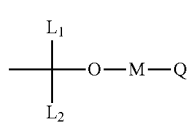

Here, $L_1$ and $L_2$ each independently represent a hydrogen atom, an alkyl group, a cycloalkyl group, an aryl group, or a group formed by combination thereof (for example, a group formed by a combination of an alkyl group and an aryl group).

M represents a single bond or a divalent linking group.

Q represents an alkyl group which may include a heteroatom, a cycloalkyl group which may include a heteroatom, an aryl group which may Include a heteroatom, an amino group, an ammonium group, a mercapto group, a cyano group, an aldehyde group, or a group formed by combination thereof (for example, a group formed by a combination of an alkyl group and a cycloalkyl group).

In the alkyl group and the cycloalkyl group, for example, one of the methylene groups may be substituted with a heteroatom such as an oxygen atom or a group having a heteroatom, such as a carbonyl group.

In addition, it is preferable that one of $L_1$ or $L_2$ is a hydrogen atom, and the other is an alkyl group, a cycloalkyl group, an aryl group, or a group formed by a combination of an alkylene group and an aryl group.

At least two of Q, M, or $L_1$ may be bonded to each other to form a ring (preferably a 5-membered or 6-membered ring).

From the viewpoint of pattern miniaturization, $L_2$ is preferably a secondary or tertiary alkyl group, and more preferably the tertiary alkyl group. Examples of the secondary alkyl group include an isopropyl group, a cyclohexyl group, and a norbornyl group, and examples of the tertiary alkyl group include a tert-butyl group and an adamantane group. In these aspects, since the glass transition temperature (Tg) and the activation energy are higher, it is possible to suppress fogging in addition to ensuring film hardness.

In Formula (Y4), Ar represents an aromatic ring group. Rn represents an alkyl group, a cycloalkyl group, or an aryl group. Rn and Ar may be bonded to each other to form a non-aromatic ring. Ar is more preferably an aryl group.

The resin (A) preferably has an acetal structure.

The acid-decomposable group preferably has an acetal structure. The acetal structure is, for example, a structure in which a polar group such as a carboxyl group, a phenolic hydroxyl group, and a fluorinated alcohol group is protected with the group represented by Formula (Y3).

The repeating unit having an acid-decomposable group is preferably a repeating unit represented by General Formula (AP).

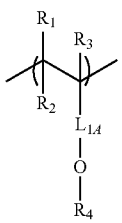

(AP)

$L_{1A}$ represents a divalent linking group, $R_1$ to $R_3$ each independently represent a hydrogen atom or a monovalent substituent, and $R_4$ represents a group that is eliminated through decomposition by the action of an acid.

$L_{1A}$ represents a divalent linking group. Examples of the divalent linking group include —CO—, —O—, —S—, —SO—, —SO$_2$—, a hydrocarbon group (for example, an alkylene group, a cycloalkylene group, an alkenylene group, and an arylene group), and a linking group in which a plurality of these groups are linked.

Among those, L1A is preferably —CO— or the arylene group.

As the arylene group, a phenylene group is preferable.

The alkylene group may be linear or branched. The number of carbon atoms of the alkylene group is not particularly limited, but is preferably 1 to 10, and more preferably 1 to 3.

$R_1$ to $R_3$ each independently represent a hydrogen atom or a monovalent substituent. Examples of the monovalent substituent include an alkyl group, a cycloalkyl group, and a halogen atom.

The alkyl group may be linear or branched. The number of carbon atoms of the alkyl group is not particularly limited, but is preferably 1 to 10, and more preferably 1 to 3.

The cycloalkyl group may be monocyclic or polycyclic. This cycloalkyl group preferably has 3 to 8 carbon atoms.

Examples of the halogen atom include a fluorine atom, a chlorine atom, a bromine atom, and an iodine atom.

$R_4$ represents a group that is eliminated through decomposition by the action of an acid (eliminable group).

Among those, examples of the eliminable group include the groups represented by Formulae (Y1) to (Y4), and the group represented by Formula (Y3) is preferable.

In a case where each of the groups has a substituent, examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms). The substituent preferably has 8 or less carbon atoms.

As the repeating unit having an acid-decomposable group, a repeating unit represented by General Formula (AI) is also preferable.

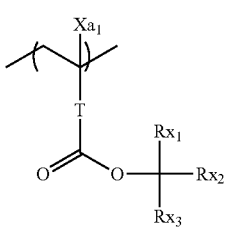

(AI)

In General Formula (AI), $Xa_1$ represents a hydrogen atom or an alkyl group.

T represents a single bond or a divalent linking group.

$Rx_1$ to $Rx_3$ each independently represent an (linear or branched) alkyl group or a (monocyclic or polycyclic) cycloalkyl group. It should be noted that in a case where all of $Rx_1$ to $Rx_3$ are (linear or branched) alkyl groups, at least two of $Rx_1$, $Rx_2$, or $Rx_3$ are preferably methyl groups.

Two of $Rx_1$ to $Rx_3$ may be bonded to each other to form a (monocyclic or polycyclic) cycloalkyl group.

Examples of the alkyl group represented by $Xa_1$ include a methyl group and a group represented by —CH$_2$—R$_{11}$. $R_{11}$ represents a halogen atom (a fluorine atom or the like), a hydroxyl group, or a monovalent organic group, examples thereof include an alkyl group having 5 or less carbon atoms and an acyl group having 5 or less carbon atoms, the alkyl group having 3 or less carbon atoms is preferable, and a methyl group is more preferable. $Xa_1$ is preferably a hydrogen atom, a methyl group, a trifluoromethyl group, or a hydroxymethyl group.

Examples of the divalent linking group of T include an alkylene group, an aromatic ring group, a —COO-Rt- group, and an —O-Rt- group. In Formulae, Rt represents an alkylene group or a cycloalkylene group.

T is preferably a single bond, or the —COO-Rt- group. In a case where T represents the —COO-Rt- group, Rt is preferably an alkylene group having 1 to 5 carbon atoms, and is more preferably a —CH$_2$— group, a —(CH$_2$)$_2$— group, or a —(CH$_2$)$_3$— group.

As the alkyl group of each of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the cycloalkyl group formed by the bonding of two of $Rx_1$ to $Rx_3$, a monocyclic cycloalkyl group such as a cyclopentyl group and a cyclohexyl group is preferable, and in addition, a polycyclic cycloalkyl group such as a norbornyl group, a tetracyclodecanyl group, a tetracyclododecanyl group, and an adamantyl group is preferable. Among those, a monocyclic cycloalkyl group having 5 or 6 carbon atoms is preferable.

In the cycloalkyl group formed by the bonding of two of $Rx_1$ to $Rx_3$, for example, one of the methylene groups constituting the ring may be substituted with a heteroatom such as an oxygen atom or a group having a heteroatom, such as a carbonyl group.

With regard to the repeating unit represented by General Formula (AI), for example, an aspect in which $Rx_1$ is a methyl group or an ethyl group, and $Rx_2$ and $Rx_3$ are bonded to each other to form the above-mentioned cycloalkyl group is preferable.

In a case where each of the groups has a substituent, examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms). The substituent preferably has 8 or less carbon atoms.

The repeating unit represented by General Formula (AT) is preferably an acid-decomposable tertiary alkyl (meth)acrylate ester-based repeating unit (the repeating unit in which $Xa_1$ represents a hydrogen atom or a methyl group, and T represents a single bond).

The resin (A) may include only one kind of the repeating units having an acid-decomposable group or a combination of two or more kinds of the repeating units.

The content of the repeating unit having an acid-decomposable group included in the resin (A) (in a case where a plurality of the repeating units having an acid-decomposable group are present, a total content thereof) is preferably 10% to 90% by mole, more preferably 20% to 80% by mole, and still more preferably 30% to 70% by mole with respect to all the repeating units of the resin (A).

(Repeating Unit Having Lactone Group or Sultone Group)

The resin (A) may further have a repeating unit having a lactone group or a sultone group.

As the lactone group or the sultone group, any of groups having a lactone structure or a sultone structure can be used, but a group having a 5- to 7-membered ring lactone structure or a 5- to 7-membered ring sultone structure is preferable; and the group in which another ring structure is fused to the 5- to 7-membered ring lactone structure so as to form a bicyclo structure or a spiro structure, or the group in which another ring structure is fused to the 5- to 7-membered ring sultone structure so as to form a bicyclo structure or a spiro structure is more preferable. The resin (A) more preferably has a repeating unit having a group having lactone structure represented by any of General Formulae (LC1-1) to (LC1-21) or a group having a sultone structure represented by any of General Formula (SL1-1), (SL1-2), or (SL1-3). Further, a group having a lactone structure or a sultone structure may be bonded directly to the main chain. As the preferred structure, groups represented by General Formula (LC1-1), General Formula (LC1-4), General Formula (LC1-5), General Formula (LC1-6), General Formula (LC1-13), and General Formula (LC1-14) are preferable.

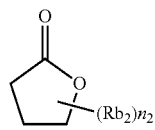
LC1-1

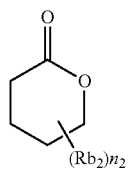
LC1-2

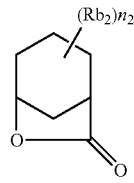
LC1-3

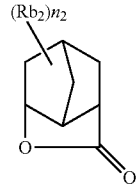
LC1-4

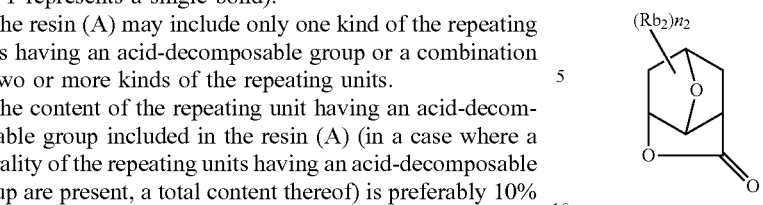
LC1-5

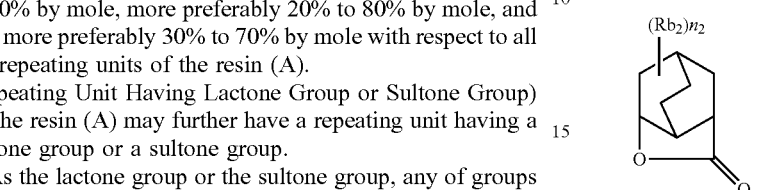
LC1-6

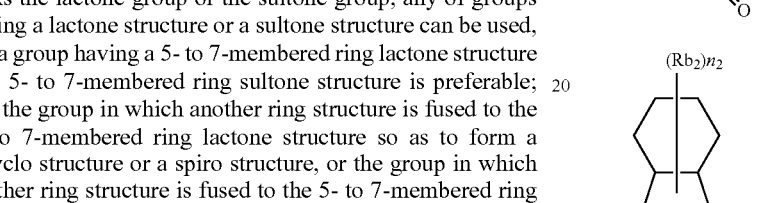
LC1-7

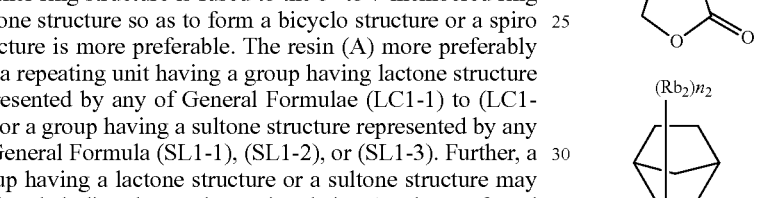
LC1-8

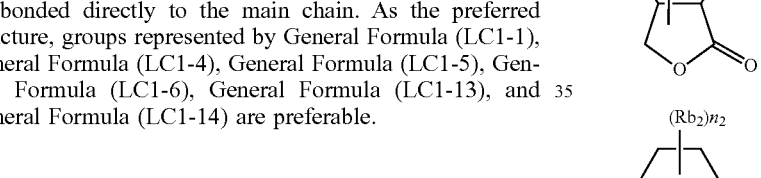
LC1-9

LC1-10

LC1-11

LC1-12

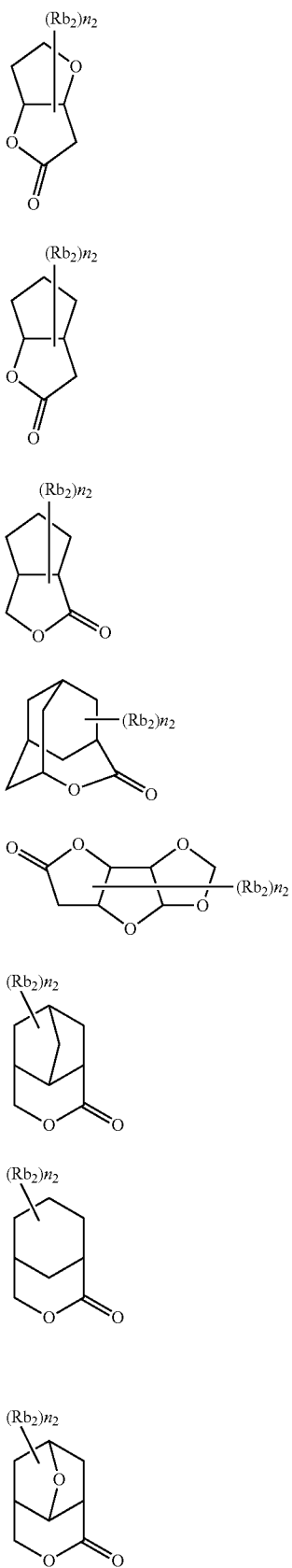

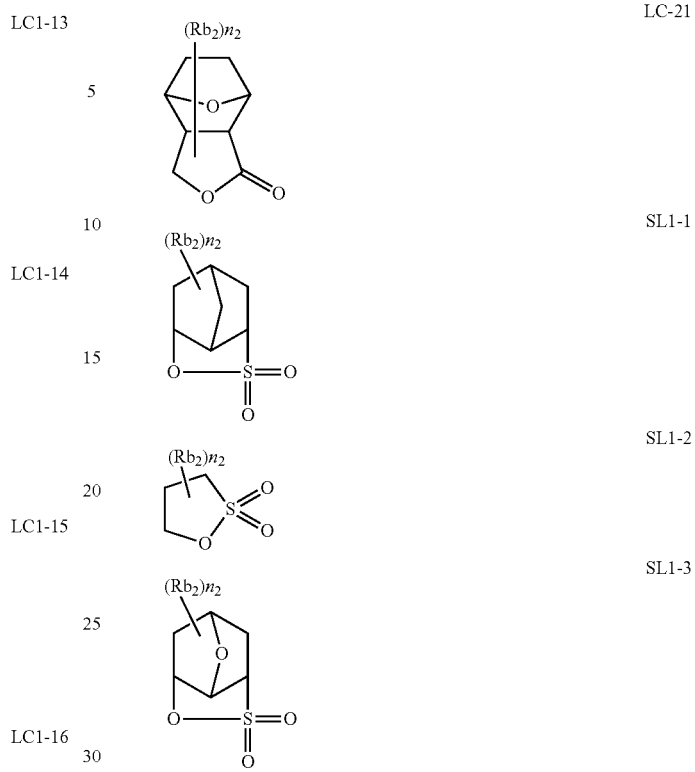

The lactone structural moiety or the sultone structural moiety may have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, and an acid-decomposable group. n2 represents an integer of 0 to 4, In a case where n2 is 2 or more, $Rb_2$'s which are present in a plural number may be different from each other, and $Rb_2$'s which are present in a plural number may be bonded to each other to form a ring.

Examples of the repeating unit having the group having a lactone structure or a sultone structure include a repeating unit represented by General Formula (AQ).

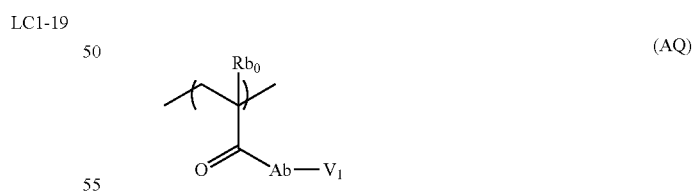

In General Formula (AQ), $Rb_0$ represents a hydrogen atom, a halogen atom, or an alkyl group having 1 to 4 carbon atoms.

Preferred examples of the substituent which may be contained in the alkyl group of $Rb_0$ include a hydroxyl group and a halogen atom.

Examples of the halogen atom of $Rb_0$ include a fluorine atom, a chlorine atom, a bromine atom, and an iodine atom. $Rb_0$ is preferably the hydrogen atom or a methyl group.

Ab represents a single bond, an alkylene group, a divalent linking group having a monocyclic or polycyclic alicyclic hydrocarbon structure, an ether group, an ester group, a carbonyl group, a carboxyl group, or a divalent group formed by combination thereof. Among those, the single bond or a linking group represented by -Ab$_1$-CO$_2$— is preferable. Ab$_1$ is a linear or branched alkylene group or a monocyclic or polycyclic cycloalkylene group, and preferably a methylene group, an ethylene group, a cyclohexylene group, an adamantylene group, or a norbornylene group.

V$_1$ represents a group having a lactone structure or a sultone structure.

As the group having the lactone structure or the sultone structure of V$_1$, a group represented by any of General Formulae (LC1-1) to (LC1-21) and General Formulae (SL1-1) to (SL1-3) is preferable.

The repeating unit having the group having a lactone structure or a sultone structure usually has optical isomers, and any of optical isomers may be used. In addition, one kind of optical isomers may be used alone or a plurality of kinds of optical isomers may be mixed and used. In a case where one kind of optical isomers is mainly used, an optical purity (ee) thereof is preferably 90 or more, and more preferably 95 or more.

Specific examples of the repeating unit having the group having a lactone structure or a sultone structure are shown below, but the present invention is not limited thereto. In the formulae, Rx represents H, CH$_3$, CH$_2$OH, or CF$_3$.

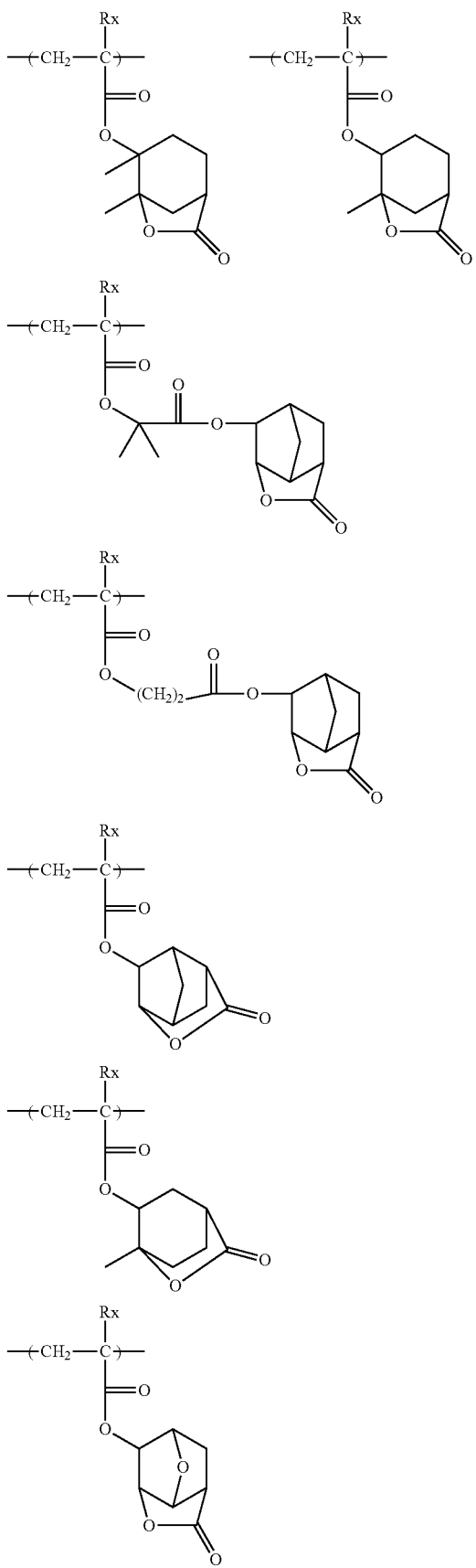

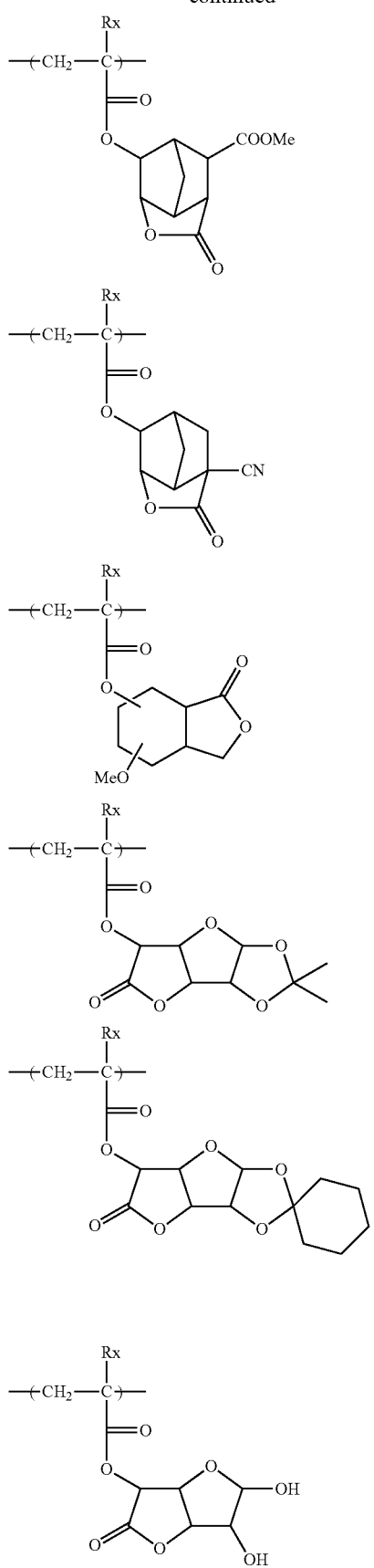
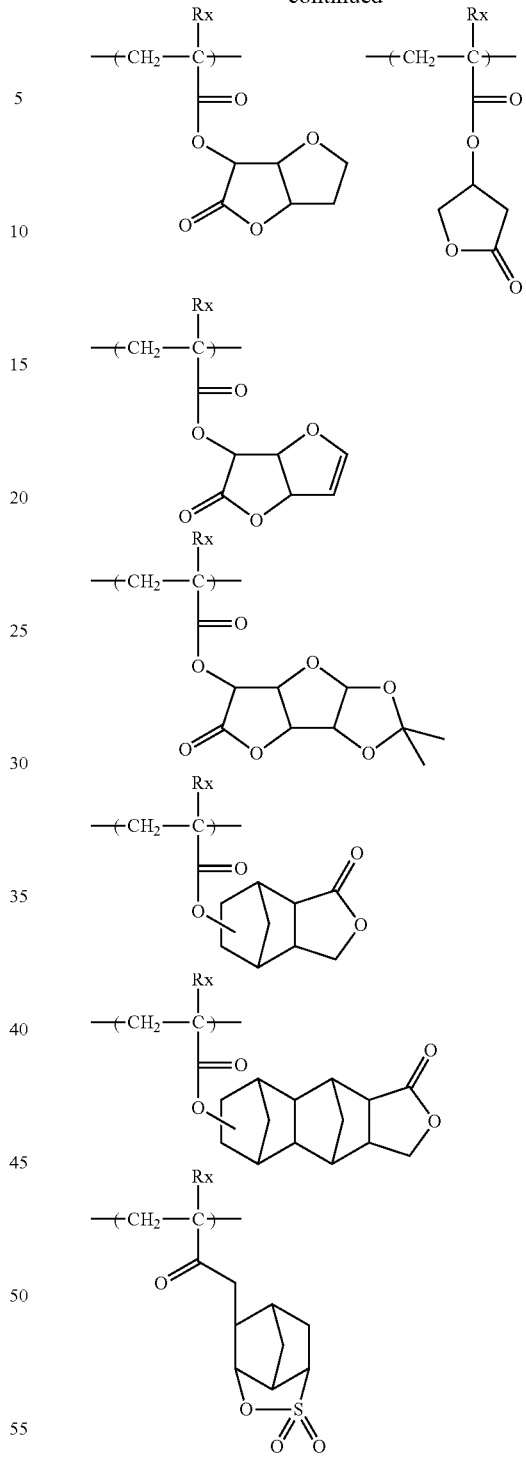

The content of the repeating unit having a lactone group or a sultone group is preferably 1% to 60% by mole, more preferably 5% to 50% by mote, and still more preferably 10% to 40% by mole with respect to all the repeating units in the resin (A).

(Repeating Unit Having Acid Group)

The resin (A) may have a repeating unit having an acid group.

As the acid group, an acid group having an acid dissociation constant (pKa) of 13 or less is preferable.

The pKa is the same as the pKa in the pKa of the acid produced from a photoacid generator which will be described later.

As the repeating unit having an acid group, a repeating unit represented by General Formula (AB) is preferable.

(AB)

$R_{31}$ represents a hydrogen atom or a monovalent organic group.

As the monovalent organic group, a group represented by -$L_{4A}$-$R_{81}$ is preferable. $L_{4A}$ represents a single bond or an ester group. Examples of $R_{81}$ include an alkyl group, a cycloalkyl group, an aryl group, and a group formed by combination thereof.

$R_{41}$ and $R_{51}$ each independently represent a hydrogen atom, a halogen atom, or an alkyl group.

Examples of the halogen atom include a fluorine atom, a chlorine atom, a bromine atom, or an iodine atom.

$L_{2A}$ represents a single bond or an ester group.

$L_{3A}$ represents an (n+m+1)-valent aromatic hydrocarbon ring group or an (n+m+1)-valent alicyclic hydrocarbon ring group. Examples of the aromatic hydrocarbon ring group include a benzene ring group and a naphthalene ring group. The alicyclic hydrocarbon ring group may be either a monocycle or a polycycle, and examples thereof include a cycloalkyl ring group.

$R_{61}$ represents a hydroxyl group or a fluorinated alcohol group (preferably a hexafluoroisopropanol group). Further, in a case where Rei is a hydroxyl group, $L_{3A}$ is preferably the (n+m+1)-valent aromatic hydrocarbon ring group.

$R_{71}$ represents a halogen atom. Examples of the halogen atom include a fluorine atom, a chlorine atom, a bromine atom, or an iodine atom.

m represents an integer of 1 or more, m is preferably an integer of 1 to 3 and more preferably an integer of 1 or 2.

n represents 0 or an integer of 1 or more, n is preferably an integer of 1 to 4.

Furthermore, (n+m+1) is preferably an integer of 1 to 5.

As the repeating unit having an acid group, a repeating unit represented by General Formula (I) is also preferable.

(I)

In General Formula (I), $R_{41}$, $R_{42}$, and $R_{43}$ each independently represent a hydrogen atom, an alkyl group, a cycloalkyl group, a halogen atom, a cyano group, or an alkoxycarbonyl group. It should be noted that $R_{42}$ may be bonded to $Ar_4$ to form a ring, in which case $R_{42}$ represents a single bond or an alkylene group.

$X_4$ represents a single bond, —COO—, or —CONR$_{64}$—, and $R_{64}$ represents a hydrogen atom or an alkyl group.

$L_4$ represents a single bond or an alkylene group.

$Ar_4$ represents an (n+1)-valent aromatic ring group, and in a case where $Ar_4$ is bonded to $R_{42}$ to form a ring, $Ar_4$ represents an (n+2)-valent aromatic ring group, n represents an integer of 1 to 5.

As the alkyl group represented by each of $R_{41}$, $R_{42}$, and $R_{43}$ in General Formula (I), an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group is preferable, an alkyl group having 8 or less carbon atoms is more preferable, and an alkyl group having 3 or less carbon atoms is still more preferable.

The cycloalkyl group of each of $R_{41}$, $R_{42}$, and $R_{43}$ in General Formula (I) may be monocyclic or polycyclic. Among those, a cycloalkyl group having 3 to 8 carbon atoms, such as a cyclopropyl group, a cyclopentyl group, and a monocyclic cyclohexyl group, is preferable.

Examples of the halogen atom of each of $R_{41}$, $R_{42}$, and $R_{43}$ in General Formula (I) include a fluorine atom, a chlorine atom, a bromine atom, and an iodine atom, and the fluorine atom is preferable.

As the alkyl group included in the alkoxycarbonyl group of each of $R_{41}$, $R_{42}$, and $R_{43}$ in General Formula (I), the same ones as the alkyl group in each of $R_{41}$, $R_{42}$, and $R_{43}$ are preferable.

Preferred examples of the substituent in each of the groups include an alkyl group, a cycloalkyl group, an aryl group, an amino group, an amide group, a ureide group, a urethane group, a hydroxyl group, a carboxyl group, a halogen atom, an alkoxy group, a thioether group, an acyl group, an acyloxy group, an alkoxycarbonyl group, a cyano group, and a nitro group. The substituent preferably has 8 or less carbon atoms.

$Ar_4$ represents an (n+1)-valent aromatic ring group. The divalent aromatic ring group in a case where n is 1 may have a substituent, and is preferably, for example, an arylene group having 6 to 18 carbon atoms, such as a phenylene group, a tolylene group, a naphthylene group, and an anthracenylene group, or an aromatic ring group including a heterocycle such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring.

Specific examples of the (n+1)-valent aromatic ring group in a case where n is an integer of 2 or more include groups formed by removing any (n−1) hydrogen atoms from the above-described specific examples of the divalent aromatic ring group.

The (n+1)-valent aromatic ring group may further have a substituent.

Examples of the substituent which can be contained in the alkyl group, the cycloalkyl group, the alkoxycarbonyl group, the alkylene group, and the (n+1)-valent aromatic ring group as mentioned above include the alkyl group; the alkoxy group such as a methoxy group, an ethoxy group, a hydroxyethoxy group, a propoxy group, a hydroxypropoxy group, and a butoxy group; an aryl group such as a phenyl group; and the like, as mentioned, for each of $R_{41}$, $R_{42}$, and $R_{43}$ in General Formula (I).

Examples of the alkyl group of $R_{64}$ in —$CONR_{64}$— represented by $X_4$ ($R_{64}$ represents a hydrogen atom or an alkyl group) include an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, and an alkyl group having 8 or less carbon atoms is preferable.

As $X_4$, the single bond, —COO—, or —CONH— is preferable, and the single bond or —COO— is more preferable.

As the alkylene group in $L_4$, an alkylene group having 1 to 8 carbon atoms, such as a methylene group, an ethylene group, a propylene group, a butylene group, a hexylene group, and an octylene group, is preferable.

As $Ar_4$, an aromatic ring group having 6 to 18 carbon atoms is preferable, and a benzene ring group, a naphthalene ring group, and a biphenylene ring group are more preferable.

The repeating unit represented by General Formula (I) preferably comprises a hydroxystyrene structure. That is, $Ar_4$ is preferably the benzene ring group.

The repeating unit represented by General Formula (I) is preferably a repeating unit represented by General Formula (1).

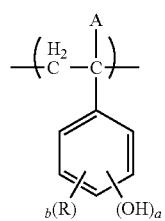

(1)

In General Formula (1),

A represents a hydrogen atom, an alkyl group, a cycloalkyl group, a halogen atom, or a cyano group.

R represents a halogen atom, an alkyl group, a cycloalkyl group, an aryl group, an alkenyl group, an aralkyl group, an alkoxy group, an alkylcarbonyloxy group, an alkylsulfonyloxy group, an alkyloxycarbonyl group, or an aryloxycarbonyl group, and in a case where a plurality of R's are present, R's may be the same as or different from each other. In a case where there are a plurality of R's, R's may be combined with each other to form a ring. As R, the hydrogen atom is preferable.

a represents an integer of 1 to 3.

b represents an integer of 0 to (3-a).

Specific examples of the repeating unit represented by General Formula (I) will be shown below, but the present invention is not limited thereto. In the formula, a represents 1 or 2.

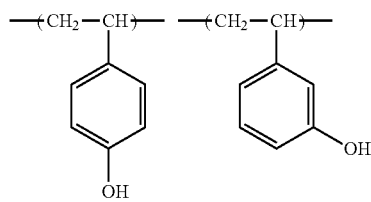

-continued

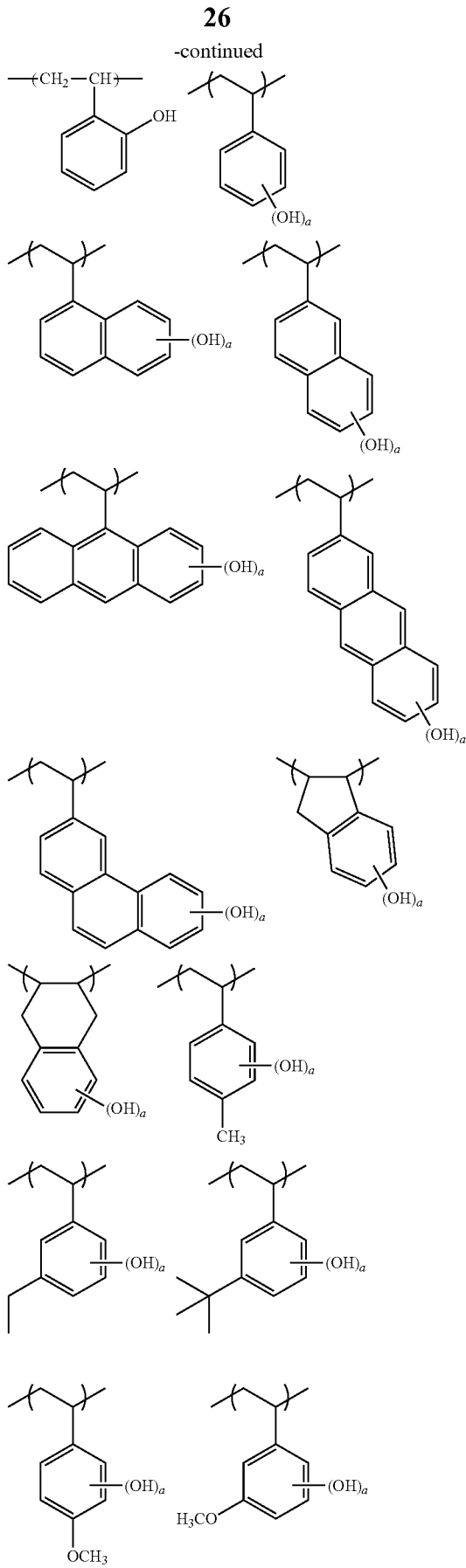

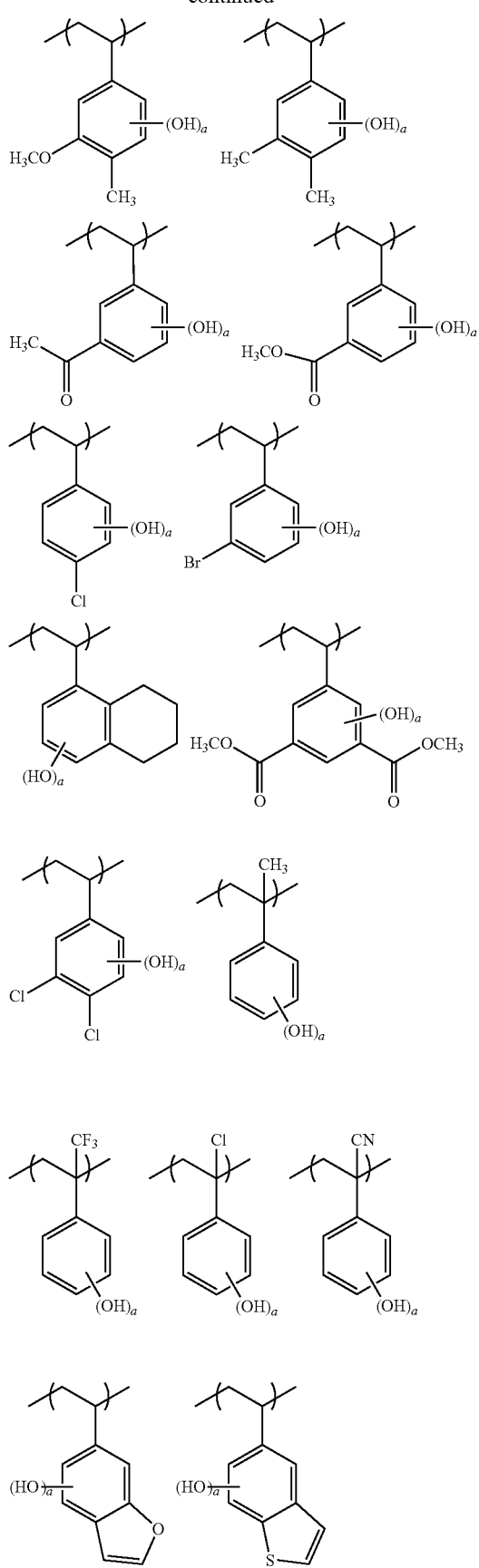
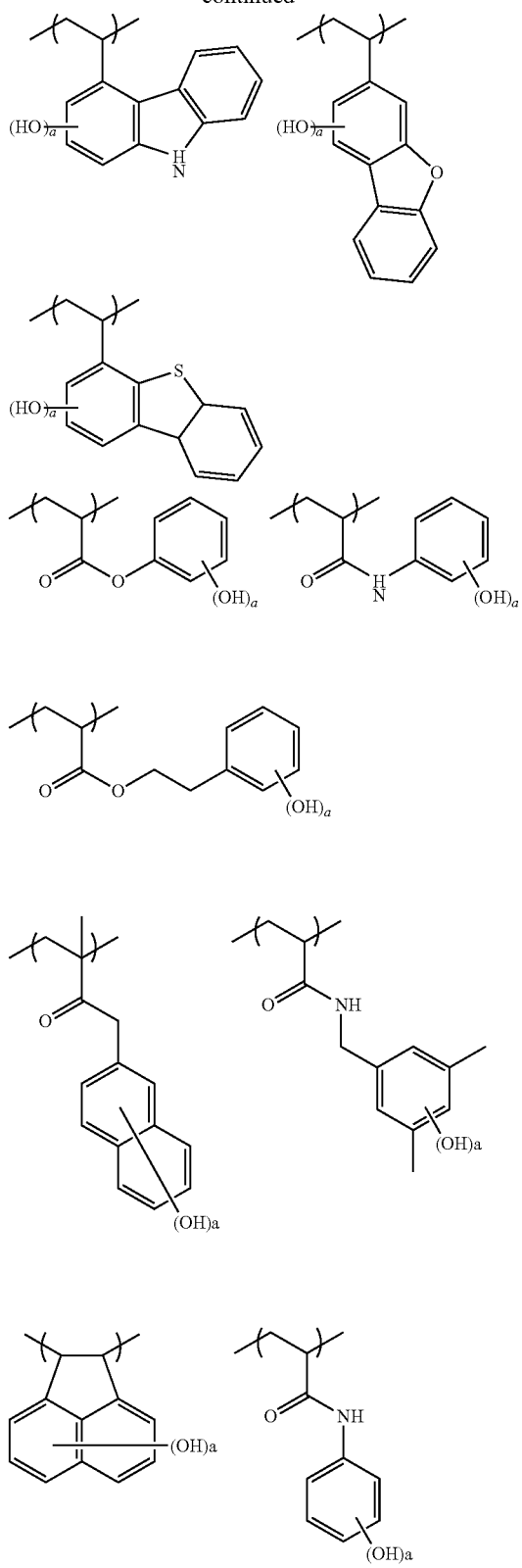
Moreover, among the repeating units, the repeating units specifically described below are preferable. In the formula, R represents a hydrogen atom or a methyl group, and a represents 2 or 3.

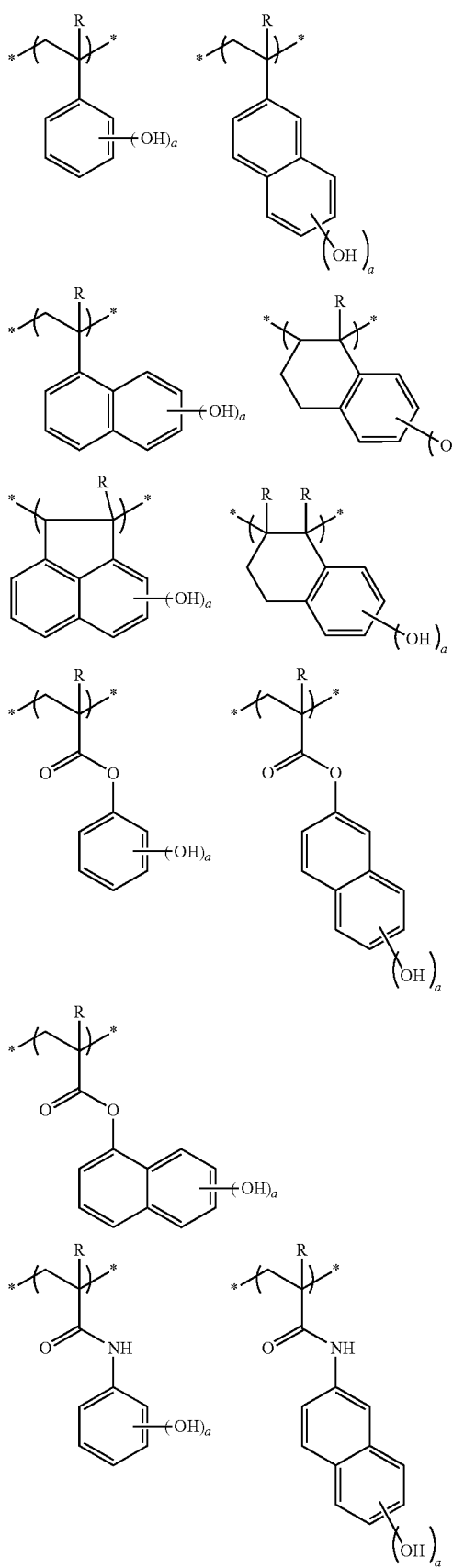

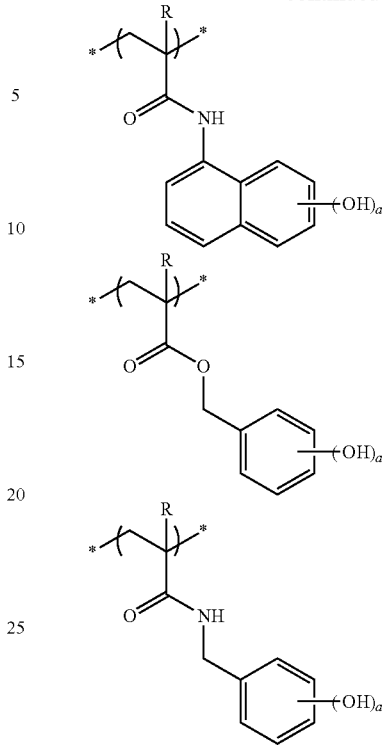

The content of the repeating unit having an acid group is preferably 10% to 80% by mole, more preferably 15% to 75% by mole, and still more preferably 20% to 70% by mole with respect to all the repeating units in the resin (A).

The resin (A) may have a variety of repeating units, in addition to the above-mentioned repeating structural units, for the purpose of adjusting dry etching resistance, suitability for a standard developer, adhesiveness to a substrate, a resist profile, a resolving power, heat resistance, sensitivity, and the like; and other purposes.

The resin (A) can be synthesized in accordance with an ordinary method (for example, radical polymerization). Examples of the general synthesis method include (I) a batch polymerization method in which polymerization is performed by dissolving monomer species and an initiator in a solvent and heating the solution, and (2) a dropwise addition polymerization method, in which a solution containing monomer species and an initiator is added dropwise to a heating solvent for 1 to 10 hours.

The weight-average molecular weight (Mw) of the resin (A) is preferably 1,000 to 200,000, more preferably 2,000 to 30,000, and still more preferably 3,000 to 25,000, The dispersity (Mw/Mn) is usually 1.0 to 3.0, preferably 1.0 to 2.6, more preferably 1.0 to 2.0, and still more preferably 1.1 to 2.0.

The resin (A) may be used alone or in combination of two or more kinds thereof.

The content of the resin (A) in the composition of the embodiment of the present invention is usually 20% by mass or more in many cases, preferably 40% by mass or more, more preferably 50% by mass or more, and still more preferably 60% by mass or more with respect to the total solid content. The upper limit is not particularly limited, but is preferably 99.5% by mass or less, more preferably 99% by mass or less, and still more preferably 98% by mass or less.

In addition, the total solid content of the composition of the embodiment of the present invention means other components (components that can constitute an actinic ray-sensitive or radiation-sensitive film) excluding the solvent.

<Compound that Generates Acid Upon Irradiation with Actinic Rays or Radiation>

The actinic ray-sensitive or radiation-sensitive resin composition of the embodiment of the present invention contains a compound that generates an acid upon irradiation with actinic rays or radiation (hereinafter also referred to as a "photoacid generator" or a "photoacid generator (B)").

The photoacid generator is a compound that generates an acid upon irradiation with actinic rays or radiation.

As the photoacid generator, a compound that generates an organic acid upon irradiation with actinic rays or radiation is preferable. Examples thereof include a sulfonium salt compound, an iodonium salt compound, a diazonium salt compound, a phosphonium salt compound, an imidosulfonate compound, an oxime sulfonate compound, a diazodisulfone compound, a disulfone compound, and an o-nitrobenzyl sulfonate compound.

As the photoacid generators, known compounds that generate an acid upon irradiation with actinic rays or radiation can be used alone or as a mixture thereof, appropriately selected and used. For example, the known compounds disclosed in paragraphs <0125> to <0319> of the specification of US2016/0070167A1, paragraphs <0086> to <0094> of the specification of US2015/0004544A1, and paragraphs <0323> to <0402> of the specification of US2016/0237190A1 can be suitably used.

As the photoacid generator, for example, a compound represented by General Formula (ZI), General Formula (ZII), or General Formula (ZIII) is preferable.

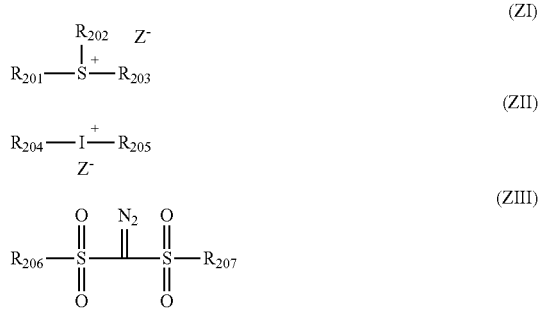

In General Formula (ZI), $R_{201}$, $R_{202}$, and $R_{203}$ each independently represent an organic group.

The organic group as each of $R_{201}$, $R_{202}$, and $R_{203}$ generally has 1 to 30 carbon atoms, and preferably has 1 to 20 carbon atoms.

In addition, two of $R_{201}$ to $R_{203}$ may be bonded to each other to form a ring structure, and the ring may include an oxygen atom, a sulfur atom, an ester bond, an amide bond, or a carbonyl group. Examples of the group formed by the bonding of two of $R_{201}$ to $R_{203}$ include an alkylene group (for example, a butylene group and a pentylene group) and —$CH_2$—$CH_2$—O—$CH_2$—$CH_2$—.

$Z^-$ represents an anion (preferably a non-nucleophilic anion).

Suitable aspects of the cation in General Formula (ZI) include the corresponding groups in a compound (ZI-1), a compound (ZI-2), a compound, represented by General Formula (ZI-3) (compound (ZI-3)), and a compound represented by General Formula (ZI-4) (compound (ZI-4)), each of which will be described later.

In addition, the photoacid generator may be a compound having a plurality of the structures represented by General Formula (ZI). For example, the photoacid generator may be a compound having a structure in which at least one of $R_{201}$, $R_{202}$, or $R_{203}$ of the compound represented by General Formula (ZI) and at least one of $R_{201}$, $R_{202}$, or $R_{203}$ of another compound represented by General Formula (ZI) are bonded via a single bond or a linking group.

First, the compound (ZI-1) will be described.

The compound (ZI-1) is an arylsulfonium compound in which at least one of $R_{201}$, $R_{202}$, or $R_{203}$ in General Formula (ZI) is an and group, that is, a compound having arylsulfonium as a cation.

In the arylsulfonium compound, all of $R_{201}$ to $R_{203}$ may be aryl groups, or some of $R_{201}$ to $R_{203}$ may be aryl groups and the remainders may be alkyl groups or cycloalkyl groups.

Examples of the arylsulfonium compound include a triarylsulfonium compound, a diarylalkylsulfonium compound, an aryldialkylsulfonium compound, a diarylcycloalkylsulfonium compound, and an aryldicycloalkylsulfonium compound.

As the aryl group included in the arylsulfonium compound, a phenyl group or a naphthyl group is preferable, and the phenyl group is more preferable. The aryl group may be an aryl group which has a heterocyclic structure having an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium compound has two or more aryl groups, the two or more aryl groups may be the same as or different from each other.

The alkyl group or the cycloalkyl group contained in the arylsulfonium compound, as necessary, is preferably a linear alkyl group having 1 to 15 carbon atoms, a branched alkyl group having 3 to 15 carbon atoms, or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

The aryl group, the alkyl group, and the cycloalkyl group of each of $R_{201}$ to $R_{203}$ may each independently have an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a halogen atom, a hydroxyl group, or a phenylthio group as a substituent.

Next, the compound (ZI-2) will be described.

The compound (ZI-2) is a compound in which $R_{201}$ to $R_{203}$ in Formula (ZI) each independently represent an organic group having no aromatic ring. Here, the aromatic ring also includes an aromatic ring including a heteroatom.

The organic group having no aromatic ring as each of $R_{201}$ to $R_{203}$ generally has 1 to 30 carbon atoms, and preferably 1 to 20 carbon atoms.

$R_{201}$ to $R_{203}$ are each independently preferably an alkyl group, a cycloalkyl group, an allyl group, or a vinyl group, more preferably a linear or branched 2-oxoalkyl group, a 2-oxocycloalkyl group, or an alkoxycarbonylmethyl group, and still more preferably the linear or branched 2-oxoalkyl group.

Preferred examples of the alkyl group and the cycloalkyl group of each of $R_{201}$ to $R_{203}$ include a linear alkyl group having 1 to 10 carbon atoms or branched alkyl group having 3 to 10 carbon atoms (for example, a methyl group, an ethyl group, a propyl group, a butyl group, and a pentyl group), and a cycloalkyl group having 3 to 10 carbon atoms (for example, a cyclopentyl group, a cyclohexyl group, and a norbornyl group).

$R_{201}$ to $R_{203}$ may be further substituted with a halogen atom, an alkoxy group (for example, having 1 to 5 carbon atoms), a hydroxyl group, a cyano group, or a nitro group.

Next, the compound (ZI-3) will be described.

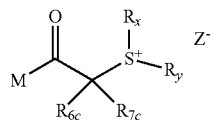

(ZI-3)

In General Formula (ZI-3), M represents an alkyl group, a cycloalkyl group, or an aryl group, and in a case where M has a ring structure, the ring structure may include at least one of an oxygen atom, a sulfur atom, an ester bond, an amide bond, or a carbon-carbon double bond. $R_{6c}$ and $R_{7c}$ each independently represent a hydrogen atom, an alkyl group, a cycloalkyl group, a halogen atom, a cyano group, or an aryl group. $R_{6c}$ and $R_{7c}$ may be bonded to each other to form a ring. $R_x$ and $R_y$ each independently represent an alkyl group, a cycloalkyl group, or an alkenyl group. $R_x$ and $R_y$ may be bonded to each other to form a ring. In addition, at least two selected from M, $R_{6c}$, or $R_{7c}$ may be bonded to each other to form a ring structure, and the ring structure may include a carbon-carbon double bond. $Z^-$ represents an anion.

In General Formula (ZI-3), as the alkyl group and the cycloalkyl group represented by M, a linear alkyl group having 1 to 15 carbon atoms (preferably having 1 to 10 carbon atoms), a branched alkyl group having 3 to 15 carbon atoms (preferably having 3 to 10 carbon atoms), or a cycloalkyl group having 3 to 15 carbon atoms (preferably having 1 to 10 carbon atoms) is preferable, and specific examples thereof include a methyl group, an ethyl group, a propyl group, an n-butyl group, a sec-butyl group, a t-butyl group, a cyclopropyl group, a cyclobutyl group, a cyclohexyl group, and a norbornyl group.

The aryl group represented by M is preferably a phenyl group or a naphthyl group, and more preferably the phenyl group. The and group may be an aryl group which has a heterocyclic structure having an oxygen atom, a sulfur atom, or the like. Examples of the heterocyclic structure include a furan ring, a thiophene ring, a benzofuran ring, and a benzothiophene ring.

M may further have a substituent (for example, a substituent T). In this aspect, examples of M include a benzyl group.

In addition, in a case where M has a ring structure, the ring structure may include at least one of an oxygen atom, a sulfur atom, an ester bond, an amide bond, or a carbon-carbon double bond.

Examples of the alkyl group, the cycloalkyl group, and the aryl group represented by each of $R_{6c}$ and $R_{7c}$ include the same ones as those of M as mentioned above, and preferred aspects thereof are also the same. In addition, $R_{6c}$ and $R_{7c}$ may be bonded to each other to form a ring.

Examples of the halogen atom represented by each of $R_{6c}$ and $R_{7c}$ include a fluorine atom, a chlorine atom, a bromine atom, and an iodine atom.

Examples of the alkyl group and the cycloalkyl group represented by each of $R_x$ and $R_y$ include the same ones as those of M as mentioned above, and preferred aspects thereof are also the same.

The alkenyl group represented by each of $R_x$ and $R_y$ is preferably an allyl group or a vinyl group.

$R_x$ and $R_y$ may further have a substituent (for example, a substituent T). In this aspect, examples of each of $R_x$ and $R_y$ include a 2-oxoalkyl group or an alkoxycarbonylalkyl group.

Examples of the 2-oxoalkyl group represented by each of $R_x$ and $R_y$ include those having 1 to 15 carbon atoms (preferably having 1 to 10 carbon atoms), and specifically a 2-oxopropyl group and a 2-oxobutyl group.

Examples of the alkoxycarbonylalkyl group represented by each of $R_x$ and $R_y$ include those having 1 to 15 carbon atoms (preferably having 1 to 10 carbon atoms). In addition, $R_x$ and $R_y$ may be bonded to each other to form a ring.

The ring structure formed by the mutual linkage of $R_x$ and $R_y$ may include an oxygen atom, a sulfur atom, an ester bond, an amide bond, or a carbon-carbon double bond.

In General Formula (ZI-3), M and Rec may be bonded to each other to form a ring structure, and the ring structure formed may include a carbon-carbon double bond.

Among those, the compound (ZI-3) is preferably a compound (ZI-3A).

The compound (ZI-3A) is a compound having a phenacylsulfonium salt structure, represented by General Formula (ZI-3A).

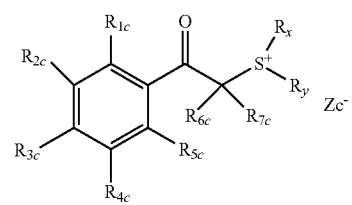

(ZI-3A)

In General Formula (ZI-3A), $R_{1c}$ to $R_{5C}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ have the same definitions as $R_{6c}$ and $R_{7c}$ in General Formula (ZI-3) as mentioned above, respectively, and preferred aspects thereof are also the same.

$R_x$ and $R_y$ have the same definitions as $R_x$ and $R_y$, respectively, in General Formula (ZI-3) described above, and preferred aspects thereof are also the same.

Any two or more of $R_{1c}$, ..., or $R_{5c}$, or $R_x$ and $R_y$ may be bonded to each other to form a ring structure, and the ring structure may each independently include an oxygen atom, a sulfur atom, an ester bond, an amide bond, or a carbon-carbon double bond. Furthermore, $R_{5c}$ and $R_{6c}$, or $R_{5c}$ and $R_x$ may be bonded to each other to form a ring structure, and the ring structure may each independently include a carbon-carbon double bond. In addition, $R_{6c}$ and $R_{7c}$ may be bonded to each other to form a ring structure.

Examples of the ring structure include an aromatic or non-aromatic hydrocarbon ring, an aromatic or non-aromatic heterocycle, and a polycyclic fused ring in which two or more of these rings are combined. Examples of the ring structure include a 3- to 10-membered ring and the ring structure is preferably a 4- to 8-membered ring, and more preferably a 5- or 6-membered ring.

Examples of the group formed by the bonding of any two or more of $R_{1c}$, ..., or $R_{5c}$, $R_{6c}$ and $R_{7c}$, and $R_x$ and $R_y$ include a butylene group and a pentylene group.

As the group formed, by the bonding of $R_{5c}$ and $R_{6c}$, and $R_{5c}$ and $R_x$, a single bond or an alkylene group is preferable. Examples of the alkylene group include a methylene group and an ethylene group.

$Zc^-$ represents an anion.

Next, the compound (ZI-4) will be described.

The compound (ZI-4) is represented by General Formula (ZI-4).

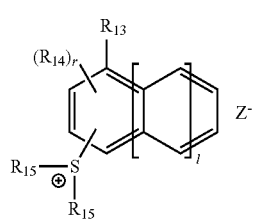

(ZI-4)

In General Formula (ZI-4), l represents an integer of 0 to 2.

r represents an integer of 0 to 8.

$R_{13}$ represents a group having a hydrogen atom, a fluorine atom, a hydroxyl group, an alkyl group, a cycloalkyl group, an alkoxy group, an alkoxycarbonyl group, or a group having a monocyclic or polycyclic cycloalkyl skeleton. These groups may have a substituent.

In a case where a plurality of $R_{14}$'S are present, $R_{14}$'s each independently represent an alkyl group, a cycloalkyl group, an alkoxy group, an alkylsulfonyl group, a cycloalkylsulfonyl group, an alkylcarbonyl group, an alkoxycarbonyl group, or an alkoxy group having a monocyclic or polycyclic cycloalkyl skeleton. These groups may have a substituent.

$R_{15}$'s each independently represent an alkyl group, a cycloalkyl group, or a naphthyl group. These groups may have a substituent. Two $R_{15}$'s may be bonded to each other to form a ring. In a case where two $R_{15}$'s are bonded to each other to form a ring, the ring skeleton may include a heteroatom such as an oxygen atom and a nitrogen atom. In one aspect, it is preferable that two $R_{15}$'s are alkylene groups and are bonded to each other to form a ring structure.

$Z^-$ represents an anion.

In General Formula (ZI-4), the alkyl group of each of $R_{13}$, $R_{14}$, and $R_{15}$ is linear or branched. The alkyl group preferably has 1 to 10 carbon atoms. As the alkyl group, a methyl group, an ethyl group, an n-butyl group, a t-butyl group, or the like is more preferable.

Next, General Formulae (ZII) and (ZIII) will be described.

In General Formulae (ZII) and (ZIII), $R_{204}$ to $R_{207}$ each independently represent an aryl group, an alkyl group, or a cycloalkyl group.

The aryl group of each of $R_{204}$ to $R_{207}$ is preferably a phenyl group or a naphthyl group, and more preferably the phenyl group. The aryl group of each of $R_{204}$ to $R_{207}$ may be an aryl group winch has a heterocyclic structure having an oxygen atom, a nitrogen atom, a sulfur atom, or the like. Examples of the skeleton of the aryl group having a hetero-cyclic structure include pyrrole, furan, thiophene, indole, benzofuran, and benzothiophene.

As the alkyl group and the cycloalkyl group of each of $R_{204}$ to $R_{207}$, a linear alkyl group having 1 to 10 carbon atoms or branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group) is preferable.

The aryl group, the alkyl group, and the cycloalkyl group of each of $R_{204}$ to $R_{207}$ may each independently have a substituent. Examples of the substituent which may be contained in the aryl group, the alkyl group, or the cycloalkyl group of each of $R_{204}$ to $R_{207}$ include an alkyl group (for example, having 1 to 15 carbon atoms), a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, and a phenylthio group.

$Z^-$ represents an anion.

As $Z^-$ in General Formula (ZI), $Z^-$ in General Formula (ZII), $Zc^-$ in General Formula (ZI-3), and $Z^-$ in General Formula (ZI-4), an anion represented by General Formula (3) is preferable.

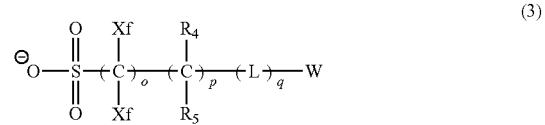

(3)

In General Formula (3), represents an integer of 1 to 3. p represents an integer of 0 to 10. q represents an integer of 0 to 10.

Xf represents a fluorine atom or an alkyl group substituted with at least one fluorine atom. The alkyl group preferably has 1 to 10 carbon atoms, and more preferably has 1 to 4 carbon atoms. In addition, a perfluoroalkyl group is preferable as the alkyl group substituted, with at least one fluorine atom.

Xf is preferably a fluorine atom or a perfluoroalkyl group having 1 to 4 carbon atoms, and more preferably a fluorine atom or $CF_3$. In particular, it is still more preferable that both Xf's are fluorine atoms.

$R_4$ and $R_5$ each independently represent a hydrogen atom, a fluorine atom, an alkyl group, or an alkyl group substituted with at least one fluorine atom. In a case where $R_4$'s and $R_5$'s are each present in a plural number, $R_4$'s and $R_5$'s may each be the same as or different from each other.

The alkyl group represented by each of $R_4$ and $R_5$ may have a substituent, and preferably has 1 to 4 carbon atoms. $R_4$ and $R_5$ are each preferably a hydrogen atom.

Specific examples and suitable aspects of the alkyl group substituted with at least one fluorine atom are the same ones as the specific examples and the suitable aspects, respectively, of Xf in General Formula (3).

L represents a divalent linking group. In a case where a plurality of L's are present, L's may be the same as or different from each other.

Examples of the divalent linking group include —COO— (—C(=O)—O—), —OCO—, —CONH—, —NHCO—, —CO—, —O—, —S—, —SO$_2$—, —SO$_2$—, an alkylene group (preferably having 1 to 6 carbon atoms), a cycloalkylene group (preferably having 3 to 15 carbon atoms), an alkenylene group (preferably having 2 to 6 carbon atoms), or a divalent linking group formed by combination of these plurality of groups. Among these, —COO—, —OCO—, —CONH—, —NHCO—, —CO—, —O—, —SO$_2$—, —COO-alkylene group-, —OCO-alkylene group-, —CONH-alkylene group-, or —NHCO-alkylene group- is preferable, and —COO—, —OCO—, —CONH—, —SO$_2$—, —COO-alkylene group-, or —OCO-alkylene group- is more preferable.

W represents an organic group including a cyclic structure. Among these, a cyclic organic group is preferable.

Examples of the cyclic organic group include an alicyclic group, an aryl group, and a heterocyclic group.

The alicyclic group may be monocyclic or polycyclic. Examples of the monocyclic alicyclic group include monocyclic cycloalkyl groups such as a cyclopentyl group, a cyclohexyl group, and a cyclooctyl group. Examples of the polycyclic alicyclic group include polycyclic cycloalkyl groups such as a norbornyl group, a tricyclodecanyl group, a tetracyclodecanyl group, a tetracyclododecanyl group, and an adamantyl group. Among those, an alicyclic group having a bulky structure having 7 or more carbon atoms, such as a norbornyl group, a tricyclodecanyl group, a tetracyclodecanyl group, a tetracyclododecanyl group, and an adamantyl group, is preferable.

The aryl group may be monocyclic or polycyclic. Examples of the aryl group include a phenyl group, a naphthyl group, a phenanthryl group, and an anthryl group.

The heterocyclic group may be monocyclic or polycyclic. The polycyclic compound can further suppress acid diffusion. Further, the heterocyclic group may have aromaticity or may not have aromaticity. Examples of the heterocycle having aromaticity include a furan ring, a thiophene ring, a benzofuran ring, a benzothiophene ring, a dibenzofuran ring, a dibenzothiophene ring, and a pyridine ring. Examples of the heterocycle not having an aromaticity include a tetrahydropyran ring, a lactone ring, a sultone ring, and a decahydroisoquinoline ring. Examples of the lactone ring and the sultone ring include the above-mentioned lactone structures and sultone structures exemplified in the resin. As the heterocycle in the heterocyclic group, the furan ring, the thiophene ring, the pyridine ring, or the decahydroisoquinoline ring is particularly preferable.

The cyclic organic group may have a substituent. Examples of the substituent include an alkyl group (which may be either linear or branched, preferably having 1 to 12 carbon atoms), a cycloalkyl group (which may be any of a monocycle, a polycycle, and a spirocycle, and preferably has 3 to 20 carbon atoms), an aryl group (preferably having 6 to 14 carbon atoms), a hydroxyl group, an alkoxy group, an ester group, an amide group, a urethane group, a ureide group, a thioether group, a sulfonamide group, and a sulfonic acid ester group. Incidentally, the carbon constituting the cyclic organic group (carbon contributing to ring formation) may be carbonyl carbon.

Preferred examples of the anion represented by General Formula (3) include SO$_3^-$—CF$_2$—CH$_2$—OCO-(L)q'-W, SO$_3^-$—CF$_2$—CHF—CH$_2$—OCO-(L)q'-W, SO$_3^-$—CF$_2$—COO-(L)q'-W, SO$_3^-$—CF$_2$—CF$_2$—CH$_2$—CH$_2$-(L)q-W, or SO$_3^-$—CF$_2$—CH(CF$_3$)—OCO-(L)q'-W. Here, L, q, and W are each the same as in General Formula (3). q' represents an integer of 0 to 10.

In one aspect, as Z$^-$ in General Formula (ZI), Z$^-$ in General Formula (ZII), Zc$^-$ in General Formula (ZI-3), and Z$^-$ in General Formula (ZI-4), an anion represented by General Formula (4) is also preferable.

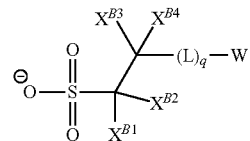

In General Formula (4), $X^{B1}$ and $X^{B2}$ each independently represent a hydrogen atom or a monovalent organic group having no fluorine atom. It is preferable that $X^{B1}$ and $X^{B2}$ are each the hydrogen atom.

$X^{B3}$ and $X^{B4}$ each independently represent a hydrogen atom or a monovalent organic group. It is preferable that at least one of $X^{B3}$ or $X^{B4}$ is a fluorine atom or a monovalent organic group having a fluorine atom, and if is more preferable that both of $X^{B3}$ and $X^{B4}$ are a fluorine atom or a monovalent organic group having a fluorine atom. If is still more preferable that $X^{B3}$ and $X^{B4}$ are both an alkyl group substituted with a fluorine atom.

L, q, and W are the same as in General Formula (3).

Z$^-$ in General Formula (ZI), Z$^-$ in General Formula (ZII), Zc$^-$ in General Formula (ZI-3), and Z$^-$ in General Formula (ZI-4) may be a benzenesulfonate anion, and are each preferably a benzenesulfonate anion substituted with a branched alkyl group or a cycloalkyl group.

As Z$^-$ in General Formula (ZI), Z$^-$ in General Formula (ZII), Zc$^-$ in General Formula (ZI-3), and Z$^-$ in General Formula (ZI-4), an aromatic sulfonate anion represented by General Formula (SA1) is also preferable.

In Formula (SA1),

Ar represents an aryl group, and may further have a substituent other than a sulfonate anion and a -(D-B) group. Examples of the substituent which may be further contained include a fluorine atom and a hydroxyl group.

n represents an integer of 0 or more, n is preferably 1 to 4, more preferably 2 or 3, and still more preferably 3.

D represents a single bond or a divalent linking group. Examples of the divalent linking group include an ether group, a thioether group, a carbonyl group, a sulfoxide group, a sulfone group, a sulfonic acid ester group, an ester group, and a group consisting of a combination of two or more of these.

B represents a hydrocarbon group.

Preferably, D is a single bond and B is an aliphatic hydrocarbon structure. It is more preferable that B is an isopropyl group or a cyclohexyl group.

Preferred examples of the sulfonium cation in General Formula (ZI) and the iodonium cation in General Formula (ZII) are shown below.

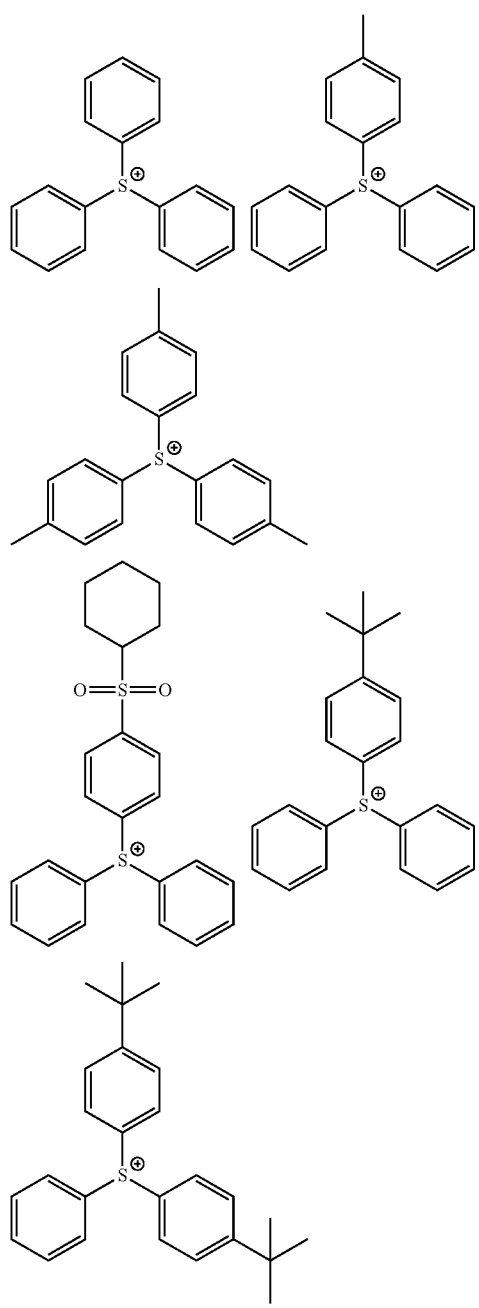
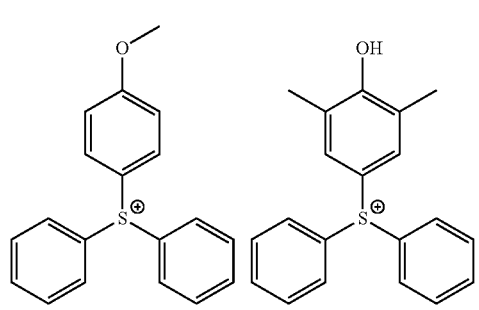
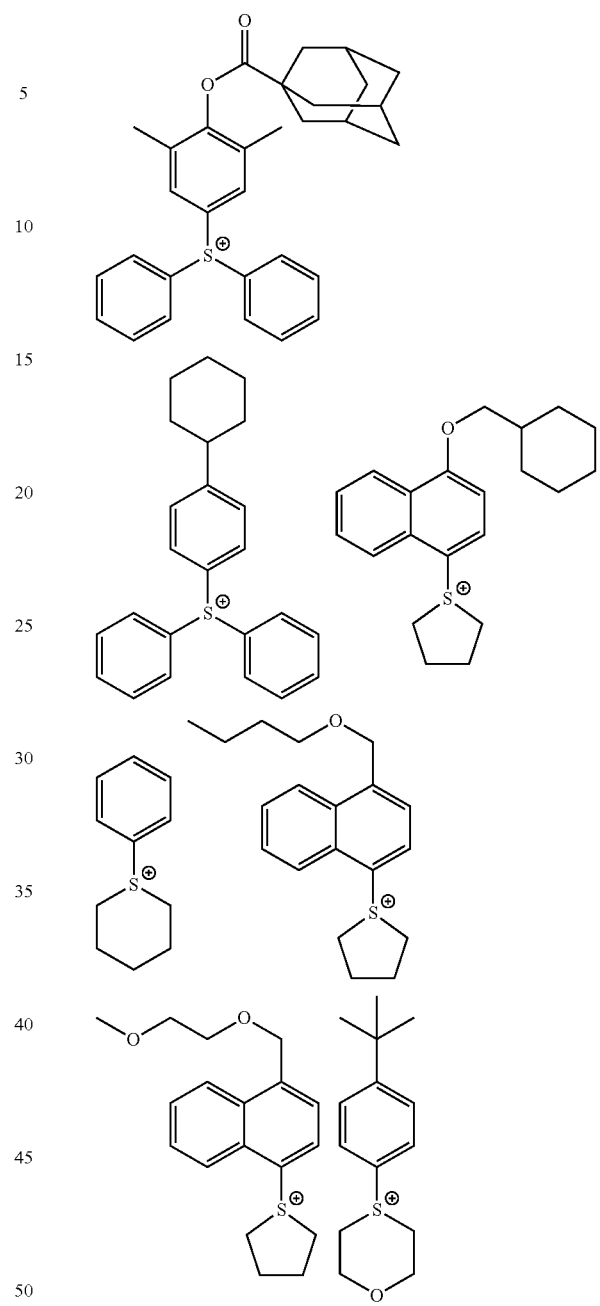
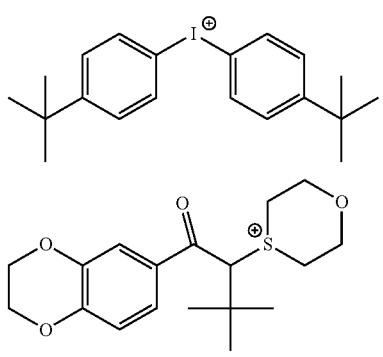

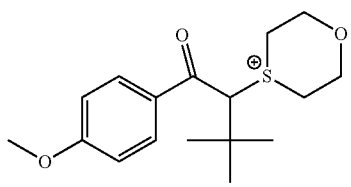
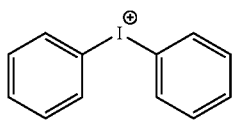
Preferred examples of the anion Z⁻ in each of General Formula (ZI) and General Formula (ZII), Zc⁻ in General Formula (ZI-3), and Z⁻ in General Formula (ZI-4) are shown below.
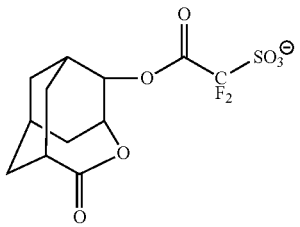
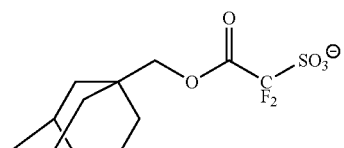
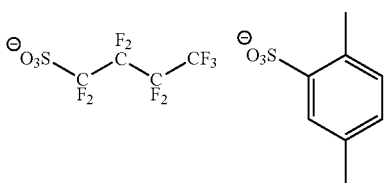
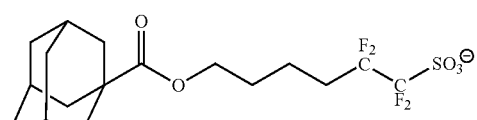
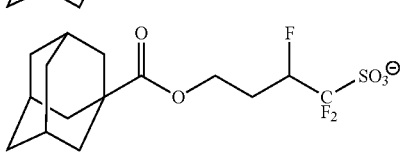
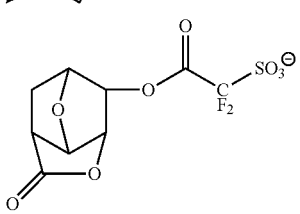
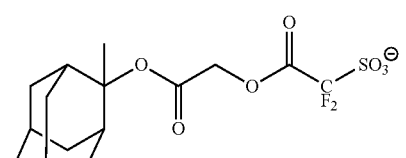
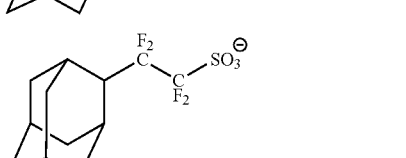
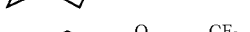
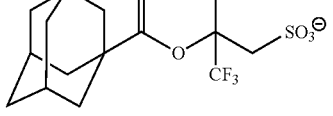

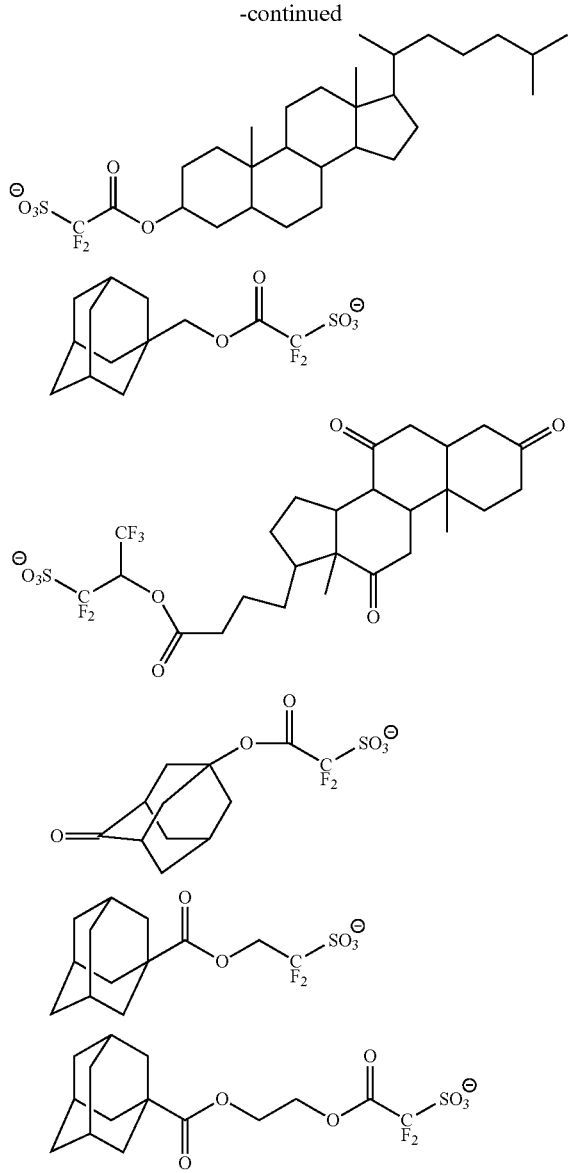

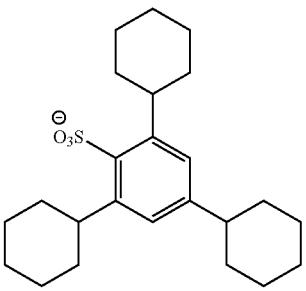

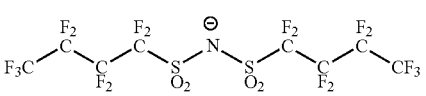

Any combination of the cations and the anions can be used as the photoacid generator.

The cation or the anion may have a lactone group or a sultone group.

As the lactone group or the sultone group, any of groups having a lactone structure or a sultone structure can be used, but a group having a 5- to 7-membered ring lactone structure or a 5- to 7-membered ring sultone structure is preferable: and the group in which another ring structure is fused to the 5- to 7-membered ring lactone structure so as to form a bicyclo structure or a spiro structure, or the group in which another ring structure is fused to the 5- to 7-membered ring sultone structure so as to form a bicyclo structure or a spiro structure is more preferable. A group having a lactone structure represented, by any of General Formulae (LC1-1) to (LC1-21) or a group having a sultone structure represented by any of General Formulae (SL1-1) to (SL1-3) is more preferable. As the preferred structure, groups represented by General Formula (LC1-1), General Formula (LC1-4), General Formula (LC1-5), General Formula (LC1-6), General Formula (LC1-13), and General Formula (LC1-14) are preferable.

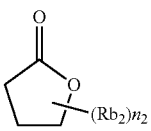

LC1-1

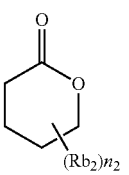

LC1-2

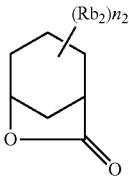

LC1-3

-continued
LC1-4
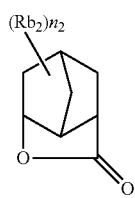
LC1-5
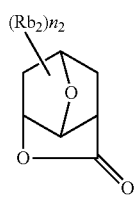
LC1-6
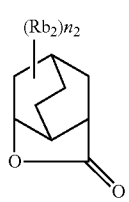
LC1-7
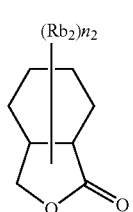
LC1-8
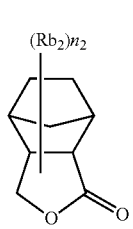
LC1-9
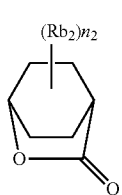
LC1-10
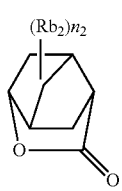
LC1-11
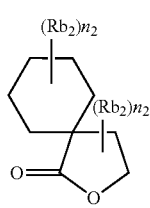
LC1-12
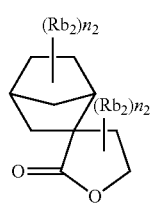
LC1-13
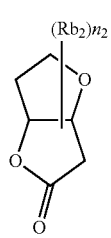
LC1-14
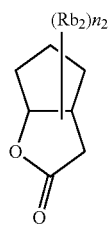
LC1-15
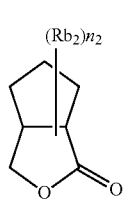
LC1-16
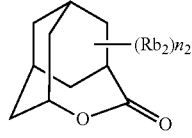
LC1-17
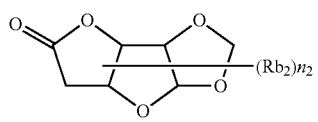
LC1-18
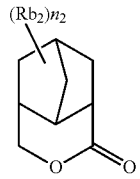
LC1-19
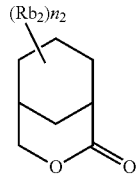

LC1-20
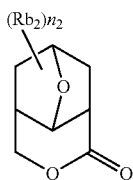

LC-21
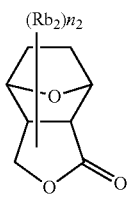

SL1-1
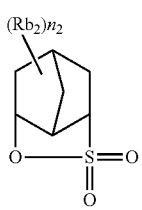

SL1-2
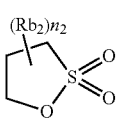

SL1-3
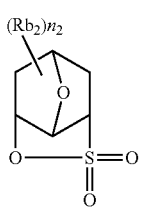

The lactone structural moiety or the sultone structural moiety may have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, and an acid-decomposable group. n2 represents an integer of 0 to 4. In a case where n2 is 2 or more, $Rb_2$'s which are present in a plural number may be different from each other, and $Rb_2$'s which are present in a plural number may be bonded to each other to form a ring.

The pKa of an acid produced from the photoacid generator is preferably from −10 to 5.

The acid dissociation constant (pKa) refers to a pKa in an aqueous solution, and is defined, in Chemical Handbook (II) (Revised 4th Edition, 1993, compiled by the Chemical Society of Japan, Maruzen Company, Ltd.). A lower value of the pKa indicates higher acid strength. Specifically, the pKa in an aqueous solution can be actually measured by using an infinite-dilution aqueous solution and measuring the acid dissociation constant at 25° C., Alternatively, the acid dissociation constant pKa can also be determined using the following software package 1 by computation from a value based on a Hammett's substituent constant and the database of publicly known literature values. Any of the pKa values described in the present specification indicate values determined by computation using the software package.

Software Package 1: Advanced Chemistry Development (ACD/Labs) Software V 8.14 for Solaris (1994-2007 ACD/Labs).

The photoacid generator may be in a form of a low-molecular-weight compound or a form incorporated into a part of a polymer. Further, a combination of the form of a low-molecular-weight compound and the form incorporated into a part of a polymer may also be used.

The photoacid generator is preferably in the form of a low-molecular-weight compound.

In a case where the photoacid generator is in the form of the low-molecular-weight compound, the molecular weight is preferably 3,000 or less, more preferably 2,000 or less, and still more preferably 1,000 or less.

In a case where the photoacid generator is in the form incorporated into a part of a polymer, it may be incorporated into the above-mentioned resin (A) or into a resin other than the resin (A).

The photoacid generators may be used alone or in combination of two or more kinds thereof.

Specific examples of the photoacid generator are described below, but the present invention is not limited thereto.

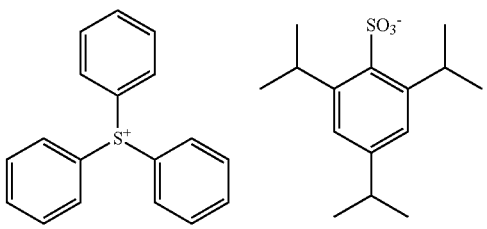

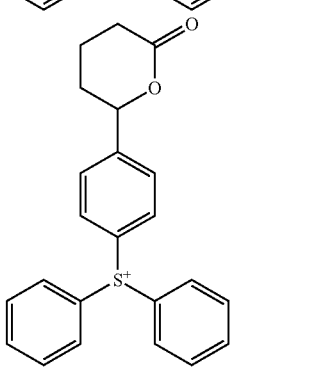

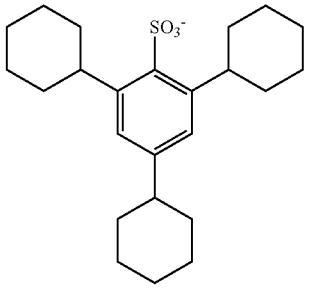

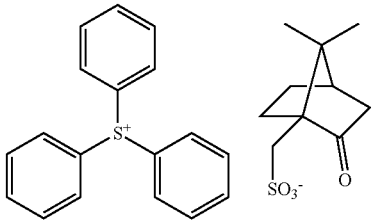

-continued

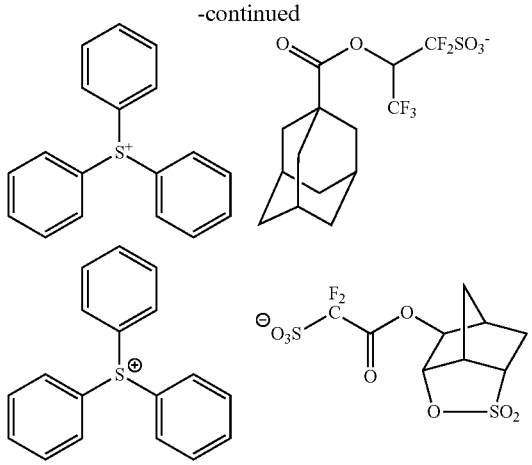

The content of the photoacid generator (in a case where a plurality of the photoacid generators are present, a total content thereof) in the composition of the embodiment of the present invention is preferably 0.1% to 35% by mass, more preferably 0.5% to 30% by mass, still more preferably 1% to 30% by mass, and particularly preferably 1% to 25% by mass, with respect to a total solid content of the composition.

<Fluorine-Containing Compound Having Group Having Solubility in Alkali Developer, which is Increased Upon Decomposition by Action of Alkali Developed>

The actinic ray-sensitive or radiation-sensitive resin composition of the embodiment of the present invention preferably contains a fluorine-containing compound (hereinafter referred to as a "fluorine-containing compound (C)") having a group having a solubility in an alkali developer which is increased, upon decomposition by the action of the alkali developer.

The fluorine-containing compound (C) can be unevenly distributed on a surface of the actinic ray-sensitive or radiation-sensitive film of the embodiment of the present invention by containing fluorine, whereby it can exhibit desired performance.

The group having a solubility in an alkali developer which is increased upon decomposition by the action of the alkali developer is also referred to as a "polarity conversion group", and specific examples thereof include a lactone group, a carboxylic acid ester group (—COO—), an acid anhydride group (—C(O)OC(O)—), an acid imide group (—NHCONH—), a carboxylic acid thioester group (—COS—), a carbonic acid ester group (—OC(O)O—), a sulfuric acid ester group (—OSO$_2$O—), and a sulfonic acid ester group (—SO$_2$O—).

Furthermore, the ester group directly linked to the main chain of the repeating unit, in the same manner as those in acrylate and the like, is deteriorated in a function of increasing a solubility in an alkali developer upon decomposition by the action of the alkali developer, and therefore, such the ester group is not included in the polarity conversion group in the present invention.

The fluorine-containing compound (C) preferably has a fluoroalkyl group from the viewpoint of surface uneven distribution.

The fluorine-containing compound (C) is more preferably a resin (also referred, to as a "resin (C)").

The fluorine-containing compound (C) is more preferably a resin including a repeating unit having a polarity conversion group (also referred to as a "repeating unit (c)").

Examples of the repeating unit (c) include a repeating unit represented by General Formula (K0).

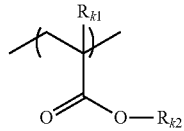

(K0)

In General Formula (K0), $R_{k1}$ represents a hydrogen atom, a halogen atom, a hydroxyl group, an alkyl group, a cycloalkyl group, an aryl group, or a group including a polarity conversion group.

$R_{k2}$ represents an alkyl group, a cycloalkyl group, an aryl group, or a group including a polarity conversion group.

It should be noted that at least one of $R_{k1}$ or $R_{k2}$ has a polarity conversion group.

In addition, the ester group directly linked to the main chain of the repeating unit represented by General Formula (K0) is not included in the polarity conversion group in the present invention, as described above.

The polarity conversion group is preferably a group represented by X in a partial structure represented by General Formula (KA-1) or (KB-1).

That is, it is preferable that the repeating unit (c) has at least one partial structure represented by General Formula (KA-1) or (KB-1), and the polarity conversion group is represented by X in the partial structure represented by has General Formula (KA-1) or (KB-1).

(KA-1)

$Y^1$—X—$Y^2$ (KB-1)

X in General Formula (KA-1) or (KB-1) represents a carboxylic acid ester group; —COO—, an acid anhydride group; —C(O)OC(O)—, an add imide group: —NHCONH—, a carboxylic acid thioester group: —COS—, a carbonic acid ester group: —OC(O)O—, a sulfuric acid ester group: —OSO$_2$O—, and a sulfonic acid ester group: —SO$_2$O—.

$Y^1$ and $Y^2$ may be the same as or different from each other, and each represent an electron-withdrawing group.

In addition, the repeating unit (c) has a group having the partial structure represented by General Formula (KA-1) or (KB-1), and thus has a preferred polarity conversion group, but in a case where the partial structure does not have a bond, such as a case of the partial structure represented by General Formula (KA-1) and the partial structure represented by General Formula (KA-B) in which $Y^1$ and $Y^2$ are monovalent, the group having the partial structure is a group having a monovalent or higher-valent group obtained by removing at least any one hydrogen atom in the partial structure.

The partial structure represented by General Formula (KA-1) or (KB-1) is linked to the main chain of the resin (C) via a substituent at any position.

The partial structure represented by General Formula (KA-1) is a structure that forms a ring structure together with the group as X.

As X in General Formula (KA-1), a carboxylic acid ester group (that is, in a case of forming a lactone ring structure as KA-1), an acid anhydride group, or a carbonic acid ester group is preferable. The carboxylic acid ester group is more preferable.

The ring structure represented by General Formula (KA-1) may have a substituent, and for example, may have nka pieces of substituents $Z_{ka1}$.

In a case where a plurality of $Z_{ka1}$'s are present, $Z_{ka1}$'s each independently represent an alkyl group, a cycloalkyl group, an ether group, a hydroxyl group, an amide group, an aryl group, a lactone ring group, or an electron-withdrawing group.

$Z_{ka1}$'s may be linked to each other to form a ring. Examples of the ring formed by the mutual linkage of $Z_{ka1}$'s include a cycloalkyl ring and a heterocycle (a cyclic ether ring, a lactone ring, and the like).

nka represents an integer of 0 to 10. nka is preferably an integer of 0 to 8, more preferably an integer of 0 to 5, still more preferably an integer of 1 to 4, and most preferably an integer of 1 to 3.

The electron-withdrawing group as $Z_{ka1}$ is the same as the electron-withdrawing group as each of $Y^1$ and $Y^2$ which will be described later, typified by a halogen atom.

In addition, the electron-withdrawing group may be substituted with another electron-withdrawing group.

$Z_{ka1}$ is preferably the alkyl group, the cycloalkyl group, the ether group, the hydroxyl group, or the electron-withdrawing group, and more preferably the alkyl group, the cycloalkyl group, or the electron-withdrawing group. In addition, the ether group is preferably an ether group substituted with an alkyl group, a cycloalkyl group, or the like, that is, an alkyl ether group or the like. Preferred examples of the electron-withdrawing group are the same ones as those of the electron-withdrawing group as each of $Y^1$ and $Y^2$ which will be described later.

Examples of the halogen atom as $Z_{ka1}$ include a fluorine atom, a chlorine atom, a bromine atom, and an iodine atom, and the fluorine atom is preferable.

The alkyl group as $Z_{ka1}$ may have a substituent and may be either linear or branched. The linear alkyl group preferably has 1 to 30 carbon atoms, and more preferably has 1 to 20 carbon atoms, and examples thereof include a methyl group, an ethyl group, an n-propyl group, an n-butyl group, a sec-butyl group, a t-butyl group, an n-pentyl group, an n-hexyl group, an n-heptyl group, an n-octyl group, an n-nonyl group, and an n-decanyl group. The branched alkyl group preferably has 3 to 30 carbon atoms, and more preferably has 3 to 20 carbon atoms, and examples thereof include an i-propyl group, an i-butyl group, a t-butyl group, an i-pentyl group, a t-pentyl group, an i-hexyl group, a t-hexyl group, an i-heptyl group, a t-heptyl group, an i-octyl group, a t-octyl group, an i-nonyl group, and a t-decanoyl group. The alkyl groups having 1 to 4 carbon atoms, such as a methyl group, an ethyl group, an n-propyl group, an i-propyl group, an n-butyl group, an i-butyl group, and a t-butyl group, are preferable.

The cycloalkyl group as $Z_{ka1}$ may have a substituent, may be monocyclic or polycyclic, and may also be bridged. For example, the cycloalkyl group may have a bridged structure. As the monocyclic group, a cycloalkyl group having 3 to 8 carbon atoms is preferable, and examples thereof include a cyclopropyl group, a cyclopentyl group, a cyclohexyl group, a cyclobutyl group, and a cyclooctyl group. Examples of the polycyclic group include groups having 5 or more carbon atoms, having a bicyclo, tricyclo, or tetracyclo structure, or the like, cycloalkyl groups having 6 to 20 carbon atoms are preferable, and examples thereof include an adamantyl group, a norbornyl group, an isobornyl group, a camphanyl group, a dicyclopentyl group, an α-pinene group, a tricyclodecanyl group, a tetracyclododecyl group, and an androstanyl group. The following structure is also preferable as the cycloalkyl group. In addition, some of the carbon atoms in the cycloalkyl group may be substituted with heteroatoms such as an oxygen atom.

(1)

(2)

(3)

(4)

(5)

(6)

(7)

(8)

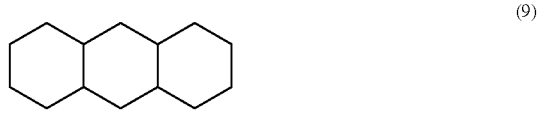

(9)

(10)

(11)

(12)

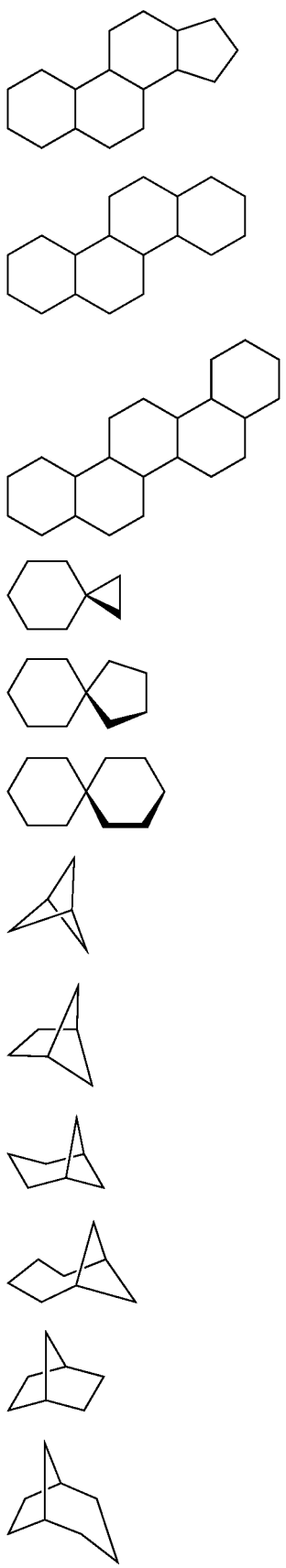
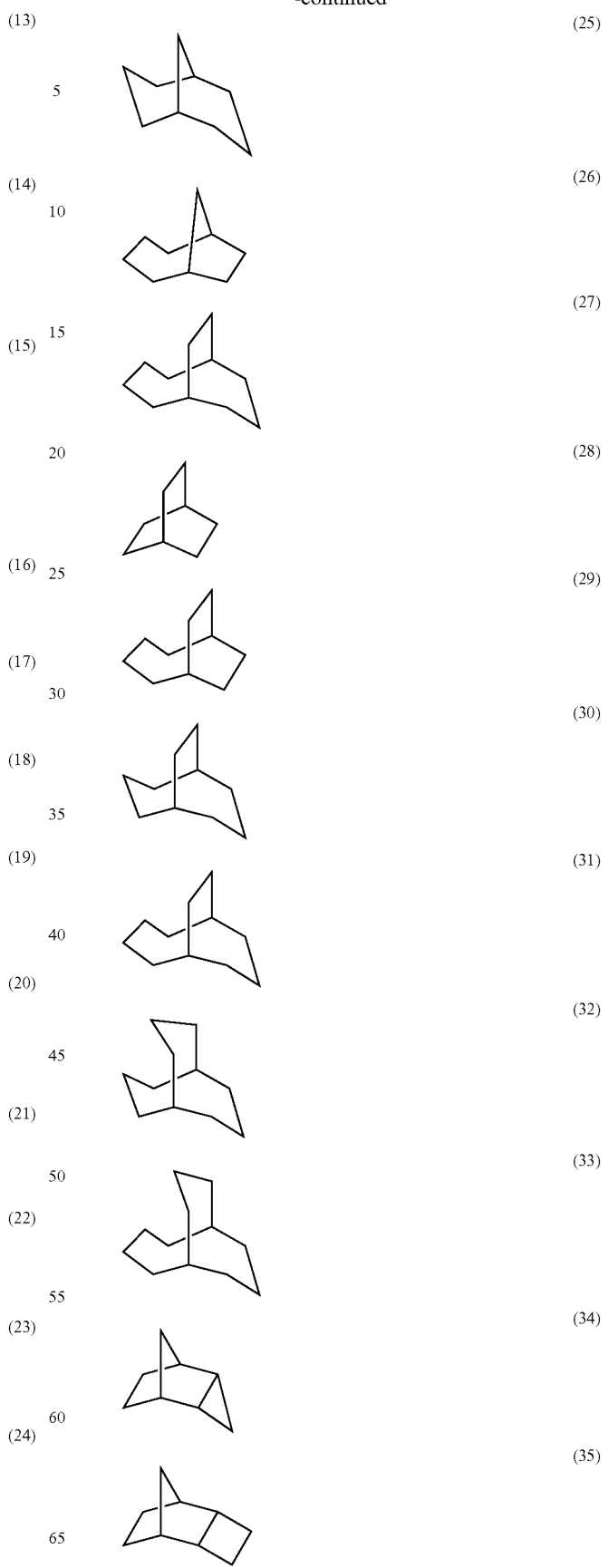

(36) 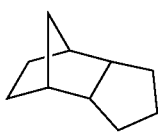

(37) 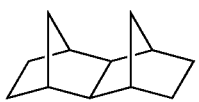

(38) 

(39) 

(40) 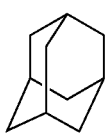

(41) 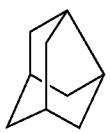

(42) 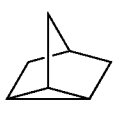

(43) 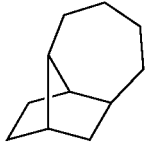

(44) 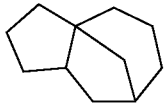

(45) 

(46) 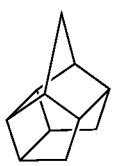

(47) 

(48) 

(49) 

(50) 

Preferred examples of the alicyclic moiety include an adamantyl group, a noradamantyl group, a decalin group, a tricyclodecanyl group, a tetracyclododecanyl group, a norbornyl group, a cedrol group, a cyclohexyl group, a cycloheptyl group, a cyclooctyl group, a cyclodecanyl group, and a cyclododecanyl group. More preferred are the adamantyl group, the decalin group, the norbornyl group, the cedrol group, the cyclohexyl group, the cycloheptyl group, the cyclooctyl group, the cyclodecanyl group, the cyclododecanyl group, and the tricyclodecanyl group.

Examples of the substituent having such the alicyclic structure include an alkyl group, a halogen atom, a hydroxyl group, an alkoxy group, a carboxyl group, and an alkoxycarbonyl group. The alkyl group preferably represents a lower alkyl group such as a methyl group, an ethyl group, a propyl group, an isopropyl group, and a butyl group, and more preferably represents the methyl group, the ethyl group, the propyl group, or the isopropyl group. As the alkoxy group, those having 1 to 4 carbon atoms, such as a methoxy group, an ethoxy group, a propoxy group, and a butoxy group, are preferable. Examples of the substituent which may be contained in each of the alkyl group and the alkoxy group include a hydroxyl group, a halogen atom, and an alkoxy group (preferably having 1 to 4 carbon atoms).

Examples of the lactone ring group of $Z_{ka1}$ include groups obtained by removing a hydrogen atom from a structure represented by any of (KA-1-1) to (KA-1-17) which will be described later.

Examples of the aryl group of $Z_{ka1}$ include a phenyl group and a naphthyl group.

Examples of the substituent which can farther be contained in the alkyl group, the cycloalkyl group, or the aryl group of $Z_{ka1}$ include a hydroxyl group, a halogen atom (fluorine, chlorine, bromine, and iodine), a nitro group, a cyano group, an alkyl group, an alkoxy group such as a methoxy group, an ethoxy group, a hydroxy ethoxy group, a propoxy group, a hydroxypropoxy group, an n-butoxy group, an isobutoxy group, a sec-butoxy group, and a t-butoxy group, an alkoxycarbonyl group such as a methoxycarbonyl group and an ethoxycarbonyl group, an aralkyl group such as a benzyl group, a phenethyl group, and a cumyl group, an aralkyloxy group, an acyl group such as a formyl group, an acetyl group, a butyryl group, a benzoyl group, a cyanamyl group, and a valeryl group, an acyloxy group such as a butyryloxy group, an alkenyl group, an alkenyloxy group such as a vinyloxy group, a propenyloxy group, an allyloxy group, and a butenyloxy group, an and group, an aryloxy group such as a phenoxy group, and an aryloxycarbonyl group such as a benzoyloxy group.

It is preferable that X in General Formula (KA-1) is the carboxylic acid ester group and the partial structure represented by General Formula (KA-1) is the lactone ring, and the partial structure is more preferably a 5- to 7-membered lactone ring.

In addition, as in (KA-1-1) to (KA-1-17), it is preferable that another ring structure is fused to the 5- to 7-membered lactone ring as the partial structure represented by General Formula (KA-1) to form a bicyclo structure or a spiro structure.

Examples of the peripheral ring structure to which the ring structure represented by General Formula (KA-1) may be bonded include the rings for (KA-1-1) to (KA-1-17), or a ring equivalent thereto.

As a structure containing the lactone ring structure represented by General Formula (KA-1), the structures represented by any of (KA-1-1) to (KA-1-17) are more preferable. Further, the lactone structure may be directly bonded to the main chain. Preferred examples of the structure include (KA-1-1), (KA-1-4), (KA-1-5), (KA-1-6), (KA-1-13), (KA-1-14), and (KA-1-17).

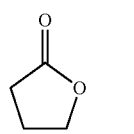

KA1-1

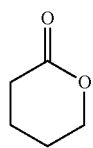

KA-1-2

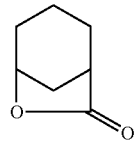

KA-1-3

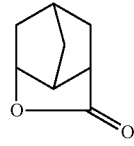

KA-1-4

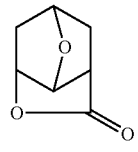

KA-1-5

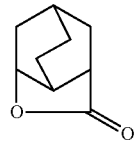

KA-1-6

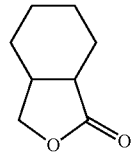

KA-1-7

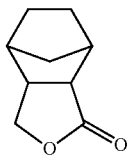

KA-1-8

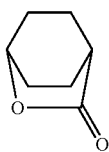

KA-1-9

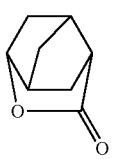

KA-1-10

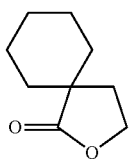

KA-1-11

KA-1-12

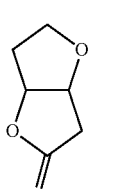

KA-1-13

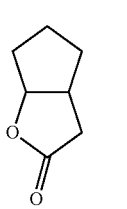

KA-1-14

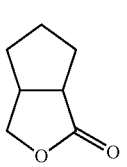

KA-1-15

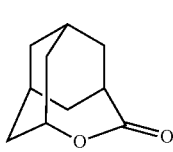

KA-1-16

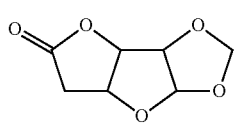
KA-1-17

The structure containing the lactone ring structure may or may not have a substituent. Preferred examples of the substituent include the same ones as those of the substituent which may be contained in the ring structure represented by General Formula (KA-1).

The lactone structure may have an optically active substance, but any of optically active substance may be used. In addition, one kind of optically active substance may be used alone or a plurality of kinds of optically active substance may be mixed and used. In a case where one kind of optically active substance is mainly used, an optical purity (ee) thereof is preferably 90% or more, more preferably 95% or more, and most preferably 98% or more.

Preferred examples of X in General Formula (KB-1) include a carboxylic acid ester group (—COO—).

$Y^1$ and $Y^2$ in General Formula (KB-1) each independently represent an electron-withdrawing group.

The electron-withdrawing group is preferably a partial structure represented by Formula (EW). In Formula (EW), * represents a bond directly linked to (KA-1) or a bond directly linked to X in (KB-1).

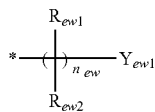
(EW)

In Formula (EW), $n_{ew}$ is a repetition number of the linking groups represented by —$C(R_{ew1})(R_{ew2})$— and represents an integer of 0 or 1, In a case where $n_{ew}$ is 0, this indicates that the bonding is formed by a single bond and $Y_{ew1}$ is directly bonded.

$Y_{ew1}$ is a halogen atom, a cyano group, a nitrile group, a nitro group, a halo(cyclo)alkyl group or haloaryl group represented by —$C(R_{f1})(R_{f2})$—$R_{f3}$ which will be described later, an oxy group, a carbonyl group, a sulfonyl group, a sulfinyl group, or a combination thereof, and the electron-withdrawing group may be, for example, the following structure. In addition, the "halo(cyclo)alkyl group" represents an alkyl or cycloalkyl group which is at least partially halogenated. $R_{ew3}$ and $R_{ew4}$ each independently represent any structure. $R_{ew3}$ and $R_{ew4}$ may have any structure, and the partial structure represented by Formula (EW) has an electron-withdrawing property, and may be linked, for example, to the main chain of the resin but is preferably an alkyl group, a cycloalkyl group, or a fluorinated alkyl group.

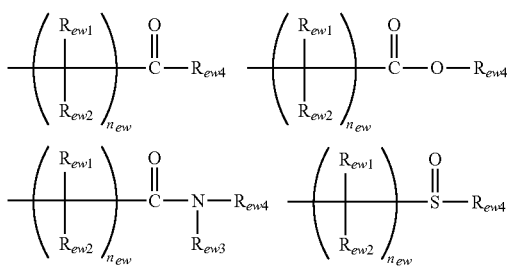

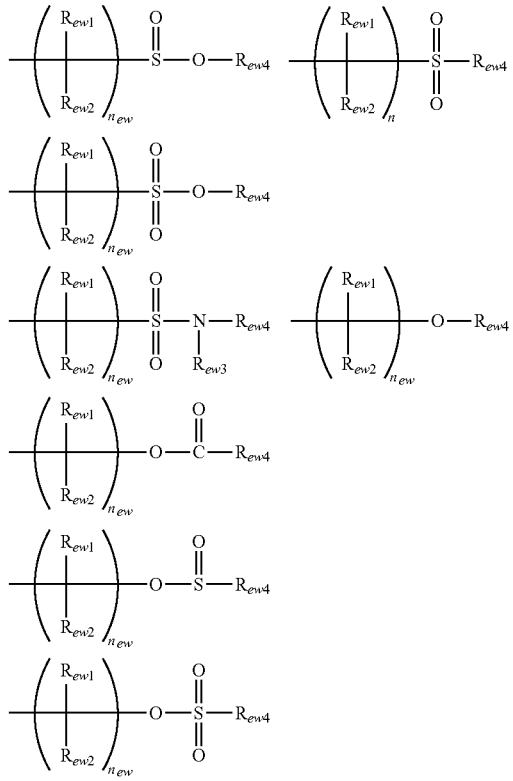

In a case where $Y_{ew1}$ is a divalent or higher valent group, the remaining bond forms a bond with any atom or substituent. At least any one group of $Y_{ew1}$, $R_{ew1}$, and $R_{ew2}$ may be linked to the main chain of the resin (C) via a further substituent.

$Y_{ew1}$ is preferably a halogen atom, or a halo(cyclo)alkyl group or haloaryl group represented by —$C(R_{f1})(R_{f2})$—$R_{f3}$.

$R_{ew1}$ and $R_{ew2}$ each independently represent any substituent, and represent, for example, a hydrogen atom, an alkyl group, a cycloalkyl group, or an aryl group.

At least two of $R_{ew1}$, $R_{ew2}$, or $Y_{ew1}$ may be linked to each other to form a ring.

Here, $R_{f1}$ represents a halogen atom, a perhaloalkyl group, a perhalocycloalkyl group, or a perhaloaryl group, more preferably represents a fluorine atom, the perfluoroalkyl group, or the perfluorocycloalkyl group, and still more preferably represents the fluorine atom or a trifluoromethyl group.

$R_{f2}$ and $R_{f3}$ each independently represent a hydrogen atom, a halogen atom, or an organic group, and $R_{f2}$ and $R_{f3}$ may be linked to each other to form a ring. The organic group represents, for example, an alkyl group, a cycloalkyl group, and an alkoxy group, and these may be substituted with a halogen atom (preferably a fluorine atom), and Re and Re are more preferably (halo)alkyl groups. It is more preferable that Re represents the same group as $R_{f1}$ or is linked to $R_{f3}$ to form a ring.

$R_{f1}$ and $R_{f3}$ may be linked to form a ring, and examples of the ring formed include a (halo)cycloalkyl ring and a (halo) aryl ring.

Examples of the (halo)alkyl group in each of $R_{f1}$ to $R_{f3}$ include the alkyl group for $Z_{ka1}$ described above and a halogenated structure thereof.

Examples of the (per)halocycloalkyl group and the (per) haloaryl group in each of $R_{f1}$ to $R_{f3}$ or in the ring formed by the linkage between $R_{f2}$ and $R_{f3}$ include structures resulting from halogenation of the cycloalkyl groups in $Z_{ka1}$, and more preferably a fluorocycloalkyl group represented by —$C_{(n)}F_{(2n-2)}H$ and a perfluoroaryl group represented by —$C_{(n)}F_{(n-1)}$. Here, the number n of carbon atoms is not particularly limited, but is preferably 5 to 13, and more preferably 6.

Preferred, examples of a ring which may be formed by the mutual linkage of at least two of $R_{ew1}$, $R_{ew2}$, or $Y_{ew1}$ include a cycloalkyl group and a heterocyclic group, and as the heterocyclic group, a lactone ring group is preferable. Examples of the lactone ring include the structures represented by Formulae (KA-1-1) to (KA-1-17).

Moreover, the repeating unit (c) may have a plurality of the partial structures represented by General Formula (KA-t), a plurality of the partial structures represented by General Formula (KB-1), or both the partial structures of General Formula (KA-1) and General Formula (KB-1).

Furthermore, a part or a whole of the partial structure of General Formula (KA-1) may also serve as the electron-withdrawing group as $Y^1$ or $Y^2$ in General Formula (KB-1). For example, in a case where X in General Formula (KA-1) is a carboxylic acid ester group, the carboxylic acid ester group can function as an electron-withdrawing group as $Y^1$ or $Y^2$ in General Formula (KB-1).

The repeating unit (e) may be any of a repeating unit (c') having a fluorine atom and a polarity conversion group on one side chain; a repeating unit (c*) having a polarity conversion group but not having a fluorine atom; and a repeating unit (c") having a polarity conversion group on one side chain and having a fluorine atom on a side chain different from the side chain in the same repeating unit; however, it is more preferable that the resin (C) has the repeating unit (c') as the repeating unit (c). That is, it is more preferable that the repeating unit (c) having at least one polarity conversion group has a fluorine atom.

In addition, in a case where the resin (C) has the repeating unit (c*), it is preferably a copolymer with a repeating unit having a fluorine atom (a repeating unit (c1) which will be described later). Further, it is preferable that the side chain having a polarity conversion group and the side chain having a fluorine atom in the repeating unit (c") are bonded to the same carbon atom in the main chain, that is, the side chains are in a positional relationship as in Formula (K1).

In the formula, B1 represents a partial structure having a polarity conversion group and B2 represents a partial structure having a fluorine atom.

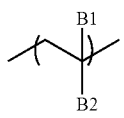

(K1)

Moreover, in the repeating unit (c*) and the repeating unit (c"), the polarity conversion group is more preferably a partial structure represented by —COO— in the structure represented by General Formula (KA-1).

The hydrolysis rate of the resin (C) with respect to an alkali developer is preferably 0.001 nm/sec or more, more preferably 0.01 nm/sec or more, still more preferably 0.1 nm/sec or more, and most preferably 1 nm/sec or more.

Here, the hydrolysis rate of the resin (C) with respect to the alkali developer refers to a rate of a decrease in the thickness of a resin film formed only of the resin (C) in an aqueous tetramethylammonium hydroxide (TMAH) solution (2.38%-by-mass) at 23° C.

The resin (C) of the present invention is preferably a resin (C1) which contains a repeating unit (c) having at least two or more polarity conversion groups and has a fluorine atom.

In a case where the repeating unit (c) has at least two polarity conversion groups, it is preferable that the repeating unit (c) has a partial structure having two polarity conversion groups, represented by General Formula (KY-1). In addition, in a case where the structure represented by General Formula (KY-1) does not have a bond, it is a monovalent or higher-valent group obtained by removing at least any one hydrogen atom in the structure.

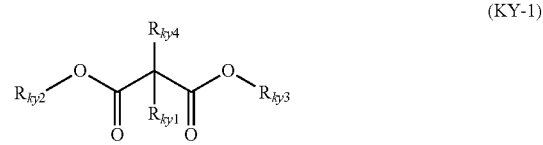

(KY-1)

In General Formula (KY-1), $R_{ky1}$ and $R_{ky4}$ each independently represent a hydrogen atom, a halogen atom, an alkyl group, a cycloalkyl group, a carbonyl group, a carbonyloxy group, an oxycarbonyl group, an ether group, a hydroxyl group, a cyano group, an amide group, or an aryl group. Alternatively, $R_{ky1}$ and $R_{ky4}$ may be bonded to the same atom to form a double bond, and for example, $R_{ky1}$ and $R_{ky4}$ may be bonded to the same oxygen atom to form a part of a carbonyl group (=O).

$R_{ky2}$ and $R_{ky3}$ are each independently an electron-withdrawing group, or $R_{ky1}$ and $R_{ky2}$ are linked to each other to form a lactone ring and $R_{ky3}$ is an electron-withdrawing group. As the lactone ring to be formed, the structures of (KA-1-1) to (KA-1-17) are preferable. Examples of the electron-withdrawing group include the same ones as those of $Y^1$ and $Y^2$ in Formula (KB-1), and the electron-withdrawing group is preferably a halogen atom, or a halo(cyclo)alkyl group or haloaryl group represented by —$C(R_{f1})(R_{f2})$—$R_{f3}$. Preferably, $R_{ky3}$ is a halogen atom, or a halo(cyclo)alkyl group or haloaryl group represented by —$C(R_{f1})(R_{f2})$—$R_{f3}$, and $R_{ky2}$ is linked to $R_{ky1}$ to form a lactone ring or is an electron-withdrawing group having no halogen atom.

$R_{ky1}$, $R_{ky2}$, and $R_{ky4}$ may be linked to each other to form a monocyclic or polycyclic structure.

Specific examples of $R_{ky1}$ and $R_{ky4}$ include the same groups as $Z_{ka1}$ in Formula (KA-1).

As the lactone ring formed by the linkage of $R_{ky1}$ and $R_{ky2}$, the structures (KA-1-1) to (KA-1-17) are preferable. Examples of the electron-withdrawing group include the same ones as those of $Y^1$ and $Y^2$ in Formula (KB-1).

The structure represented by General Formula (KY-1) is more preferably a structure represented by General Formula (KY-2). Further, the structure represented by General Formula (KY-2) is a monovalent or higher-valent group obtained by removing at least one of any hydrogen atoms in the structure.

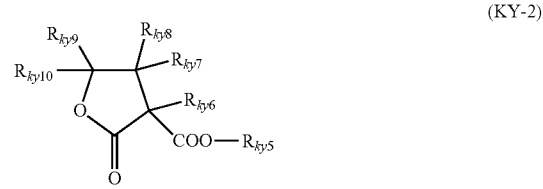

(KY-2)

In Formula (KY-2), $R_{ky6}$ to $R_{ky10}$ each independently represent a hydrogen atom, a halogen atom, an alkyl group, a cycloalkyl group, a carbonyl group, a carbonyloxy group, an oxycarbonyl group, an ether group, a hydroxyl group, a cyano group, an amide group, or an aryl group.

Two or more of $R_{ky6}$, or $R_{ky10}$ may be linked to each other to form a monocyclic or polycyclic structure.

$R_{ky5}$ represents an electron-withdrawing group. Examples of the electron-withdrawing group include the same ones as those in $Y^1$ and $Y^2$, and the electron-withdrawing group is preferably a halogen atom, or a halo(cyclo)alkyl group or haloaryl group represented by —$C(R_{f1})(R_{f2})$—$R_{f3}$.

Specific examples of $R_{ky5}$ to $R_{ky10}$ include the same groups as $Z_{ka1}$ in Formula (KA-1).

The structure represented by Formula (KY-2) is more preferably a partial structure represented by General Formula (KY-3).

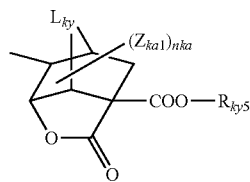

(KY-3)

In Formula (KY-3), $Z_{ka1}$ and nka each have the same definitions as in General Formula (KA-1). $R_{ky5}$ has the same definition as in Formula (KY-2).

$L_{ky}$ represents an alkylene group, an oxygen atom, or a sulfur atom. Examples of the alkylene group of $L_{ky}$ include a methylene group and an ethylene group. $L_{ky}$ is preferably the oxygen atom or the methylene group, and more preferably the methylene group.

The repeating unit (c) is not limited as long as it is a repeating unit obtained by polymerization such as addition polymerization, condensation polymerization, and addition condensation, but is preferably a repeating unit obtained by addition polymerization of carbon-carbon double bonds. Examples of the repeating unit (e) include an acrylate-based repeating unit (including a system having a substituent at the α- or β-position), a styrene-based repeating unit (including a system having a substituent at the α- or β-position), a vinyl ether-based repeating unit, a norbornene-based repeating unit, and a maleic acid derivative (maleic acid anhydride or a derivative thereof, maleimide, and the like) repeating unit; and the acrylate-based repeating unit, the styrene-based repeating unit, the vinyl ether-based repeating unit, or the norbornene-based repeating unit is preferable, the acrylate-based repeating unit, the vinyl ether-based repeating unit, or the norbornene-based repeating unit is more preferable, and the acrylate-based repeating unit is most preferable.

As a more specific structure of the repeating unit (c), a repeating unit having a partial structure shown below is preferable.

The repeating unit (c) can be a repeating unit having a partial structure shown below.

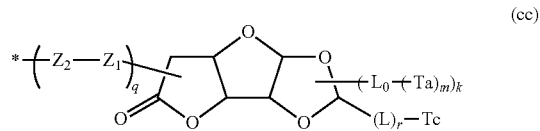

(cc)

In General Formula (cc),

In a case where a plurality of $Z_1$'s are present, $Z_1$'s each independently represent a single bond, an ether bond, an ester bond, an amide bond, a urethane bond, or a urea bond, and preferably represent the ester bond.

In a case where a plurality of $Z_2$'s are present, $Z_2$'s each independently represent a chain or cyclic alkylene group, and preferably represent an alkylene group having 1 or 2 carbon atoms or a cycloalkylene group having 5 to 10 carbon atoms.

Ta's each independently represent an alkyl group, a cycloalkyl group, an alkoxy group, a nitrile group, a hydroxyl group, an amide group, an aryl group, or an electron-withdrawing group (having the same definition as that of the electron-withdrawing group as each of $Y^1$ and $Y^2$ in General Formula (KB-1)), preferably represent the alkyl group, the cycloalkyl group, or the electron-withdrawing group, and more preferably represent the electron-withdrawing group. In a case where a plurality of Ta's are present, Ta's may be bonded to each other to form a ring.

$L_0$ represents a single bond or an m+1-valent hydrocarbon group (preferably having 20 or less carbon atoms), and preferably represents a single bond. The single bond as $L_0$ corresponds to a case where m is 1. The m+1-valent hydrocarbon group as $L_0$ represents, for example, an alkylene group, a cycloalkylene group, a phenylene group, or a m+1-valent hydrocarbon group obtained by removing any m−1 hydrogen atoms from a combination of those groups.

L's each independently represent a carbonyl group, a carbonyloxy group, or an ether group.

Tc represents a hydrogen atom, an alkyl group, a cycloalkyl group, a nitrile group, a hydroxyl group, an amide group, an aryl group, or an electron-withdrawing group (having the same definition as that of the electron-withdrawing group as each of $Y^1$ and $Y^2$ in General Formula (KB-1)).

* represents a bond to the main chain or a side chain of the resin. That is, the partial structure represented by Formula (cc) may be directly linked to the main chain, and the partial structure represented by Formula (cc) may be bonded to the side chain of the resin. Further, the bond to the main chain is a bond, to an atom which exists in a bond constituting the main chain, and the bond to a side chain is a bond to an atom which exists in a part other than a bond constituting the main chain.

m represents an integer of 1 or 28, and is preferably an integer of 1 to 3, and more preferably 1.

k represents an integer of 0 to 2, and is preferably 1.

q represents a repetition number of the groups ($Z_2$-$Z_1$), represents an integer of 0 to 5, and is preferably 0 to 2.

r represents an integer of 0 to 5.

In addition, -(L)r-Tc may be substituted with -$L_0$-(Ta)m.

A case where a sugar lactone has a fluorine atom at a terminal thereof and a case where the sugar lactone has a fluorine atom on a side chain different from the side chain on the sugar lactone side in the same repeating unit (repeating unit (c")) are also preferable.

In a case where the chain alkylene group as $Z_2$ is a linear alkylene group, it preferably has 1 to 30 carbon atoms, and more preferably has 1 to 20 carbon atoms; and in a case where the chain alkylene group is a branched, alkylene group, it preferably has 3 to 30 carbon atoms, and more preferably has 3 to 20 carbon atoms. Specific examples of the chain alkylene group as $R_2$ include a group obtained by removing one of any hydrogen atoms from the specific examples of the alkyl group as $Z_{ka1}$.

The cyclic alkylene group as $Z_2$ preferably has 3 to 8 carbon atoms, and specific examples thereof include a group obtained by removing one of any hydrogen atoms from the cycloalkyl group as $Z_{ka1}$.

The preferred number of carbon atoms and preferred specific examples of the alkyl group and cycloalkyl group as each of Ta and Tc are each the same ones as those described for the alkyl group and the cycloalkyl group as $Z_{ka1}$.

The alkoxy group as Ta preferably has 1 to 8 carbon atoms, and examples thereof include a methoxy group, an ethoxy group, a propoxy group, and a butoxy group.

Preferred examples of the aryl group as each of Ta and Tc include an aryl group having 6 to 12 carbon atoms, for example, a phenyl group and a naphthyl group.

The preferred number of carbon atoms and preferred specific examples of the alkylene group and cycloalkylene group as $L_0$ are each the same ones as those described for the chain alkylene group and the cyclic alkylene group as $Z_2$.

As a more specific structure of the repeating unit (c), a repeating unit having a partial structure shown below is preferable.

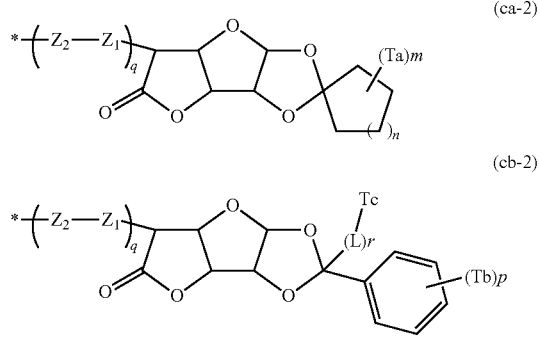

In General Formulae (ca-2) and (cb-2), n represents an integer of 0 to 11, preferably represents an integer of 0 to 5, and more preferably represents 1 or 2.

p represents an integer of 0 to 5, preferably represents an integer of 0 to 3, and more preferably represents 1 or 2.

Tb's independently represent an alkyl group, a cycloalkyl group, an alkoxy group, a nitrile group, a hydroxyl group, an amide group, an aryl group, or an electron-withdrawing group (having the same definition as that of the electron-withdrawing group as each of $Y^1$ and $Y^2$ in General Formula (KB-1)), and preferably represent the alkyl group, the cycloalkyl group, or the electron-withdrawing group. In a case where there are a plurality of Tb's, Tb's may be bonded to each other to form a ring.

* represents a bond to the main chain or a side chain of the resin. That is, the partial structure represented by Formula (ca-2) or (cb-2) may be directly linked to the main chain, or the partial structure represented by Formula (ca-2) or (cb-2) may be bonded to the side chain of the resin.

$Z_1$, $Z_2$, Ta, Tc, L, *, m, q, and r have the same definitions as in General Formula (cc), and preferred ones are also the same.

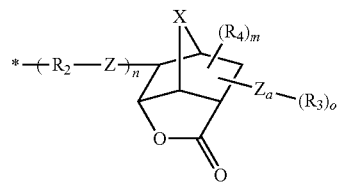

In General Formula (KY-4), $R_2$ represents a chain or cyclic alkylene group, and in a case where a plurality of Re's are present, $R_2$'s may be the same as or different from each other.

$R_3$ represents a linear, branched, or cyclic hydrocarbon group in which some or all of the hydrogen atoms on the constituent carbon are substituted with fluorine atoms.

$R_4$ represents a halogen atom, a cyano group, a hydroxy group, an amide group, an alkyl group, a cycloalkyl group, an alkoxy group, a phenyl group, an acyl group, an alkoxycarbonyl group, or a group represented by R—C(=O)— or R—C(=O)O— (R represents an alkyl group or a cycloalkyl group). In a case where a plurality of $R_4$'s are present, $R_4$'s may be the same as or different from each other, and two or more $R_4$'s may be bonded, to each other to form a ring.

X represents an alkylene group, an oxygen atom, or a sulfur atom.

In a ease where a plurality of each of Z's and Za's are present, Z's and Za's each independently represent a single bond, an ether bond, an ester bond, an amide bond, a urethane bond, or a urea bond, and in a case where a plurality of Z's and Za's are present, Z's and Za's may be each the same as or different from each other.

* represents a bond to the main chain or a side chain of the resin.

o is the number of substituents and represents an integer of 1 to 7.

m is the number of substituents and represents an integer of 0 to 7.

n represents the repetition number and represents an integer of 0 to 5.

As the structure of —$R_2$—Z—, a structure represented, by —$(CH_2)_l$—COO— is preferable (l represents an integer of 1 to 5).

The preferred number of carbon atoms and preferred specific examples of the chain or cyclic alkylene group as $R_2$ are each the same ones as those described for the chain alkylene group and the cyclic alkylene group for $Z_2$ in General Formula (cc).

With regard to the number of carbon atoms of the linear, branched, or cyclic hydrocarbon group as $R_3$, in a case where $R_3$ is a linear hydrocarbon group, the number of carbon atoms is preferably 1 to 30, and more preferably 1 to 20; in a case where $R_3$ is a branched hydrocarbon group, the number of carbon atoms is preferably 3 to 30, and more preferably 3 to 20; and in a case where $R_3$ is a cyclic hydrocarbon group, the number of carbon atoms is 6 to 20. Specific examples of $R_3$ include the specific examples of the alkyl group and the cycloalkyl group as $Z_{ka1}$ described above.

The preferred number of carbon atoms and preferred specific examples of the alkyl group and the cycloalkyl group as each of $R_4$ and R are each the same ones as those described for the alkyl group and the cycloalkyl group as $Z_{ka1}$ described above.

The acyl group as $R_4$ preferably has 1 to 6 carbon atoms, and examples thereof include a formyl group, an acetyl group, a propionyl group, a butyryl group, an isobutyryl group, a valeryl group, and a pivaloyl group.

Examples of the alkyl moiety in each of the alkoxy group and the alkoxycarbonyl group as $R_4$ include a linear, branched, or cyclic alkyl moiety, and the preferred number of carbon atoms and specific examples of the alkyl moiety are each the same ones as those described for the alkyl group and the cycloalkyl group as $Z_{ka1}$.

Examples of the alkylene group as X include a chain or cyclic alkylene group, and the preferred number of carbon atoms and specific example of the alkylene group are each the same ones as those described for the chain alkylene group and the cyclic alkylene group as $R_2$.

A repeating unit having a partial structure represented by General Formula (KY-5) is more preferable.

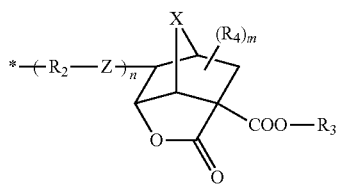

(KY-5)

In General Formula (KY-5), $R_2$ represents a chain or cyclic alkylene group, and in a case where a plurality of Jib's are present, $R_2$'s may be the same as or different from each other.

$R_3$ represents a linear, branched, or cyclic hydrocarbon group in which some or all of the hydrogen atoms on the constituent carbon are substituted with fluorine atoms.

$R_4$ represents a halogen atom, a cyano group, a hydroxy group, an amide group, an alkyl group, a cycloalkyl group, an alkoxy group, a phenyl group, an acyl group, an alkoxycarbonyl group, or a group represented by R—C(=O)— or R—C(=O)O— (R represents an alkyl group or a cycloalkyl group). In a case where there are a plurality of $R_4$'s, $R_4$'s may be the same as or different from each other, and two or more $R_4$'s may be bonded to each other to form a ring.

X represents an alkylene group, an oxygen atom, or a sulfur atom.

Z represents a single bond, an ether bond, an ester bond, an amide bond, a urethane bond, or a urea bond, and in a case where a plurality of Z's are present, Z's may be the same as or different from each other.

* represents a bond, to the main chain or a side chain of the resin.

n represents the repetition number and represents an integer of 0 to 5.

m is the number of substituents and represents an integer of 0 to 7.

The preferable range and specific examples of the number of carbon atoms for each of $R_2$ to $R_4$ and X are the same ones as those described, in General Formula (KY-4).

As the structure of —$R_2$—Z—, a structure represented by —(CH$_2$)$_l$—COO— is preferable (l represents an integer of 1 to 5).

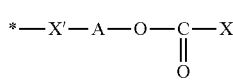

(rf-1)

-continued

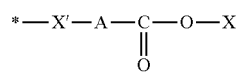

(rf-2)

In General Formulae (rf-1) and (rf-2),

X' represents an electron-withdrawing substituent, and is preferably a carbonyloxy group, an oxycarbonyl group, an alkylene group substituted with a fluorine atom, or a cycloalkylene group substituted with a fluorine atom.

A represents a single bond or a divalent linking group represented by —C(Rx)(Ry)-. Here, Rx and Ry each independently represent a hydrogen atom, a fluorine atom, an alkyl group (which preferably has 1 to 6 carbon atoms and may be substituted with a fluorine atom or the like), or a cycloalkyl group (which preferably has 5 to 12 carbon atoms and may be substituted with a fluorine atom or the like). Rx and Ry are preferably the hydrogen atom, the alkyl group, or the alkyl group substituted with a fluorine atom.

X represents an electron-withdrawing group, and is preferably a fluorinated alkyl group, a fluorinated cycloalkyl group, an aryl group substituted with fluorine or a fluorinated alkyl group, an aralkyl group substituted with fluorine or a fluorinated alkyl group.

* represents a bond to the main chain or a side chain of the resin. That is, * represents a bond which bonds to the main chain of the resin through a single bond or a linking group.

In addition, in a case where X' is a carbonyloxy group or an oxycarbonyl group, A is not a single bond.

In a case where the alkylene group in the alkylene group substituted with a fluorine atom as X' is a linear alkylene group, it preferably has 1 to 30 carbon atoms, and has more preferably 1 to 20 carbon atoms, and in a case where the alkylene group is a branched alkylene group, it preferably 3 to 30 carbon atoms, and more preferably has 3 to 20 carbon atoms. Specific examples of the alkylene group include groups obtained by removing any one hydrogen atom from the specific examples of the alkyl group as $Z_{ka1}$ described, above. The alkylene group substituted with a fluorine atom is preferably a perfluoroalkylene group.

The cycloalkylene group in the cycloalkylene group substituted with a fluorine atom as X' preferably has 3 to 8 carbon atoms, and specific examples thereof include a group obtained by removing any one hydrogen atom from the specific examples of the cycloalkyl group as $Z_{ka1}$. The cycloalkylene group substituted, with a fluorine atom is preferably a perfluorocycloalkylene group.

In a case where the alkyl group in the fluorinated alkyl group as X is a linear alkyl group, it preferably has 1 to 30 carbon atoms, and more preferably 1 to 20 carbon atoms; and in a case where the alkyl group is a branched alkyl group, it preferably has 3 to 30 carbon atoms, and more preferably has 3 to 20 carbon atoms. Specific examples of the alkyl group include the specific examples of the alkyl group as $Z_{ka1}$ described above. The fluorinated alkyl group is preferably a perfluoroalkyl group.

The cycloalkyl group in the fluorinated cycloalkyl group as X preferably has 3 to 8 carbon atoms, and specific examples thereof include the specific examples of the cycloalkyl group as $Z_{ka1}$. The fluorinated cycloalkyl group is preferably a perfluorocycloalkyl group.

The aryl group in the aryl group substituted with fluorine or a fluorinated alkyl group as X is preferably an aryl group having 6 to 12 carbon atoms, for example, a phenyl group and a naphthyl group. Further, specific examples of the fluorinated alkyl group in the aryl group substituted with a fluorinated alkyl group are the same ones as those described for the fluorinated alkyl group as X.

Preferred examples of the aralkyl group in the aralkyl group substituted with fluorine or a fluorinated alkyl group as X include an aralkyl group having 6 to 12 carbon atoms, for example, a benzyl group, a phenethyl group, a naphthylmethyl group, a naphthylethyl group, and a naphthylbutyl group. Further, specific examples of the fluorinated alkyl group in the aralkyl group substituted with a fluorinated alkyl group are the same ones as those described for the fluorinated alkyl group as X.

The resin (C) preferably has a repeating unit represented by General Formula (2) as the repeating unit (c).

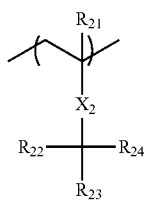

(2)

In General Formula (2), $R_{21}$ represents a hydrogen atom or a monovalent organic group. $X_2$ represents a divalent linking group. $R_{22}$ and $R_{23}$ each independently represent a fluoroalkyl group, $R_{24}$ represents a hydrogen atom, a fluorine atom, or a monovalent organic group.

As the divalent linking group represented by $X_2$ in General Formula (2), a divalent linking group having the abovementioned polarity conversion group is preferable, and a divalent linking group having a lactone structure is particularly preferable.

In General Formula (2), $R_{21}$ preferably represents a hydrogen atom or an alkyl group, and more preferably represents the hydrogen atom or an alkyl group having 1 to 5 carbon atoms.

In General Formula (2), $R_{22}$ and $R_{23}$ each independently represent a fluoroalkyl group, preferably represent a fluoroalkyl group having 1 to 10 carbon atoms, and more preferably represent a fluoroalkyl group having 1 to 5 carbon atoms.

In General Formula (2), $R_{24}$ preferably represents a hydrogen atom, a fluorine atom, or a fluoroalkyl group having 1 to 10 carbon atoms, and more preferably represents the hydrogen atom, the fluorine atom, or a fluoroalkyl group having 1 to 5 carbon atoms.

Specific examples of the repeating unit (e) having a polarity conversion group are shown below, but the present invention is not limited thereto.

Ra represents a hydrogen atom, a fluorine atom, a methyl group, or a trifluoromethyl group.

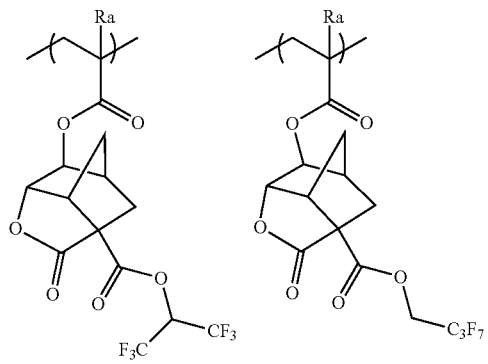

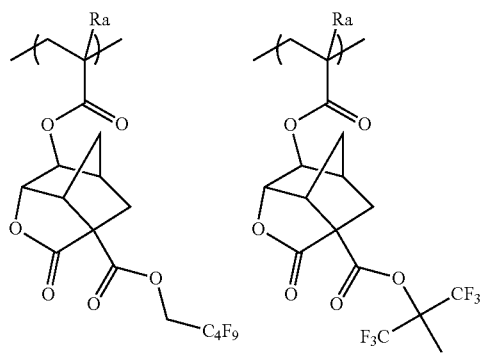

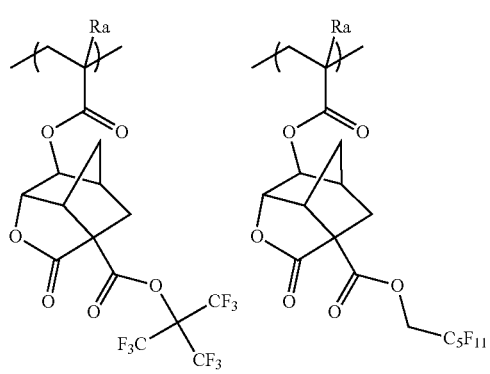

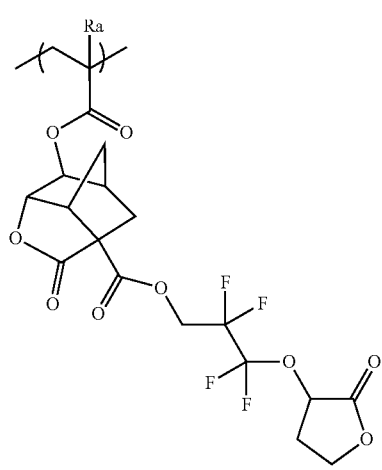

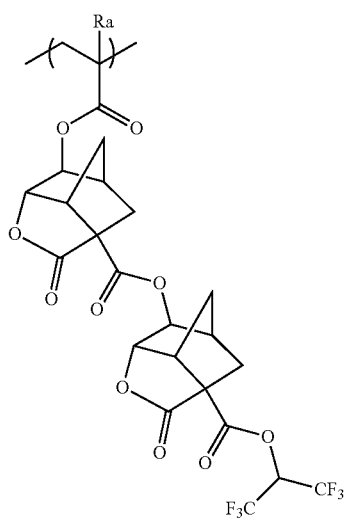
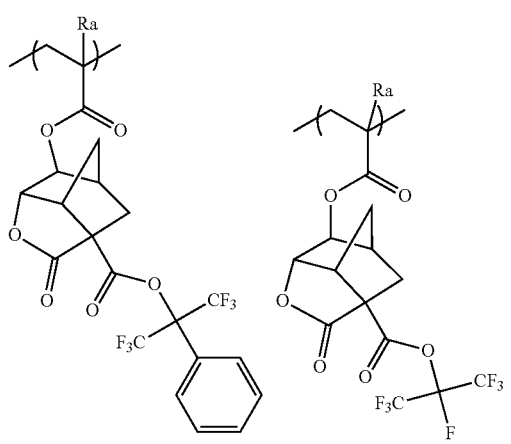
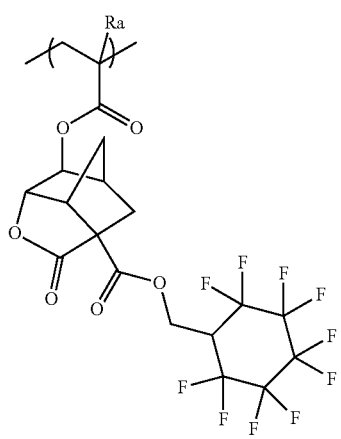
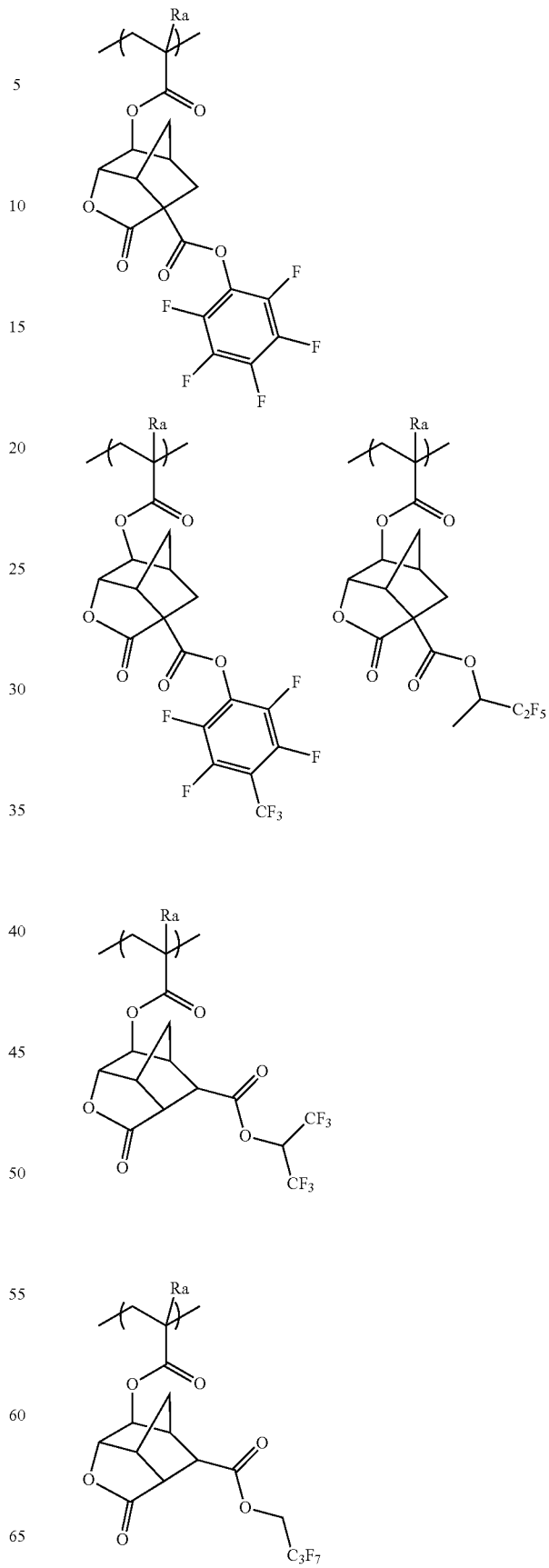

-continued
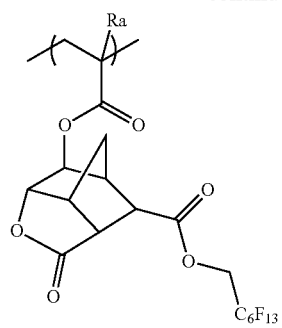
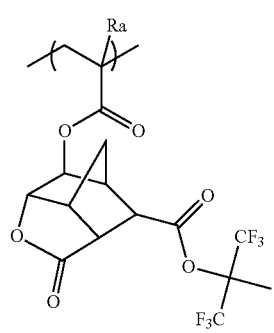
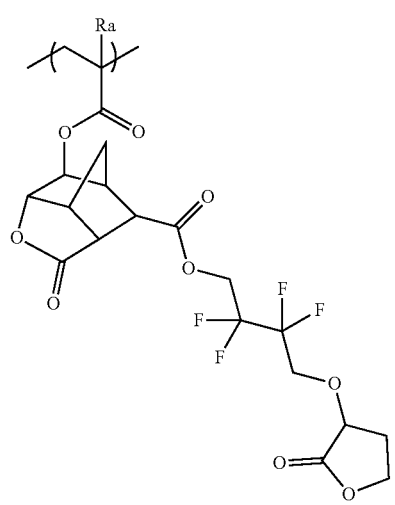
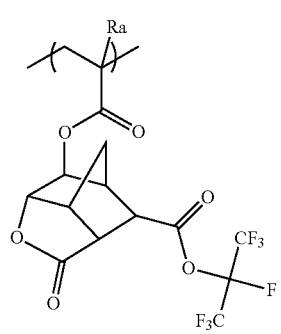
-continued
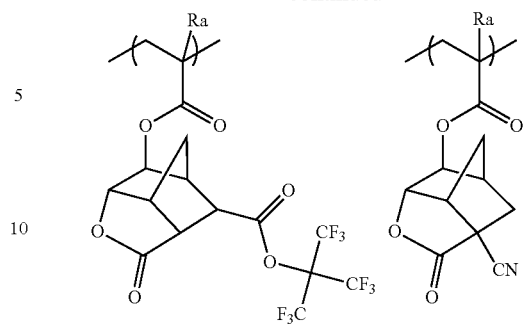
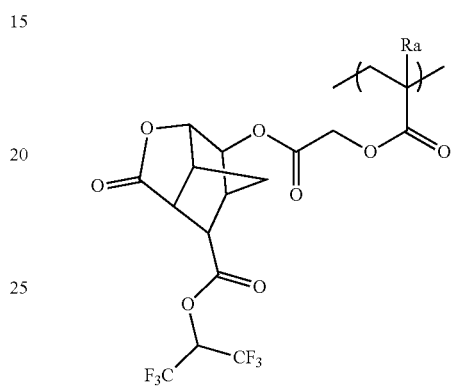
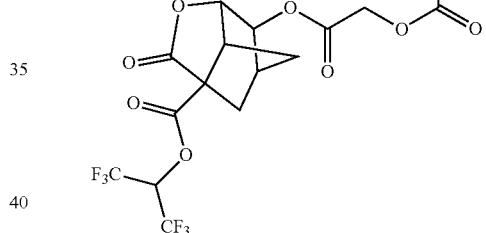
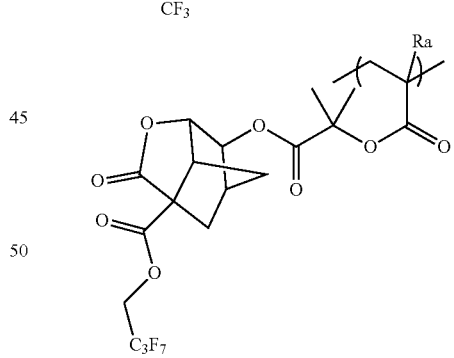
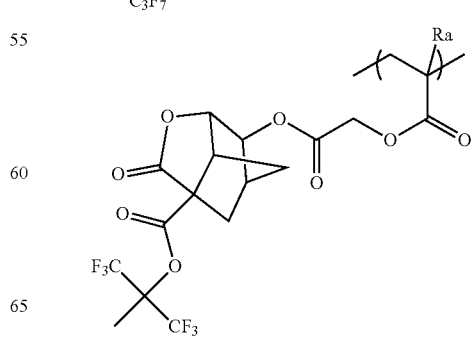

-continued
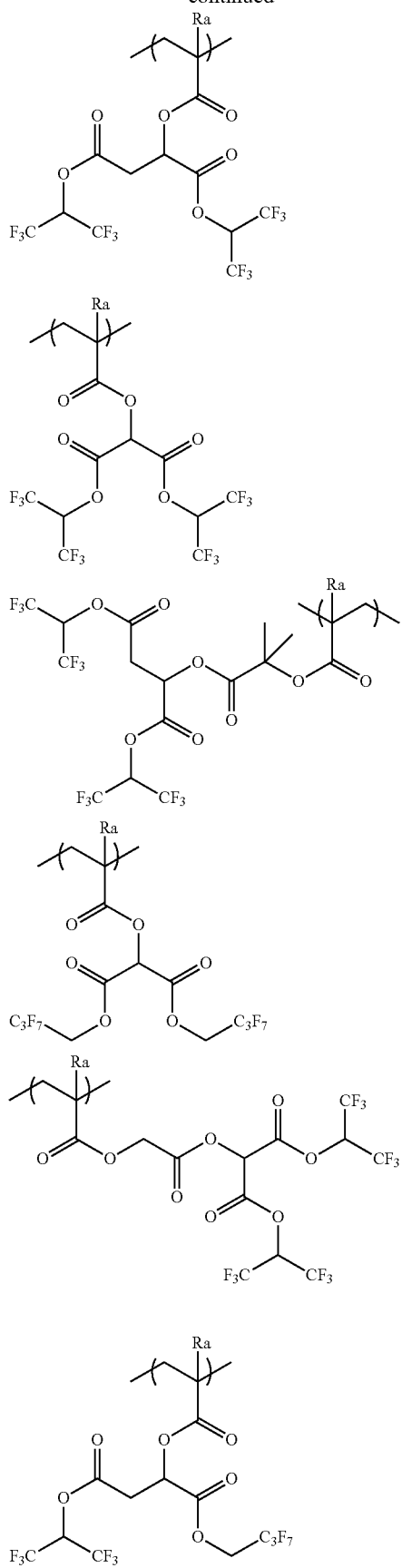
-continued
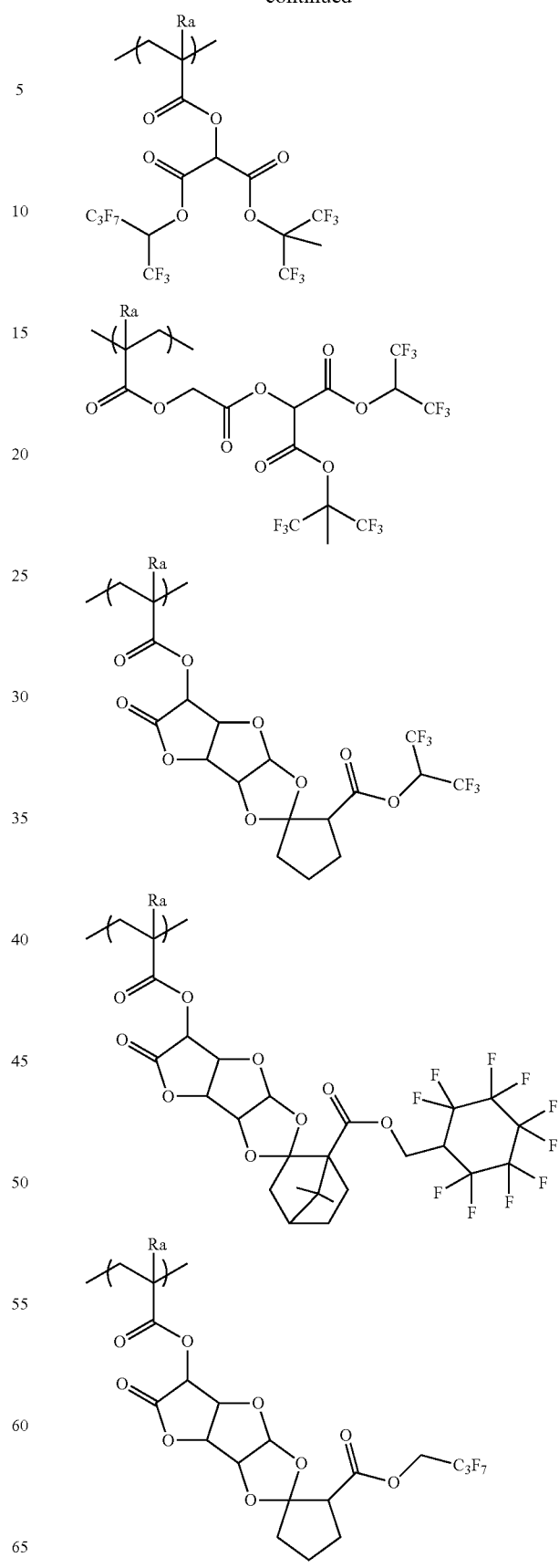

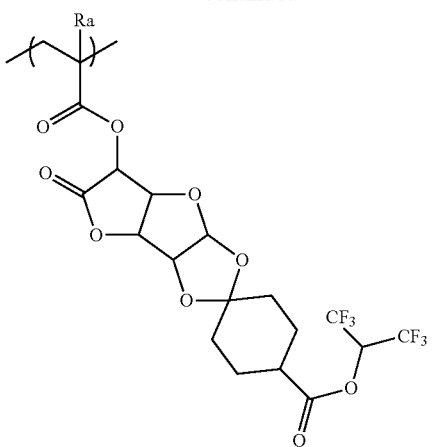

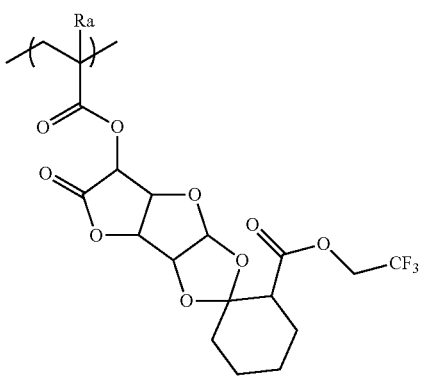

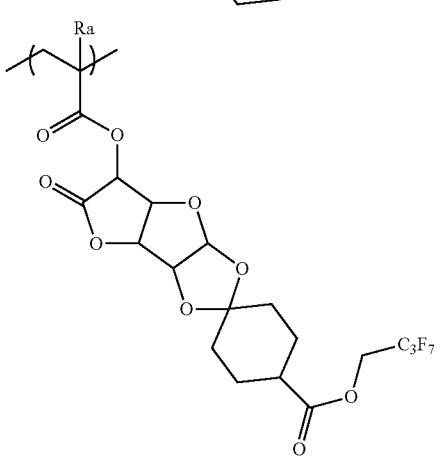

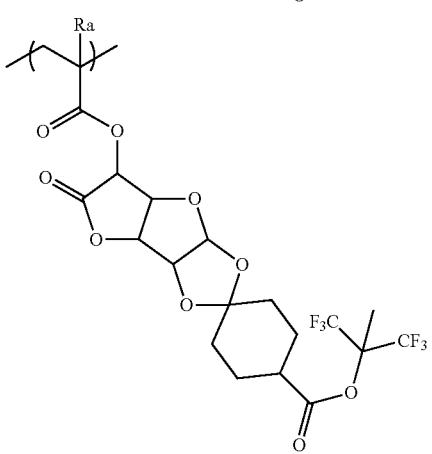

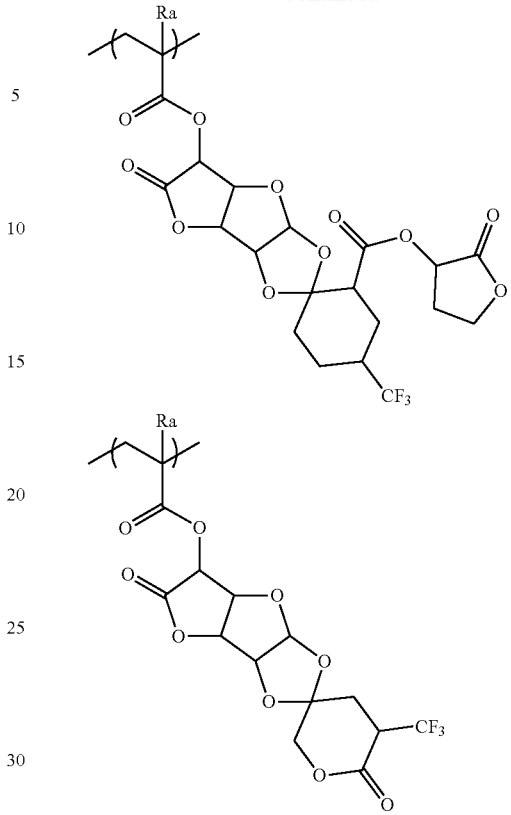

The content of the repeating unit (c) in the resin (C) is preferably 10% to 100% by mole, more preferably 20% to 100% by mole, still more preferably 30% to 100% by mole, and most preferably 40% to 100% by mole with respect to all the repeating units in the resin (C).

The content of the repeating unit (c') is preferably 10% to 100% by mole, more preferably 20% to 100% by mole, still more preferably 30% to 100% by mole, and most preferably 40% to 100% by mote with respect to alt the repeating units in the resin (C).

The content of the repeating unit (c*) is preferably 5% to 70% by mole, more preferably 5% to 60% by mole, still more preferably 10% to 50% by mole, and most preferably 10% to 40% by mole with respect to all the repeating units in the resin (C). The content of the repeating unit having a fluorine atom, which is used together with the repeating unit (c*), is preferably 10% to 95% by mole, more preferably 15% to 85% by mole, still more preferably 20% to 80% by mole, and most preferably 25% to 75% by mole with respect to ail the repeating units in the resin (C).

The content of the repeating unit (c") is preferably 10% to 100% by mole, more preferably 20% to 100% by mole, still more preferably 30% to 100% by mole, and most preferably 40% to 100% by mole with respect to all the repeating units (c") in the resin (C).

The fluorine atom in the resin (C) may be contained in the main chain of the resin or may be substituted in a side chain of the resin.

The resin (C) may further have another repeating unit. Preferred aspects of the other repeating units include the following ones.

(cy1) A repeating unit which has a fluorine atom, and is stable to an acid, and sparingly soluble or insoluble in an alkali developer.

(cy2) A repeating unit which has no fluorine atom, and is stable to an acid, and sparingly soluble or insoluble in an alkali developer.

(cy3) A repeating unit which has a fluorine atom and a polar group other than (x) and (z) described above.

(cy4) A repeating unit which has no fluorine atom and has a polar group other than (x) and (z) described above.

In the repeating units of (cy1) and (cy2), "being sparingly soluble or insoluble in an alkali developer" means that (cy1) and (cy2) do not include an alkali-soluble group or a group that produces an alkali-soluble group by the action of an acid or an alkali developer (for example, an acid-decomposable group or a polarity conversion group).

The repeating units (cy1) and (cy2) preferably have an alicyclic hydrocarbon structure having no polar group.

Preferred aspects of the repeating units (cy1) to (cy4) are shown below.

The repeating units (cy1) and (cy2) are each preferably a repeating unit represented by General Formula (CIII).

In General Formula (Oil), $R_{c31}$ represents a hydrogen atom, an alkyl group which may be substituted with a fluorine atom, a cyano group, or a —$CH_2$—O—$Rac_2$ group. In the formula, $Rac_2$ represents a hydrogen atom, an alkyl group, or an acyl group. $R_{c31}$ is preferably a hydrogen atom, a methyl group, a hydroxymethyl group, or a trifluoromethyl group, and particularly preferably the hydrogen atom or the methyl group.

$R_{c32}$ represents a group having an alkyl group, a cycloalkyl group, an alkenyl group, a cycloalkenyl group, or an aryl group. These groups may be substituted with a group including a silicon atom, a fluorine atom, or the like.

$L_{c3}$ represents a single bond or a divalent linking group.

In General Formula (CIII), the alkyl group of $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably a phenyl group having 6 to 20 carbon atoms or a naphthyl group, and these may have a substituent.

$R_{c32}$ is preferably an unsubstituted alkyl group or an alkyl group substituted with a fluorine atom. The divalent linking group of $L_{c3}$ is preferably an alkylene group (preferably having 1 to 5 carbon atoms), an oxy group, a phenylene group, or an ester bond (a group represented by —COO—).

The repeating units (cy1) and (cy2) are each preferably a repeating unit represented by General Formula (C4) or (C3).

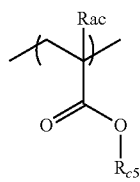

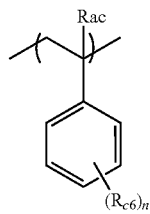

In General Formulae (C4) and (C5), $R_{c5}$ represents a hydrocarbon group which has at least one cyclic structure and has neither a hydroxyl group nor a cyano group.

Rac represents a hydrogen atom, an alkyl group which may be substituted with a fluorine atom, a cyano group, or a —$CH_2$—O—$Rac_2$ group. In the formula, $Rac_2$ represents a hydrogen atom, an alkyl group, or an acyl group. Rac is preferably the hydrogen atom, a methyl group, a hydroxymethyl group, or a trifluoromethyl group, and particularly preferably the hydrogen atom or the methyl group.

The cyclic structure contained in $R_{c5}$ includes a monocyclic hydrocarbon group and a polycyclic hydrocarbon group. Examples of the monocyclic hydrocarbon group include a cycloalkyl group having 3 to 12 carbon atoms and a cycloalkenyl group having 3 to 12 carbon atoms. A preferred monocyclic hydrocarbon group is a monocyclic hydrocarbon group having 3 to 7 carbon atoms.

Examples of the polycyclic hydrocarbon group include a ring-assembled hydrocarbon group and a crosslinked cyclic hydrocarbon group. Examples of the crosslinked cyclic hydrocarbon ring include a bicyclic hydrocarbon ring, a tricyclic hydrocarbon ring, and a tetracyclic hydrocarbon ring. Further, other examples of the crosslinked cyclic hydrocarbon ring include a fused cyclic hydrocarbon ring (for example, a fused ring formed by fusing a plurality of 5- to 8-membered cycloalkane rings). Preferred examples of the crosslinked cyclic hydrocarbon ring include a norbornyl group and an adamantyl group.

These alicyclic hydrocarbon groups may have a substituent, and preferred examples of the substituent include a halogen atom, an alkyl group, a hydroxyl group protected with a protective group, and an amino group protected with a protective group. Preferred examples of the halogen atom include bromine, chlorine, and fluorine atoms, and preferred examples of the alkyl group include methyl, ethyl, butyl, and t-butyl groups. The alkyl group may further have a substituent, and examples of the substituent which may further be contained include a halogen atom, an alkyl group, a hydroxyl group protected with a protective group, and an amino group protected with a protective group.

Examples of the protective group include an alkyl group, a cycloalkyl group, an aralkyl group, a substituted methyl group, a substituted ethyl group, an alkoxycarbonyl group, and an aralkyloxycarbonyl group. Preferred examples of the alkyl group include an alkyl group having 1 to 4 carbon atoms; preferred examples of the substituted methyl group include methoxymethyl, methoxythiomethyl, benzyloxymethyl, t-butoxymethyl, and 2-methoxyethoxymethyl groups; preferred examples of the substituted ethyl group include 1-ethoxyethyl and 1-methyl-1-methoxyethyl; preferred examples of the acyl group include an aliphatic acyl group having 1 to 6 carbon atoms, such as formyl, acetyl, propionyl, butyryl, isobutyryl, valeryl, and pivaloyl groups; and examples of the alkoxycarbonyl group include an alkoxycarbonyl group having 2 to 4 carbon atoms.

$R_{c6}$ represents an alkyl group, a cycloalkyl group, an alkenyl group, a cycloalkenyl group, an alkoxycarbonyl group, or an alkylcarbonyloxy group. These groups may be substituted with a fluorine atom or a silicon atom.

The alkyl group of $R_ce$ is preferably a linear or branched alkyl group having 1 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The alkoxycarbonyl group is preferably an alkoxycarbonyl group having 2 to 20 carbon atoms.

The alkylcarbonyloxy group is preferably an alkylcarbonyloxy group having 2 to 20 carbon atoms.

n represents an integer of 0 to 5. In a case where n is 2 or more, a plurality of Roe's may be the same as or different from each other.

$R_{c6}$ is preferably an unsubstituted alkyl group or an alkyl group substituted with, a fluorine atom, and particularly preferably a trifluoromethyl group or a t-butyl group.

It is also preferable that (cy1) and (cy2) are each a repeating unit represented by General Formula (CII-AB).

(CII-AB)

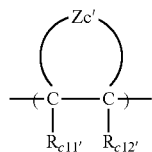

In Formula (CXI-AB), $R_{c11}'$ and $R_{c12}'$ each independently represent a hydrogen atom, a cyano group, a halogen atom, or an alkyl group.

Zc' represents an atomic group for forming an alicyclic structure, which includes two bonded carbon atoms (C—C).

Furthermore, General Formula (CII-AB) is more preferably General Formula (CII-AB1) or General Formula (CII-AB2).

CII-AB1

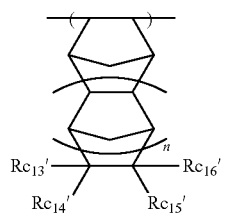

CII-AB2

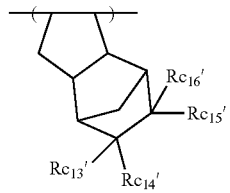

In Formulae (CII-AB1) and (CII-AB2), $Rc_{13}'$ to $Rc_{16}'$ each independently represent a hydrogen atom, a halogen atom, an alkyl group, or a cycloalkyl group.

Further, at least two of $Rc_{13}'$, or $Rc_{16}'$ may be bonded to each other to form a ring.

n represents 0 or 1.

Specific examples of (cy1) and (cy2) are shown below, but the present invention is not limited thereto. In the formulae, Ra represents H, $CH_3$, $CH_2OH$, $CF_3$, or CN.

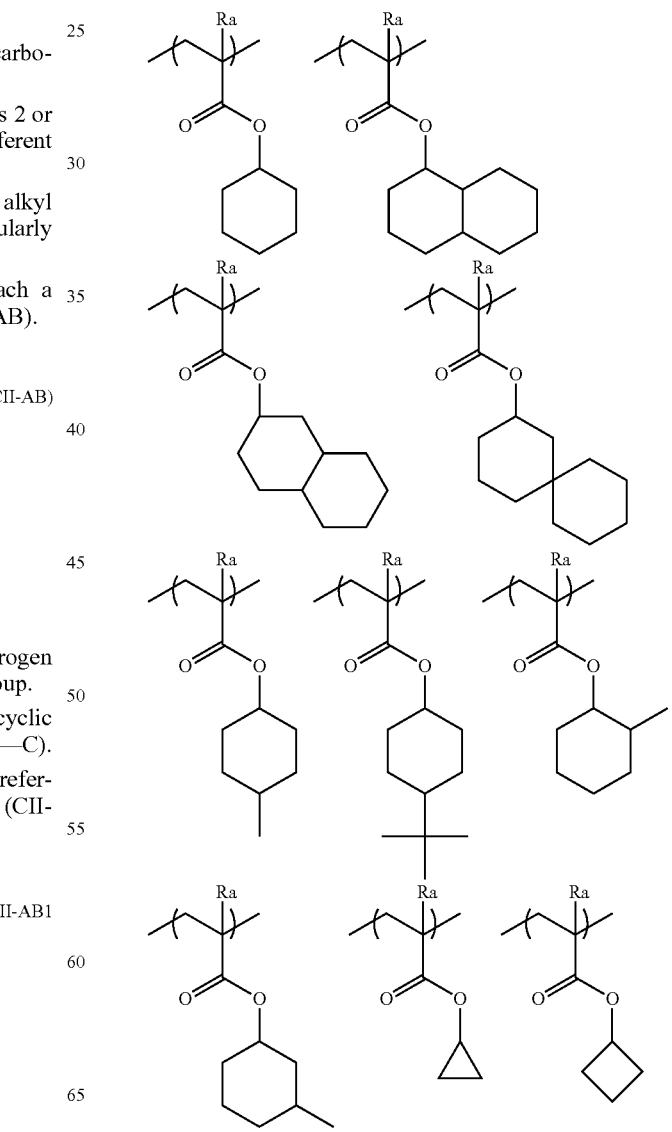

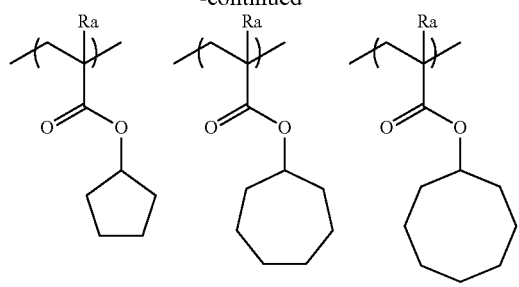
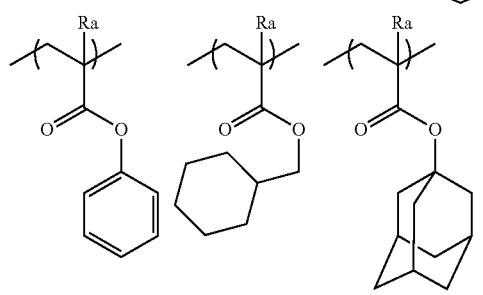
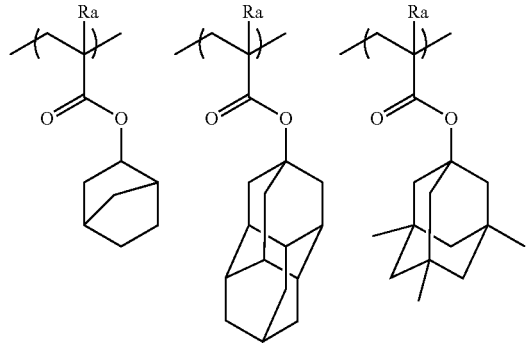
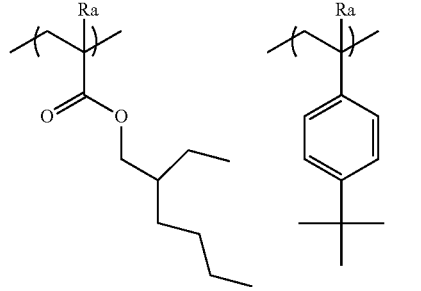
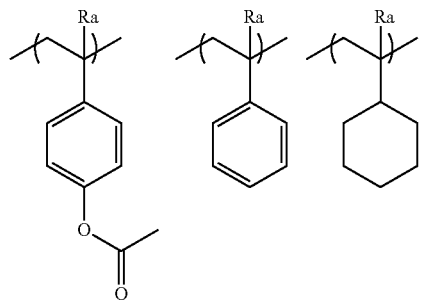
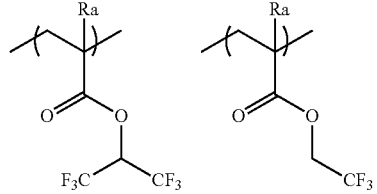

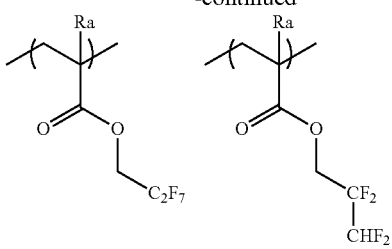
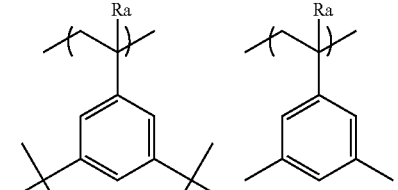
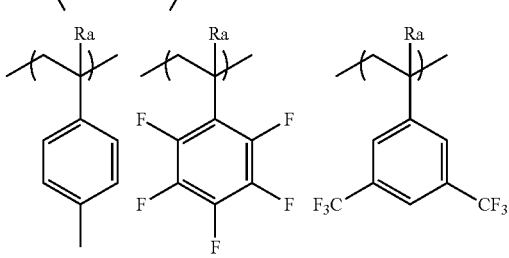
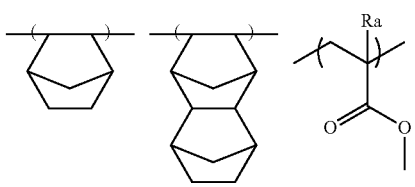
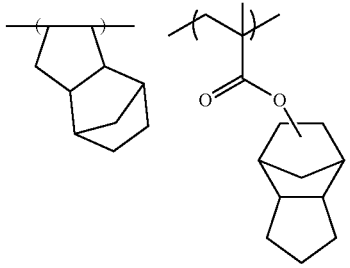

Each of (cy3) and (cy4) is preferably a repeating unit having a hydroxyl group or a cyano group as a polar group. This improves the affinity for the developer. The repeating unit having a hydroxyl group or a cyano group is preferably a repeating unit having an alicyclic hydrocarbon structure substituted with a hydroxyl group or a cyano group. In the alicyclic hydrocarbon structure substituted with a hydroxyl group or a cyano group, the alicyclic hydrocarbon structure is preferably an adamantyl group, a diamantyl group, or a norbornyl group. Preferred examples of the alicyclic hydrocarbon structure substituted with a hydroxyl group or a cyano group include a monohydroxyadamantyl group, a dihydroxyadamantyl group, a monohydroxydiadamantyl group, a dihydroxydiadamantyl group, and a norbornyl group substituted with a cyano group.

Examples of the repeating unit having the atomic group include repeating units represented, by General Formulae (CAIIa) to (CAIId).

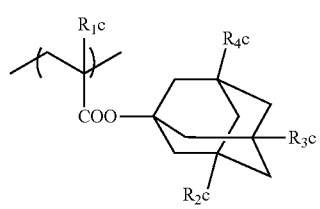 (CAIIa)

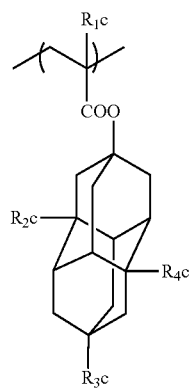 (CAIIb)

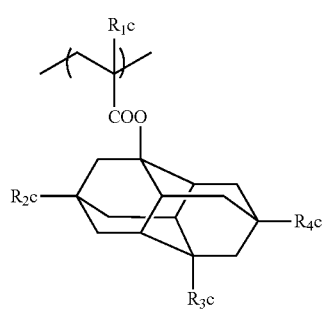 (CAIIc)

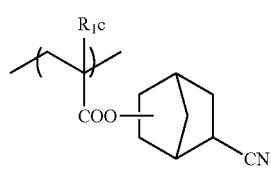 (CAIId)

In General Formulae (CAIIa) to (CAIId), $R_1c$ represents a hydrogen atom, a methyl group, a trifluoromethyl group, or a hydroxymethyl group.

$R_2c$ to $R_4c$ each independently represent a hydrogen atom, a hydroxyl group, or a cyano group. It should be noted that at least one of $R_2c$, or $R_4c$ represents a hydroxyl group or a cyano group. Preferably, one or two of $R_2c$ to $R_4c$ are hydroxyl groups, and the remaining is a hydrogen atom. In General Formula (CAIIa), it is more preferable that two of $R_2c$ to $R_4c$ are hydroxyl groups and the remaining is a hydrogen atom.

Specific examples of the repeating units represented by (cy3) and (cy4) are shown below, but the present invention is not limited thereto.

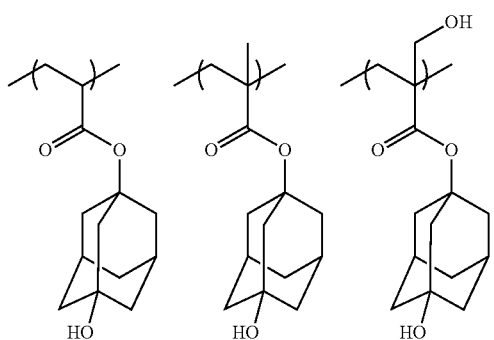

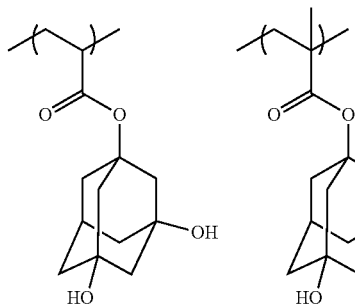

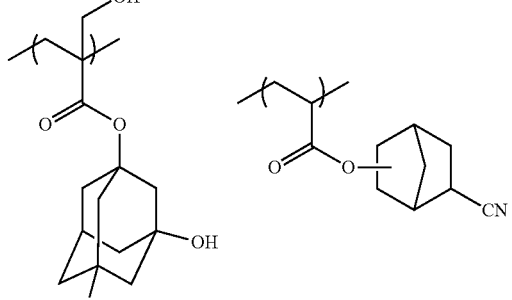

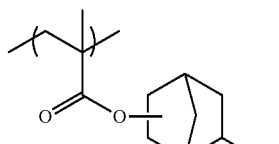

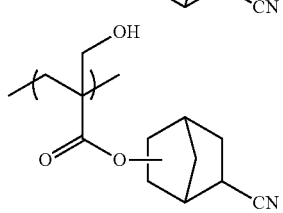

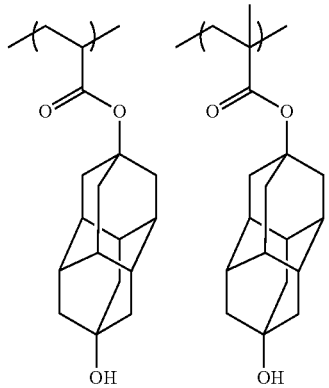

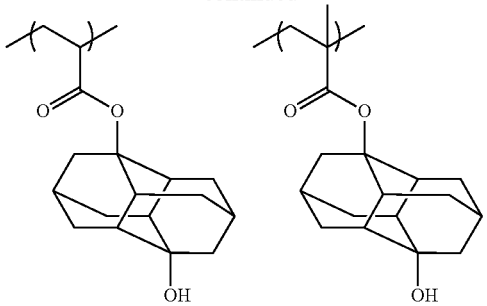

The content of the repeating units represented by (cy1) to (cy4) is preferably 5% to 40% by mole, more preferably 5% to 30% by mole, and still more preferably 10% to 25% by mole with respect to all the repeating units in the resin (C).

The resin (C) may have a plurality of repeating units represented by (cy1) to (cy4).

The content of fluorine atoms in the resin (C) is preferably 5% to 80% by mass, and more preferably 10% to 80% by mass, with respect to the molecular weight of the resin (C). Further, the repeating unit containing a fluorine atom is preferably 10% to 100% by mass, and more preferably 30% to 100% by mass with respect to all the repeating units in the resin (C).

From the viewpoint of improving the uneven distribution, the molecular weight of the fluorine-containing compound (C) is preferably 1,000 to 100,000.

The weight-average molecular weight of the resin (C) is preferably 1,000 to 100,000, more preferably 1,000 to 50,000, and still more preferably 2,000 to 15,000.

The molecular weight distribution (Mw/Mn, also referred to as a dispersity) of the resin (C) is preferably in the range of 1 to 3, more preferably 1 to 2, still more preferably 1 to 1.8, and most preferably in the range of 1 to 1.5.

As the resin (C), various commercially available products can be used, and in the same manner as the resin (A), the resin (C) can be synthesized according to an ordinary method (for example, radical polymerization).

The fluorine-containing compound (C) can be used alone or in combination of two or more kinds thereof.

From the viewpoint of resolution, the content of the fluorine-containing compound (C) in the composition of the embodiment of the present invention is preferably 0.01% to 10% by mass, more preferably 0.1% to 10% by mass, and still more preferably 0.1% to 5% by mass with respect to the total solid content of the composition of the embodiment of the present invention.

<Compound Having Lactone Structure or Sultone Structure>

The composition of the embodiment of the present invention preferably includes a compound having a lactone structure or a sultone structure.

Examples of the compound having a lactone structure or a sultone structure include a resin having a lactone group or a sultone group and a photoacid generator having a lactone group or a sultone group, each in the resin (A), <Solvent>

The composition of the embodiment of the present invention may include a solvent.

In the composition of the embodiment of the present invention, a known resist solvent can be appropriately used. For example, the known solvents disclosed in paragraphs <0665> to <0670> of the specification of US2016/0070167A1, paragraphs <0210> to <0235> of the specification of US2015/0004544A1, paragraphs <0424> to <0426> of the specification of US2016/0237190A1, and paragraphs <0357> to <G366> of the specification of US2016/0274458A1 can be suitably used.

Examples of the solvent which can be used in the preparation of the composition include organic solvents such as alkylene glycol monoalkyl ether carboxylate, alkylene glycol monoalkyl ether, alkyl lactic acid ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

As the organic solvent, a mixed solvent obtained by mixing a solvent having a hydroxyl group in the structure and a solvent having no hydroxyl group may be used.

As the solvent having a hydroxyl group and the solvent having no hydroxyl group, the above-exemplified compounds can be appropriately selected, but as the solvent having a hydroxyl group, alkylene glycol monoalkyl ether or alkyl lactate is preferable, and propylene glycol monomethyl ether (PGME), propylene glycol monoethyl ether (PGEE), methyl 2-hydroxyisobutyrate, or ethyl lactate is more preferable. Further, as the solvent having no hydroxyl group, alkylene glycol monoalkyl ether acetate, alkyl alkoxypropionate, a monoketone compound which may have a ring, a cyclic lactone, alkyl acetate, or the like is preferable, and among these, propylene glycol monomethyl ether acetate (PGMEA), ethyl ethoxypropionate, 2-heptanone, γ-butyrolactone, cyclohexanone, cyclopentanone, or butyl acetate is more preferable, and propylene glycol monomethyl ether acetate, γ-butyrolactone, ethyl ethoxypropionate, cyclohexanone, cyclopentanone, or 2-heptanone is still more preferable. As a solvent having no hydroxyl group, propylene carbonate is also preferable.

A mixing ratio (mass ratio) of the solvent having a hydroxyl group to the solvent having no hydroxyl group is preferably 1/99 to 99/1, more preferably 10/90 to 90/10, and still more preferably 20/80 to 60/40. A mixed solvent including 50% by mass or more of the solvent having no hydroxyl group is preferable from the viewpoint of coating evenness.

The solvent preferably includes propylene glycol monomethyl ether acetate. In this case, the solvent may be a single solvent of propylene glycol monomethyl ether acetate or a mixed solvent of two or more kinds including propylene glycol monomethyl ether acetate.

In addition, as a preferable form of the solvent that may be contained in the composition of the embodiment of the present invention, the solvent is ethyl lactate in which the ratio of one of the L-isomer or D-isomer of the optical isomer is 1% or more higher than that of the other (hereinafter also referred to as "ethyl lactate having an optical purity of 1% or more").

The ratio of one thereof represents a content ratio (mass ratio) of the L isomer or D isomer with respect to the total amount of ethyl lactate.

In the present invention, the ratio of the L isomer to the total amount of ethyl lactate may be 1% or more higher than the ratio of the D isomer to the total amount of ethyl lactate, and the ratio of the D isomer to the total amount of ethyl lactate may be 1% or more higher than the ratio of L isomer to the total amount of ethyl lactate.

The optical purity of ethyl lactate in the solvent is 1% or more, preferably 20% or more, and more preferably 50% or more.

The upper limit value of the optical purity of ethyl lactate in the solvent is not particularly limited, but is 100% or less, and typically 99% or less.

The optical purity can be measured by chiral gas chromatography (GC).

As ethyl lactate having an optical purity of 1% or more, a commercially available ethyl lactate can also be used, and ethyl lactate can be produced from a racemate of ethyl lactate using an enzyme.

In addition, it is also possible to produce ethyl lactate having an optical purity of 1% or more by producing lactic acid having a high optical purity using bacteria and subjecting the obtained lactic acid to ethyl esterification.

Moreover, with regard to ethyl lactate having an optical purity of 1% or more, as a method, for adjusting the optical purity, a commercially available product may be used as it is in a case where ethyl lactate having a desired optical purity is on the market, and ethyl lactate having a desired optical purity may be produced by the method or the like. In addition, ethyl lactate having a specific optical purity may also be mixed with ethyl lactate having a different optical purity (for example, a racemate of ethyl lactate having an optical purity of 0) to obtain ethyl lactate having a desired optical purity.

The solvent may include only ethyl lactate having an optical purity of 1% or more, and may also include a solvent other than ethyl lactate (hereinafter also referred to as "another solvent"), in addition to ethyl lactate having an optical purity of 1% or more.

Examples of such another solvent include organic solvents such as alkylene glycol monoalkyl ether carboxylate, alkylene glycol monoalkyl ether, alkyl lactic acid ester other than ethyl lactate, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

The content of ethyl lactate having an optical purity of 1% or more is preferably 10% by mass or more, more preferably 20% by mass or more, and still more preferably 50% by mass or more with respect to the total amount of the solvent.

<Surfactant>

The composition of the embodiment of the present invention may further include a surfactant. By containing the surfactant, in a case where an exposure light source at a wavelength of 250 nm or less, in particular, 220 nm or less is used, it is possible to form a pattern with good sensitivity and resolution and less adhesiveness and development defects.

It is particularly preferable to use a fluorine-based and/or silicon-based surfactant as the surfactant.

Examples of the fluorine- and/or silicon-based surfactants include the surfactants described in <0276> of US2008/0248425A. In addition, EFTOP EF301 or EF303 (manufactured by Shin-Akita Chemical Co., Ltd.); FLORAD FC430, 431, or 4430 (manufactured by Sumitomo 3M Inc.); MEGAFACE F171, F173, F176, F189, F113, FI 10, F177, F120, or R08 (manufactured by DIG Corporation), SURFLON S-382, SC101, 102, 103, 104, 105, or 106 (manufactured by Asahi Glass Co., Ltd.); TROYSOL S-366 (manufactured by Troy Chemical Corporation); GF-300 or GF-150 (manufactured by Toagosei Chemical Industry Co., Ltd.); SURFLON S-393 (manufactured by Seimi Chemical Co., Ltd.); EFTOP EF121, EF122A, EF122B, RF122C, EF125M, EF135M, EF351, EF352, EF801, EF802, or EF601 (manufactured by JEMCO Inc.); PF636, PF656, PF6320, or PF6520 (manufactured by OMNOVA Solutions Inc.); or FTX-204G, 208G, 218G, 230G, 204D, 208D, 212D, 218D, or 222D (manufactured by NEOS COMPANY LIMITED) may be used. In addition, a polysiloxane polymer, KP-341 (manufactured by Shin-Etsu Chemical Co., Ltd.), can also be used as the silicon-based surfactant.

Furthermore, the surfactant may be synthesized using a fluoroaliphatic compound produced by a telomerization method (also referred to as a telomer method) or an oligomerization method (also referred to as an oligomer method), in addition to the known surfactants as shown above. Specifically, a polymer including a fluoroaliphatic group derived from fluoroaliphatic compound may be used as the surfactant. The fluoroaliphatic compound can be synthesized in accordance with, the method described in JP2002-90991A.

In addition, another surfactant other than the fluorine-based and/or silicon-based surfactants, described in <0280> of US2008/0248425A, may also be used.

These surfactants may be used alone or in combination of two or more kinds thereof.

In a case where the composition of the embodiment of the present invention includes a surfactant, a content thereof is preferably 0.00001% to 2% by mass, more preferably 0.0001% to 2% by mass, and still more preferably 0.0005% to 1% by mass with respect to the total solid content of the composition.

<Other Additives>

The composition of the embodiment of the present invention can contain, in addition to the components described above, a carboxylic acid, an onium carboxylate salt, a dissolution inhibiting compound having a molecular weight of 3,000 or less described in Proceeding of SPIE, 2724,355 (1996) and the like, a dye, a plasticizer, a photosensitizer, a light absorber, an antioxidant, and the like as appropriate.

In particular, carboxylic acid can be preferably used for improving the performance. The carboxylic acid is preferably an aromatic carboxylic acid such as benzoic acid or naphthoic acid.

In a case where the composition of the embodiment of the present invention includes a carboxylic acid, the content of the carboxylic acid is preferably 0.01% to 10% by mass, more preferably 0.01% to 5% by mass, and still more preferably 0.01% to 3% by mass with respect to the total solid content of the composition.

The actinic ray-sensitive or radiation-sensitive resin composition of the embodiment of the present invention is used with a trim thickness of preferably 10 to 250 am, more preferably 20 to 200 nm, and still more preferably 30 to 100 nm, from the viewpoint of improving a resolving power. Such a film thickness can be obtained by setting the concentration of solid contents in the composition to an appropriate range to provide the composition with a suitable viscosity and improve the coating property and the film forming property.

The concentration of solid, contents of the actinic ray-sensitive or radiation-sensitive resin composition in the embodiment of the present invention is usually 1.0% to 10% by mass, preferably 2.0% to 5.7% by mass, and more preferably 2.0% to 5.3% by mass. By setting the concentration of solid contents to be the range, the resist solution can be uniformly applied onto a substrate.

The concentration of solid contents is a mass percentage of the mass of other components excluding the solvent with respect to the total mass of the actinic ray-sensitive or radiation-sensitive resin composition.

<Preparation Method>

The composition of the embodiment of the present invention is preferably used by dissolving the components in a predetermined organic solvent (preferably the mixed solvent), and filtering the solution through a filter and applying it onto a predetermined support (substrate).

The pore size of a fitter for use in filtration through the filter is preferably pore size of 0.1 µm or less, more preferably 0.05 µm or less, and still more preferably 0.03 µm or less. Further, in a case where the concentration of solid contents of the composition is high (for example, 25% by mass or more), the pore size of a filter used for filter filtration is preferably 3 µm or less, more preferably 0.5 µm or less, and still more preferably 0.3 µm or less. As the filter, a polytetrafluoroethylene-made, polyethylene-made, or nylon-made filter is preferable. In the filtration using a filter as shown in the specification of JP2002-62667A, circulatory filtration may be performed or the filtration may be performed by connection of a plurality of kinds of filters in series or in parallel. In addition, the composition may be filtered in plural times. Furthermore, the composition may be subjected to a deaeration treatment or the like before or after filtration using a filter.

<Uses>

The composition of the embodiment of the present invention relates to an actinic ray-sensitive or radiation-sensitive resin composition having properties which change by undergoing a reaction upon irradiation with actinic rays or radiation. More specifically, the composition of the embodiment of the present invention relates to an actinic ray-sensitive or radiation-sensitive resin composition which is used in a step of manufacturing a semiconductor such as an integrated circuit (IC), for the manufacture of a circuit board for a liquid crystal, a thermal head, or the like, the manufacture of a mold structure for imprinting, other photofabrication steps, or production of a planographic printing plate or an acid-curable composition. A pattern formed in the present invention can be used in an etching step, an ion implantation step, a bump electrode forming step, a rewiring forming step, a microelectromechanical system (MEMS), or the like.

[Actinic Ray-Sensitive or Radiation-Sensitive Film]

The present invention also relates to an actinic ray-sensitive or radiation-sensitive film (preferably a resist film) formed with the actinic ray-sensitive or radiation-sensitive composition of the embodiment of the present invention. Such a film is formed, for example, by applying the composition of the embodiment of the present invention onto a support such as a substrate. The thickness of this film is preferably 0.02 to 0.1 µm. As a method for applying the composition on the substrate, a suitable application method such as spin coating, roll coating, flow coating, dip coating, spray coating, and doctor coating is applied on a substrate, but the spin coating is preferable and the rotation speed is preferably 1,000 to 3,000 rotations per minute (rpm). The coating film is prebaked (PB) at 60° C. to 150° C. for 1 to 20 minutes, and preferably at 80° C. to 120° C. for 1 to 10 minutes to form a thin film.

For a material constituting a substrate to be processed and an outermost layer thereof, for example, in a case of a semiconductor wafer, a silicon wafer can be used, and examples of the material forming the outermost layer include Si, $SiO_2$, SiN, SiON, and TiN, WSi, BPSG, SOG, and an organic antireflection film.

Before forming the resist film, an antireflection film may be previously coated on the substrate.

As the antireflection film, any of an inorganic film type antireflection film such as titanium, titanium dioxide, titanium nitride, chromium oxide, carbon, and amorphous silicon, and an organic film type antireflection film formed of a light absorber and a polymer material can be used. Further, as the organic antireflection film, a commercially available organic antireflection film such as DUV30 series or DUV-40 series manufactured by Brewer Science Inc., or AR-2, AR-3, or AR-5 manufactured by Shipley Co., Ltd, can be used.

Moreover, in the pattern forming method of the embodiment of the present invention, a topcoat may be formed on the upper layer of the resist film. It is preferable that the topcoat is not mixed with the resist film and can be uniformly applied to the upper layer of the resist film.

The topcoat is not particularly limited, a topcoat known in the related art can be formed by a method known in the related art, and for example, the topcoat can be formed in accordance with the description in paragraphs 0072 to 0082 of JP2014-059543A.

For example, it is preferable that a topcoat containing a basic compound as described in JP2013-61648A is formed on a resist film.

In addition, the topcoat preferably includes a compound which includes at least one group or bond selected from the group consisting of an ether bond, a thioether bond, a hydroxyl group, a thiol group, a carbonyl bond, and an ester bond.

Furthermore, the topcoat preferably contains a resin. The resin which can be contained in the topcoat is not particularly limited, but the same resin as the hydrophobic resin which can be included in the actinic ray-sensitive or radiation-sensitive composition can be used.

With regard to the hydrophobic resin, reference can be made to the descriptions in <0017> to <0023> of JP2013-61647A (<0017> to <0023> of the corresponding US2013/244438A), and <0016> to <0165> of JP2014-56194A, the contents of which are incorporated herein by reference.

The topcoat preferably includes a resin containing a repeating unit having an aromatic ring.

By containing the repeating unit having an aromatic ring, a secondary electron-generating efficiency and an acid-generating efficiency from a compound that generates an acid with actinic rays or radiation increase, particularly upon irradiation with electron beams or EUV exposure, and thus, an effect of realizing high sensitivity and high resolution in the formation of a pattern can be expected.

In a case where the topcoat includes a plurality of resins, it is preferable that the topcoat includes at least one resin (XA) having a fluorine atom and/or a silicon atom. It is more preferable that the topcoat composition includes at least one resin (XA) having a fluorine atom and/or a silicon atom, and a resin (XB) having a content of a fluorine atom and/or silicon atom which is smaller than that of the resin (XA). As a result, in a case where a topcoat film is formed, the resin (XA) is unevenly distributed on a surface of the topcoat film, and thus, that it is possible to improve performance such as development characteristics and immersion liquid followability.

In addition, the topcoat may contain an acid generator and a crosslinking agent.

The topcoat is typically formed from a composition for forming a topcoat.

For the composition for forming a topcoat, it is preferable that the respective components are dissolved in a solvent and filtered using a filter. The filter is preferably made of polytetrafluoroethylene, polyethylene, or nylon, which has a pore size of 0.1 µm or less, more preferably 0.05 µm or less, and still more preferably 0.03 µm or less. Furthermore, in a case where the concentration of solid contents of the composition is high (for example, 25% by mass or more), the pore size of a filter used for filtration using a filter is preferably 3 µm or less, more preferably 0.5 µm or less, still more preferably 0.3 µm or less. The filter is preferably a polytetrafluoroethylene-made, polyethylene-made, or nylon-made filter. In the filtration using a filter as shown in the specification of JP2002-62667A, circulatory filtration may be performed or the filtration may be performed by connection of a plurality of kinds of filters in series or in parallel. In addition, the composition may be filtered in plural times. Furthermore, the composition may be subjected to a deaeration treatment or the like before or after filtration using a filter.

The composition for forming a topcoat preferably does not include impurities such as a metal. The content of the metal components included in these materials is preferably 10 parts per million (ppm) or less, more preferably 5 ppm or less, and still more preferably 1 ppm or less, and it is particularly preferable that substantially no metal component is included (below a detection limit of the measuring apparatus).

It is also preferable to partially or wholly subjecting the inside of a device used, in a producing step (a step for synthesizing a raw material, and the like) of a raw material (a resin, a photoacid generator, and the like) of a resist composition to a glass lining treatment so that a content of metal impurities of the resist composition is adjusted to be small (for example, on the order of ppm by mass). Such a method is described, for example, in The Chemical Daily, Dec. 21, 2017.

In a case where the exposure which will be described later is liquid immersion exposure, the topcoat is arranged between the resist film and the immersion liquid, and also functions as a layer which does not bring the resist film into direct contact with the immersion liquid. In this case, preferred characteristics required for the topcoat (composition for forming a topcoat) are coating suitability onto the resist film, transparency to radiation, particularly to light at 193 nm, and sparing solubility in an immersion liquid (preferably water). Further, it is preferable that the topcoat is not mixed with the resist film and can be uniformly applied onto a surface of the resist, film.

Moreover, in order to uniformly apply the composition for forming a topcoat onto a surface of the resist film while not dissolving the resist film, it is preferable that the composition for forming a topcoat contains a solvent in which the resist film is not dissolved. It is more preferable to use a solvent of a component different from a developer (organic developer) containing an organic solvent which will be described in detail later as the solvent in which the resist film is not dissolved.

A method for applying the composition for forming a topcoat is not particularly limited, and a spin coating method, a spray method, a roller coating method, a dip method, or the like which is known in the related art can be used.

The thickness of the topcoat is not particularly limited, but is usually 5 nm to 300 nm, preferably 10 nm to 300 nm, more preferably 20 nm to 200 nm, and still more preferably 30 nm to 100 nm, from the viewpoint of transparency to an exposure light source.

After forming the topcoat, the substrate is postbaked (PB) as necessary.

From the viewpoint of resolution, it is preferable that the refractive index of the topcoat is close to that of the resist film.

The topcoat is preferably insoluble in an immersion liquid, and more preferably insoluble in water. With regard to the receding contact angle of the topcoat, the receding contact angle (23° C.) of the immersion liquid with respect to the topcoat is preferably 50 to 100 degrees, and more preferably 80 to 100 degrees, from the viewpoint of immersion liquid followability.

In the liquid immersion exposure, from the viewpoint that the immersion liquid needs to move on a wafer following the movement of an exposure head that is scanning the wafer at a high speed and forming an exposure pattern, the contact angle of the immersion liquid with respect to the topcoat in a dynamic state is important, and in order to obtain better resist performance, it is preferable that the immersion liquid has a receding contact angle in the range.

During the release of the topcoat, an organic developer may be used, and another release agent may be separately used. As the release agent, a solvent hardly permeating the resist film is preferable. From the viewpoint that the release of the topcoat can be carried out at the same time as the development of the resist film, the topcoat is preferably releasable by an organic developer. The organic developer used for the release is not particularly limited as long as it makes it possible to dissolve and remove a less exposed area of the resist film.

From the viewpoint of the release with the organic developer, the dissolution rate of the topcoat in the organic developer is preferably 1 to 300 nm/sec, and more preferably 10 to 100 nm/sec.

Here, the dissolution rate of the topcoat in the organic developer is a film thickness decreasing rate in a case where the topcoat is exposed to a developer after film formation, and in the present invention, it is a rate in a case where the topcoat is dipped, in butyl acetate at 23° C.

An effect of reducing development defects after developing a resist film is accomplished by adjusting the dissolution rate of a topcoat in an organic developer to 1 nm/sec or more, and preferably 10 nm/sec or more. Further, by setting the dissolution rate to 300 nm/sec or less, and preferably 100 nm/sec, an effect that the line edge roughness of a pattern after the development of the resist film is improved is accomplished, possibly due to an effect of reducing the exposure unevenness during the liquid immersion exposure.

The topcoat may be removed using another known developer, for example, an aqueous alkali solution. Specific examples of the usable aqueous alkali solution include an aqueous tetramethylammonium hydroxide solution.

[Pattern Forming Method]

The present invention also relates to a pattern forming method including a resist film forming step of forming a resist film using the actinic ray-sensitive or radiation-sensitive resin composition of the embodiment of the present invention, an exposing step of exposing the resist film, and a developing step of developing the exposed resist film using a developer.

In the present invention, the exposure is preferably carried out using electron beams, an ArF excimer laser, or extreme ultraviolet rays, and more preferably electron beams or extreme ultraviolet rays.

For exposure (pattern forming step) on a resist film in the production of a precision integrated circuit element, first, irradiation with an ArF excimer laser, electron beams, or extreme ultraviolet rays (EUV) is preferably performed patternwise on the resist film of the present invention. In a case of the ArF excimer laser, the exposure dose is approximately 1 to 100 $mJ/cm^2$, preferably approximately 20 to 60 $mJ/cm^2$; in a case of the electron beams, the exposure dose is approximately 0.1 to 20 μC/cm², and preferably approximately 3 to 10 μC/cm²; and in a case of the extreme ultraviolet rays, the exposure dose is approximately 0.1 to 20 mJ/cm², and preferably approximately 3 to 15 mJ/cm².

Subsequently, post exposure baking (PEB) is performed on a hot plate, preferably at 60° C. to 150° C. for 5 seconds to 20 minutes, more preferably at 80° C. to 120° C. tor 15 seconds to 10 minutes, and still more preferably at 80° C. to 120° C. for 1 to 10 minutes, and then development, rinsing, and drying are performed to form a pattern. Here, the post exposure baking is appropriately adjusted depending on the acid decomposability of the repeating unit having an acid-decomposable group in the resin (A). In a ease where the acid decomposability is low, it is also preferable that the temperature for post exposure baking is 110° C. or higher and the heating time is 45 seconds or longer.

The developer is appropriately selected, but an alkali developer (typically an aqueous alkali solution) or a developer containing an organic solvent (also referred to as an organic developer) is preferably used, and the alkali developer is more preferably used. In a case where the developer is an aqueous alkali solution, development is performed with an aqueous alkali solution of tetramethylammonium hydroxide (TMAH), tetrabutylammonium hydroxide (TBAH), or the like at 0.1% to 5% by mass, and preferably 2% to 3% by mass for 0.1 to 3 minutes, and preferably 0.5 to 2 minutes by an ordinary method such as a dip method, a puddle method, a spray method, or the tike. An appropriate amount of an alcohol and/or a surfactant may be added to the alkali developer. Thus, in the formation of a negative tone pattern, the film in the unexposed area is dissolved and the exposed area is hardly dissolved in the developer; and in the formation of a positive tone pattern, the film in the exposed, area is dissolved and the film in the unexposed area is hardly dissolved in the developer, so that a desired pattern is formed on the substrate. Further, in the formation of a positive tone pattern, the upper part of the film (air interface side) in the unexposed area, in particular, a portion of the upper part of the film adjacent to the exposed area is dissolved and developed in the developer in the same manner as the exposed area, and thus, a rectangular or round cross-sectional shape with a slightly rounded upper part is formed.

In a case where the pattern forming method, of the embodiment of the present invention has a step of performing development using an alkali developer, as the alkali developer, for example, an aqueous alkali solution of inorganic alkalis such as sodium hydroxide, potassium hydroxide, sodium carbonate, sodium silicate, sodium metasilicate, and aqueous ammonia, primary amines such as ethyl amine and n-propylamine, secondary amines such as diethylamine and di-n-butylamine, tertiary amines such as triethylamine and methyldiethylamine, alcohol amines such as dimethylethanolamine and triethanolamine, tetraalkylammonium hydroxides such as tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, ethyltrimethylammonium hydroxide, butyltrimethylammonium hydroxide, methyl triamyl ammonium hydroxide, and dibutyldipentylammonium hydroxide, quaternary ammonium salts such as trimethylphenylammonium hydroxide, trimethylbenzylammonium hydroxide, triethylbenzylammonium hydroxide, and dimethylbis(2-hydroxytethyl)ammonium hydroxide, or cyclic amines such as pyrrole and piperidine can be used.

Furthermore, the aqueous alkali solution can be used after adding an appropriate amount of alcohols or a surfactant thereto.

The alkali concentration of the alkali developer is usually 0.1% to 20% by mass.

The pH of the alkali developer is usually 10.0 to 15.0.

In particular, a 2.38%-by-mass aqueous tetramethylammonium hydroxide solution is desirable.

Pure water may be used as the rinsing liquid in the rinse treatment performed after the alkali development, and an appropriate amount of a surfactant may be added to the pure water.

In addition, after the developing treatment or the rinsing treatment, a treatment of removing the developer or the rinsing liquid adhering to a pattern with a supercritical fluid can be performed.

In a case where the pattern forming method of the embodiment of the present invention has a step of performing development using a developer containing an organic solvent, as the developer in the step (hereinafter also referred to as an organic developer), a polar solvent such as a ketone-based solvent, an ester-based solvent, an alcohol-based solvent, an amide-based solvent, and an ether-based solvent, or a hydrocarbon-based solvent can be used.

In the present invention, the ester-based solvent is a solvent having an ester group in the molecule, the ketone-based solvent is a solvent having a ketone group in the molecule, the alcohol-based solvent is a solvent having an alcoholic hydroxyl group in the molecule, the amide-based solvent is a solvent having an amide group in the molecule, and the ether-based solvent is a solvent having an ether bond in the molecule. Among those, a solvent having a plurality of the functional groups in one molecule is also present, but in this case, it is applicable to any of solvent species including the functional group contained in the solvent.

For example, diethylene glycol monomethyl ether is applicable to any of the alcohol-based solvent and the ether-based solvent in the classification. In addition, the hydrocarbon-based solvent is a hydrocarbon-based solvent having no substituent.

In particular, a developer containing at least one solvent selected from the ketone-based solvent, the ester-based solvent, the alcohol-based solvent, or the ether-based, solvent is preferable.

It is preferable to use an ester-based solvent having 7 or more carbon atoms (preferably 7 to 14 carbon atoms, more preferably 7 to 12 carbon atoms, and still more preferably 7 to 10 carbon atoms), and 2 or less heteroatoms as the developer from the viewpoint that the swelling of the resist film can be suppressed.

The heteroatom of the ester-based solvent is an atom other than a carbon atom and a hydrogen atom, and examples thereof include an oxygen atom, a nitrogen atom, and a sulfur atom. The number of the heteroatoms is preferably 2 or less.

Preferred examples of the ester-based solvents having 7 or more carbon atoms and 2 or less heteroatoms include amyl acetate, isoamyl acetate, 2-methylbutyl acetate, 1-methylbutyl acetate, hexyl acetate, pentyl propionate, hexyl propionate, heptyl propionate, butyl butanoate, and isobutyl isobutanoate, and isoamyl acetate or isobutyl isobutanoate is particularly preferably used.

As the developer, a mixed solvent of the ester-based solvent and the hydrocarbon-based solvent or a mixed solvent of the ketone-based solvent and the hydrocarbon-based, solvent may be used instead of the ester-based solvent having 7 or more carbon atoms and having 2 or less heteroatoms as mentioned above. Also in this ease, it is effective in suppressing the swelling of the resist film.

In a case where the ester-based solvent and the hydrocarbon-based solvent are used in combination, it is preferable to use isoamyl acetate as the ester-based solvent. In addition, from the viewpoint of adjusting the solubility of the resist film, a saturated hydrocarbon-based solvent (for example, octane, nonane, decane, dodecane, undecane, and hexadecane) is preferably used as the hydrocarbon-based solvent.

Examples of the ketone-based solvent include 1-octanone, 2-octanone, 1-nonanone, 2-nonanone, acetone, 2-heptanone (methyl amyl ketone), 4-heptanone, I-hexanone, 2-hexanone, diisobutyl ketone, 2,5-dimethyl-4-hexanone, diisobutyl ketone, cyclohexanone, methylcyclohexanone, phenylacetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate, and diisobutyl ketone and 2,5-dimethyl-4-hexanone are particularly preferably used.

Examples of the ester-based solvent include methyl acetate, butyl acetate, ethyl acetate, isopropyl acetate, pentyl acetate, isoamyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, butyl butyrate, and methyl 2-hydroxyisobutyrate.

Examples of the alcohol-based solvent include alcohols such as methyl alcohol, ethyl alcohol, n-propyl alcohol, isopropyl alcohol, n-butyl alcohol, sec-butyl alcohol, 4-methyl-2-pentanol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol; and glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include anisole, dioxane, and tetrahydrofuran, in addition to the glycol ether-based solvents.

As the amide-based solvent, for example, N-methyl-2-pyrrolidone, N,N-dimethylacetamide, N,N-dimethylformamide, hexamethylphosphoric triamide, 1,3-dimethyl-2-imidazolidinone, or the like can be used.

Examples of the hydrocarbon-based solvent include aromatic hydrocarbon-based solvents such as toluene and xylene, and aliphatic hydrocarbon-based solvents such as pentane, hexane, octane, decane, and undecane.

In addition, the aliphatic hydrocarbon-based solvent which is a hydrocarbon-based solvent may be a mixture of compounds having the same number of carbon atoms but different structures. For example, in a ease where decane is used as the aliphatic hydrocarbon-based solvent, 2-methylnonane, 2,2-dimethyloctane, 4-ethyloctane, isooctane, or the like which is a compound having the same number of carbon atoms and different structures, may be included in the aliphatic hydrocarbon-based solvent.

In addition, only one kind or a plurality of kinds of the compounds as described above having the same number of carbon atoms and different structures may be included.

A plurality of the solvents may be mixed or the solvent may be used in admixture with a solvent other than those described above or water.

It should be noted that in order to fully exert the effects of the present invention, the moisture content of the developer as a whole is preferably less than 10% by mass, and the developer is more preferably substantially free of the moisture.

The concentration of the organic solvent (in a case of mixing a plurality of the organic solvents, a total thereof) in the organic developer is preferably 50% by mass or more, more preferably 50% to 100% by mass, still more preferably 85% to 100% by mass, even still more preferably 90% to 100% by mass, and particularly preferably 95% to 100% by mass. Most preferably, the organic solvent consists substantially only of an organic solvent. In addition, a case of consisting substantially only of an organic solvent includes a case of containing a trace amount of a surfactant, an antioxidant, a stabilizer, an antifoaming agent, or the like.

In particular, the organic developer is preferably a developer containing at least one organic solvent selected from the group consisting of a ketone-based solvent, an ester-based solvent, an alcohol-based solvent, an amide-based solvent, and an ether-based solvent.

The vapor pressure of the organic developer at 20° C. is preferably 5 kPa or less, more preferably 3 kPa or less, and particularly preferably 2 kPa or less. By setting the vapor pressure of the organic developer to 5 kPa or less, evaporation of the developer on the substrate or in the development cup is suppressed, the temperature uniformity in a wafer plane is improved, and as a result, the dimensional uniformity in the wafer plane is improved.

Specific examples of the organic developer having a vapor pressure of 5 kPa or less include ketone-based solvents such as 1-octanone, 2-octanone, 1-nonanone, 2-nonanone, 2-heptanone (methyl amyl ketone), 4-heptanone, 2-hexanone, diisobutyl ketone, cyclohexanone, methylcyclohexanone, phenylacetone, and methyl isobutyl ketone, ester-based, solvents such as butyl acetate, pentyl acetate, isoamyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, ethyl lactate, butyl lactate, and propyl lactate, alcohol-based solvents such as n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol, ether-based solvents such as tetrahydrofuran, amide-based solvents such as N-methyl-2-pyrrolidone, N,N-dimethylacetamide, and N,N-dimethylformamide, aromatic hydrocarbon-based solvents such as toluene and xylene, and aliphatic hydrocarbon-based solvents such as octane and decane.

Specific examples of the organic developer having a vapor pressure of 2 kPa or less, which is a particularly preferable range, include ketone-based solvents such as 1-octanone, 2-octanone, 1-nonanone, 2-nonanone, 2-heptanone, 4-heptanone, 2-hexanone, diisobutyl ketone, cyclohexanone, methylcyclohexanone, and phenylacetone, ester-based solvents such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate, and propyl lactate, alcohol-based solvents such as n-butyl alcohol, sec-butyl alcohol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol, amide-based solvents such as N-methyl-2-pyrrolidone, N,N-dimethylacetamide, and N,N-dimethylformamide, aromatic hydrocarbon-based solvents such as xylene, and aliphatic hydrocarbon-based solvents such as octane, decane, and undecane.

The organic developer may include a basic compound.

An appropriate amount of a surfactant can be added to the organic developer, as necessary.

The surfactant is not particularly limited, but, for example, an ionic or nonionic fluorine-based and/or silicon-based surfactant or the like can be used. Examples of such the fluorine- and/or silicon-based surfactant include the surfactants described in, for example, JP1987-36663A (JP-S62-36663A), JP1986-226746A (JP-S61-226746A), JP1986-226745A (JP-S61-226745A), JP1987-170950A (JP-S62-170950A), JP1988-34540A (JP-S63-34540A), JP1995-230165A (JP-H07-230165A), JP1996-62834A (JP-H08-62834A), JP1997-54432A (JP-H09-54432A), JP1997-5988A (JP-H09-5988A), U.S. Pat. Nos. 5,405,720A, 5,360, 692A, 5,529,881A, 5,296,330A, 5,436,098A, 5,576,143A, 5,294,511A, and 5,824,451A, and nonionic surfactants are preferable. The nonionic surfactant is not particularly limited, but it is more preferable to use a fluorine-based surfactant or a silicon-based surfactant.

The amount of the surfactant to be used is preferably 0.0001% to 2% by mass, more preferably 0,0001% to 1% by mass, and particularly preferably 0.0001% to 0.1% by mass with respect to the total amount of the developer.

As the developing method, for example, a method in which a substrate is dipped in a tank filled with a developer for a certain period of time (a dip method), a method in which development is performed by heaping a developer up onto the surface of a substrate by surface tension, and then leaving it to stand for a certain period of time (a puddle method), a method in which a developer is sprayed on the surface of a substrate (a spray method), a method in which a developer is continuously jetted onto a substrate rotating at a constant rate while scanning a developer jetting nozzle at a constant rate (a dynamic dispense method), or the like can be applied.

In a case where the various developing methods include a step of jetting a developer from developing nozzles of a developing device toward the resist film, the jetting pressure of the developer to be jetted (flow rate per unit area of the developer to be jetted) is preferably 2 mL/sec/mm$^2$ or less, more preferably 1.5 mL/sec/mm$^2$ or less, and still more preferably 1 mL/sec/mm$^2$ or less. There is no particular lower limit to the flow rate, but the lower limit is preferably 0.2 mL/sec/mm$^2$ or more in consideration of a throughput.

By setting the jetting pressure of the developer to be jetted within the range, it is possible to significantly reduce the pattern defects derived from resist residues after development.

Although the details of this mechanism are not clear, it is considered that by setting the jetting pressure to be in the range, the pressure applied to the resist film by the developer is likely to be reduced and the resist film/pattern is prevented from being scraped or broken carelessly.

In addition, the jetting pressure (mL/sec/mm$^2$) of the developer is a value at the outlet of the developing nozzle in the developing de vice.

Examples of the method of adjusting the jetting pressure of the developer include a method, of adjusting a jetting pressure with a pump or the like, and a method of changing a pressure by adjusting the pressure with a supply from a pressure tank.

Furthermore, after a step of performing development using a developer including an organic solvent, a step of stopping the development may be carried out while substituting the solvent with another solvent.

A step of performing washing using a rinsing liquid may be included after the step of performing development using a developer including an organic solvent, but from the viewpoint of a throughput (productivity), an amount of the rinsing liquid to be used, and the like, a step of performing washing using a rinsing liquid may not be included.

The rinsing liquid used in the rinsing step after the developing step using a developer including an organic solvent is not particularly limited as long as the rinsing liquid does not dissolve the resist pattern, and a solution including a common organic solvent can be used. As the rinsing liquid, a rinsing liquid containing at least one organic solvent selected from the group consisting of a hydrocarbon-based solvent, a ketone-based solvent, an ester-based solvent, an alcohol-based solvent, an amide-based solvent, and an ether-based solvent is preferably used.

Specific examples of the hydrocarbon-based solvent, the ketone-based solvent, the ester-based solvent, the alcohol-based solvent, the amide-based solvent, and the ether-based solvent include the same ones as those described, for the developer including an organic solvent, and in particular, suitable examples thereof include butyl acetate and methyl isobutyl carbinol.

It is preferable to perform a step of performing washing, more preferably using a rinsing liquid containing at least one organic solvent selected from the group consisting of an ester-based solvent, an alcohol-based solvent, and a hydrocarbon-based solvent, and still more preferably using a rinsing liquid containing the alcohol-based solvent or the hydrocarbon-based solvent, after the step of performing development using a developer including an organic solvent.

Among the organic solvents, the hydrocarbon-based solvent is also preferably used, and the aliphatic hydrocarbon-based solvent is more preferably used, as the organic solvent included in the rinsing liquid. As the aliphatic hydrocarbon-based solvent used in the rinsing liquid, from the viewpoint of further improving the effects, an aliphatic hydrocarbon-based solvent having 5 or more carbon atoms (for example, pentane, hexane, octane, decane, undecane, dodecane, and hexadecane) is preferable, an aliphatic hydrocarbon-based solvent having 8 or more carbon atoms is more preferable, and an aliphatic hydrocarbon-based solvent having 10 or more carbon atoms is still more preferable.

Incidentally, the upper limit value of the number of carbon atoms in the aliphatic hydrocarbon-based solvent is not particularly limited, and for example, is 16 or less, preferably 14 or less, and more preferably 12 or less.

Among the aliphatic hydrocarbon-based solvents, decane, undecane, or dodecane is particularly preferable, and undecane is the most preferable.

By using the hydrocarbon-based, solvent (in particular, the aliphatic hydrocarbon-based solvent) as the organic solvent included in the rinsing liquid as described above, the developer permeating into the resist film slightly after development is washed away, the swelling is further suppressed, and thus, an effect of suppressing pattern collapse is farther exhibited.

The respective components in a plural number may be mixed or the components may also be used in admixture with an organic solvent other than the solvents.

The moisture content of the rinsing liquid is preferably 10% by mass or less, more preferably 5% by mass or less, and particularly preferably 3% by mass or less. By setting the moisture content to 10% by mass or less, good development characteristics can be obtained.

The vapor pressure at 20° C. of the rinsing liquid which is used after the step of performing development using a developer including an organic solvent is preferably from 0.05 kPa to 5 kPa, more preferably from 0.1 kPa to 5 kPa, and most preferably from 0.12 kPa to 3 kPa. By setting the vapor pressure of the rinsing liquid to be from 0.05 kPa to 5 kPa, the temperature uniformity in a wafer plane is improved, and further, the dimensional uniformity in a wafer plane is enhanced by suppression of swelling due to the permeation of the rinsing liquid.

The rinsing liquid can be used after an appropriate amount of a surfactant is added thereto.

In the rinsing step, a wafer which has been developed using a developer including an organic solvent is subjected to a washing treatment using a rinsing liquid including an organic solvent. A method for the washing treatment is not particularly limited, for example, a method in which a rinsing liquid is continuously jetted on a substrate rotating at a constant rate (a rotation application method), a method in which a substrate is dipped in a tank filled with a rinsing liquid for a certain period of time (a dip method), a method in which a rinsing liquid is sprayed on a substrate surface (a spray method), or the like, and among these, a method in which a washing treatment is performed using the rotation application method, and a substrate is rotated at a rotation speed of 2,000 rpm to 4,000 rpm after washing, thereby removing the rinsing liquid from the substrate, is preferable. Further, it is also preferable that a heating step (postbaking) is included after the rinsing step. The developer and the rinsing liquid remaining between and inside the patterns are removed by the baking. The heating step after the rinsing step is performed, usually at 40° C. to 160° C., and preferably 70° C. to 95° C., usually for 10 seconds to 3 minutes, and preferably for 30 seconds to 90 seconds.

In a case where there is no step of performing washing with a rinsing liquid, for example, the development treatment method described in paragraphs [0014] to [0086] of JP2015-216403A can be adopted.

Moreover, the pattern forming method of the embodiment of the present invention may include a developing step using an organic developer and a developing step using an alkali developer. A portion having a low exposure intensity is removed by development using an organic developer, and a portion having a high exposure intensity is removed by performing development using an alkali developer. By virtue of multiple development processes in which development is performed in a plurality of times in such a manner, a pattern can be formed by keeping only a region with an intermediate exposure intensity from not being dissolved, so that a finer pattern than usual can be formed (the same mechanism as in paragraph <0077> of JP2008-292975A).

It is preferable that various materials (for example, a resist solvent, a developer, a rinsing liquid, a composition for forming an antireflection film, and a composition for forming a topcoat) used in the actinic ray-sensitive or radiation-sensitive composition in the embodiment of the present invention, and the pattern forming method of the embodiment of the present invention include no impurities such as metals, metal salts including halogen, acids, alkalis, and components including a sulfur atom or a phosphorus atom. Here, examples of the impurities including a metal atom include Na, K, Ca, Fe, Cu, Mn, Mg, Al, Cr, Ni, Zn, Ag, Sn, Pb, Li, and salts thereof.

The content of the impurities included in these materials is preferably 1 ppm or less, more preferably 1 part per billion (ppb) or less, still more preferably 100 parts per trillion (ppt) or less, and particularly preferably 10 ppt or less, and it is the most preferable that the impurities are not substantially included (no higher than a detection limit of a measuring apparatus).

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a filter made of polytetrafluoroethylene, polyethylene, nylon, or the like is preferable. The filter may be a composite material in which these materials are combined with an ion exchange medium. As the filter, a filter which has been washed with an organic solvent in advance may be used. In the step of filtration using a filter, plural kinds of filters connected in series or in parallel may be used. In a case of using a plurality of kinds of filters, a combination of filters having different pore diameters and/or materials may be used. In addition, various materials may be filtered plural times, and the step of filtering plural times may be a circulatory filtration step.

In addition, examples of a method for reducing the impurities such as metals included in various materials include a method in which a raw material having a low metal content is selected as a raw material constituting various materials and the raw material constituting the various materials is subjected to filtration using a filter; and a method in which distillation under conditions suppressing contamination as much as possible by performing a lining with TEFLON (registered trademark), or the like in the inside of a device is performed. Preferred, conditions for the filtration using a filter performed on the raw materials constituting various materials are the same ones as the above-mentioned conditions.

In addition to the filtration using a filter, removal of impurities by an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used.

In addition, as a method for reducing the impurities such as metals included in the organic treatment liquid of the present invention, a method in which a raw material having a low metal content is selected as a raw material constituting various materials, the raw material constituting the various materials is subjected to filtration using a filter; distillation under conditions suppressing contamination as much as possible by performing a lining with TEFLON (registered trademark) in the inside of a device; or the like. Preferred conditions for the filtration using a filter performed on the raw materials constituting various materials are the same ones as the above-mentioned conditions.

In addition to the filtration using a filter, removal of impurities by an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used.

[Storage Container]

As an organic solvent (also referred to as an "organic treatment liquid") which can be used for a developer and a rinsing liquid, it is preferable to use one stored in a storage container for storing an organic treatment liquid for patterning a chemically amplified or non-chemically amplified resist film, in which the container has a storage part. The storage container is preferably, for example, a storage container for storing an organic treatment liquid for patterning a resist film, in which the inner wall of the storage part being in contact with the organic treatment liquid is formed from a resin different from any of a polyethylene resin, a polypropylene resin, and a polyethylene-polypropylene resin, or of a metal subjected to a rust prevention/metal elution prevention treatment. An organic solvent to be used as an organic treatment liquid for patterning a resist film is stored in the storage part of the storage container, and the organic solvent jetted from the storage part can be used at the time of patterning the resist film.

In a case where the storage container further has a sealing part for sealing the storage part, the sealing part is also preferably formed of a resin different from one or more resins selected from the group consisting of a polyethylene resin, a polypropylene resin, and a polyethylene-polypropylene resin, or of a metal which has been subjected to a rust prevention/metal elution prevention treatment.

Here, the sealing part refers to a member capable of shielding the storage part from the outside air, and suitable examples thereof include a packing and an O ring.

The resin different from one or more resins selected from the group consisting of a polyethylene resin, a polypropylene resin, and a polyethylene-polypropylene resin is preferably a perfluoro resin.

Examples of the perfluoro resin include a tetrafluoroethylene resin (PTFE), a tetrafluoroethylene-perfluoroalkyl vinyl ether copolymer (PFA), a tetrafluoroethylene-hexafluoropropylene copolymer resin (FEP), a tetrafluoroethylene-ethylene copolymer resin (ETFE), a trifluoroethylene chloride-ethylene copolymer resin (ECTFE), a polyvinylidene fluoride resin (PVDF), a trifluoroethylene chloride resin (PCTFE), and a polyvinyl fluoride resin (PVF).

Particularly preferred examples of the perfluoro resin include a tetrafluoroethylene resin, a tetrafluoroethylene-perfluoroalkyl vinyl ether copolymer, and a tetrafluoroethylene-hexafluoropropylene copolymer resin.

Examples of the metal in the metal which has been subjected to a rust prevention/metal elution prevention treatment include carbon steel, alloy steel, nickel chromium steel, nickel chromium molybdenum steel, chromium steel, chromium molybdenum steel, and manganese steel.

As the rust prevention/metal elution prevention treatment, a coating technique is preferably applied.

The coating technique is roughly divided into three types of metal coating (various plating), inorganic coating (various chemical conversion treatments, glass, concrete, ceramics, and the like), and organic coating (a rust preventive oil, a paint, rubber, and plastics).

Preferred examples of the coating technique include a rust preventive oil, a rust inhibitor, a corrosion inhibitor, a chelate compound, a strippable plastic, and a surface treatment with a lining agent.

Among those, corrosion inhibitors, such as various chromates, nitrites, silicates, phosphates, oleic acid, dimer acid, carboxylic acids such as naphthenic acid, carboxylic acid, metal soaps, sulfonates, amine salts, and esters (glycerine esters of higher fatty acids and phosphoric acid esters), chelate compounds such as ethylene diamine tetraacetic acid, gluconic acid, nitrilotriacetic acid, hydroxyethyl ethylene diamine triacetic acid, and diethylene triamine pentaacetic acid, and a fluorine resin lining are preferable. A phosphate treatment and the fluorine resin lining are particularly preferable.

Although it does not directly prevent rust as compared with, a direct coating treatment, it is also preferable to adopt a "pretreatment" which is a step prior to a rust prevention treatment, as a treatment method leading to prolongation of the rust prevention period by a coating treatment.

As a specific example of such a pretreatment, a treatment for removing a variety of corrosive factors such as chlorides and sulfates present on the metal surface by washing or polishing can be suitably mentioned.

Specific examples of the storage container include the following ones.

FluoroPureFFA composite drum manufactured by Entegris Inc. (wetted inner surface; PFA resin lining)

Steel drum manufactured by JFE Corporation (wetted inner surface; zinc phosphate-coated film)

Furthermore, examples of the storage container which can be used in the present invention include the containers described in paragraphs <0013> to <0030> of JP1999-021393A (JP-H11-021393A) and paragraphs <0012> to <0024> of JP1998-45961A (JP-H10-45961A).

In order to prevent breakdown of a chemical liquid pipe and various parts (a filter, an O-ring, a tube, and the like) due to electrostatic charging and subsequent electrostatic discharging, a conductive compound may be added to the organic treatment liquid of the present invention. The conductive compound is not particularly limited, but examples thereof include methanol. The addition amount of the conductive compound is not particularly limited, but is preferably 10% by mass or less, and more preferably 5% by mass or less from the viewpoint of maintaining preferable development characteristics. With regard to the members of the chemical liquid pipe, it is possible to use various pipes coated with stainless steel (SUS), or a polyethylene resin, a polypropylene resin, or a fluorine resin (a polytetrafluoroethylene resin, a perfluoroalkoxy resin, or the like), which has been subjected to an antistatic treatment. Similarly, a polyethylene resin, a polypropylene resin, or a fluorine resin (a polytetrafluoroethylene resin, a perfluoroalkoxy resin, or the like), which has been subjected to an antistatic treatment, can be used for a filter and an O-ring.

Moreover, generally, the developer and the rinsing liquid are stored in a waste liquid tank through a pipe after use. At that time, in a case where a hydrocarbon-based solvent is used as the rinsing liquid, there is a method of passing a solvent in which a resist is dissolved through a pipe again in order to prevent the resist dissolved in the developer from being precipitated and adhering to the back surface of the wafer, the side surface of the pipe or the like. Examples of the method of passing the solvent through the pipe include a method in which the back surface, the side surface, and the like of a substrate are washed with a solvent in which a resist is dissolved and then the solvent is allowed to flow after performing washing with a rinsing liquid, and a method of flowing a solvent in which a resist is dissolved so as to pass through a pipe while being not in contact with the resist.

The solvent to be passed through the pipe is not particularly limited as long as it can dissolve the resist, examples thereof include the above-mentioned organic solvents, and propylene glycol monomethyl ether acetate (PGMEA), propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate, ethylene glycol monoethyl ether acetate, propylene glycol monomethyl ether (PGME), propylene glycol monoethyl ether, propylene glycol monopropyl ether, propylene glycol monobutyl ether, ethylene glycol monomethyl ether, ethylene glycol monoethyl ether, 2-heptanone, ethyl lactate, 1-propanol, acetone, or the like can be used. Among those, PGMEA, PGME, or cyclohexanone can be preferably used,

[Photo Mask]

Furthermore, the present invention also relates to a photo mask manufactured using the above-described pattern forming method. The photo mask manufactured using the above-described, pattern forming method may be a light transmission type mask used in an ArF excimer laser or the like, or may be a light reflective type mask used in reflective lithography using EUV as a light source.

[Method for Manufacturing Electronic Device]

In addition, the present invention further relates to a method for manufacturing an electronic device, including the above-described pattern forming method. The electronic device manufactured by the method for manufacturing an electronic device of an embodiment of the present invention is suitably mounted on electric or electronic equipment (for example, home electronics, office automation (OA)-related, equipment, media-related equipment, optical equipment, and telecommunication equipment).

EXAMPLES

Hereinbelow, the present invention will be described in more detail with reference to Examples. The materials, the amounts of materials used, the proportions, the treatment details, the treatment procedure, and the like shown in Examples below may be appropriately modified as long as the modifications do not depart from the spirit of the present invention. Therefore, the scope of the present invention should not be construed as being limited to Examples shown below.

<Acid Diffusion Control Agent>

The structures of the acid diffusion control agents used are shown below, (q-1)

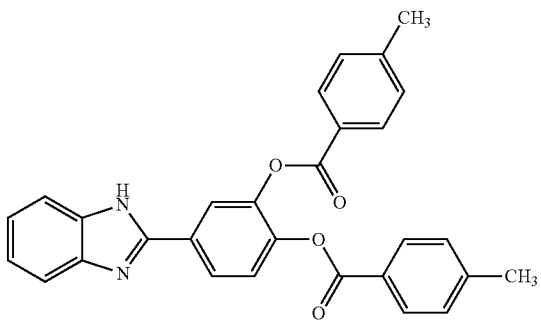

(q-2)

(q-3)

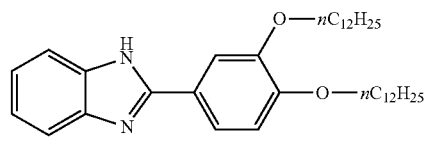

(q-4)

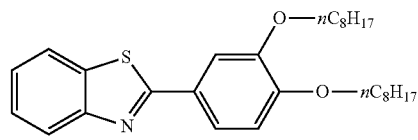

(q-5)

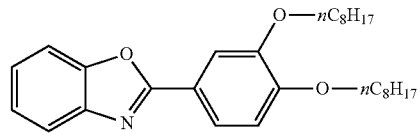

(q-6)

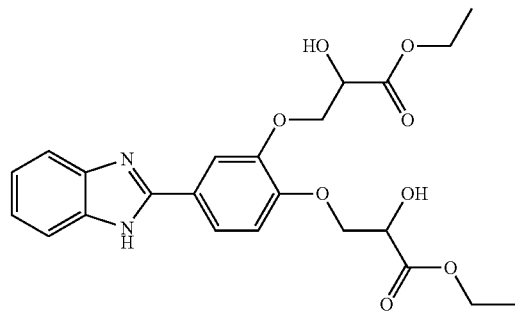

(q-7)

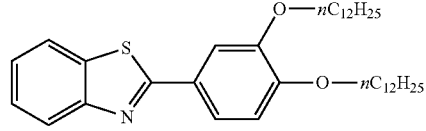

(q-8)

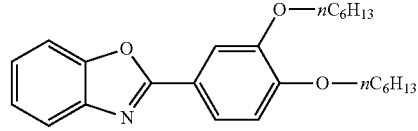

-continued

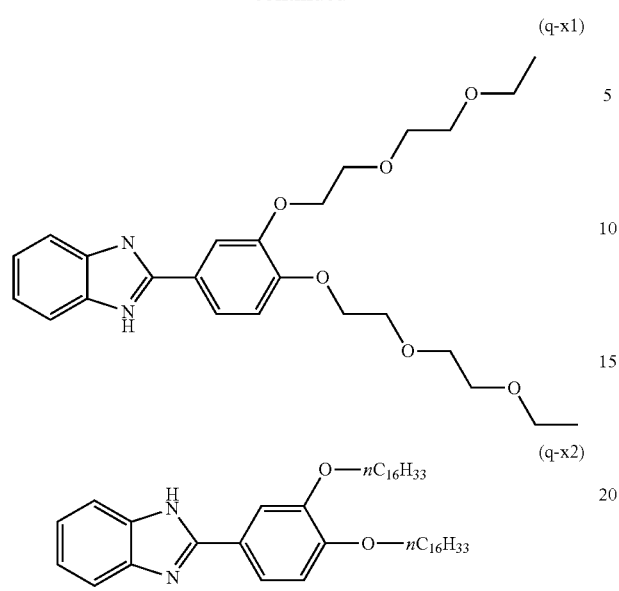

<Resin (A)>

The resins a-1 to a-3 used are shown below. The structure of the repeating unit and a content (molar ratio) thereof, a weight-average molecular weight (Mw), and a dispersity (Mw/Mn) of each resin are also shown.

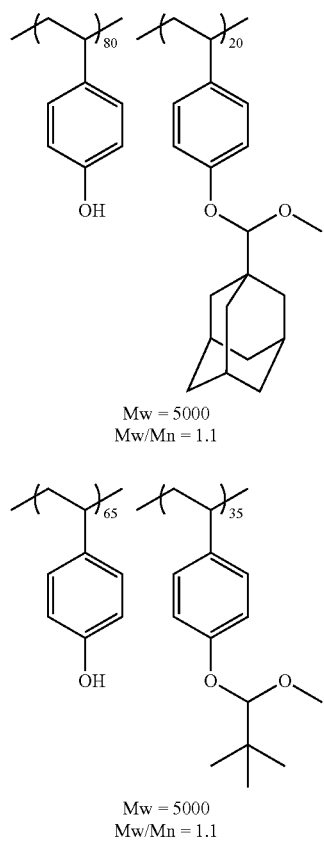

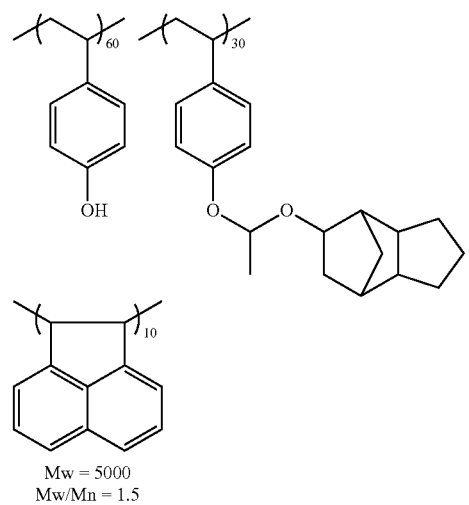

<Photoacid Generator>

The structures of the photoacid generators used are shown below.

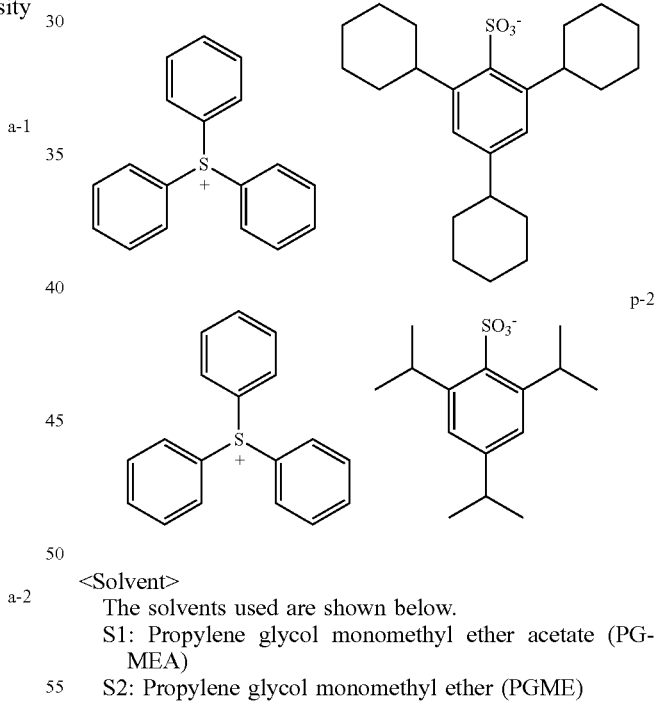

<Solvent>

The solvents used are shown below.
S1: Propylene glycol monomethyl ether acetate (PG-MEA)
S2: Propylene glycol monomethyl ether (PGME)
S3: Ethyl lactate (EL)
S4: Cyclohexanone Examples 101 to 108, and Comparative Examples 101 and 102; EB Exposure

[Preparation and Coating of Coating Liquid of Resist Composition]

The components shown in Table 1 below were dissolved in a solvent shown in Table 1 below to prepare a solution having a total concentration of solid contents of 3.0% by mass with the composition shown in Table 1 below, and this solution was filtered through a polyethylene filter having a pore size of 0.02 µm to obtain each of resist compositions R-1 to R-8 and R-x1 to R-x2.

These resist compositions were applied onto a 6-inch silicon (Si) wafer which had been previously treated with hexamethyldisilazane (HMDS) using a spin coater Mark8 manufactured by Tokyo Electron, Limited, and dried, on a hot plate at 130° C. for 300 seconds to obtain a resist film having a film thickness of 100 nm.

Here, 1 inch is 0.0254 m.

In addition, even in a case where the Si wafer is changed to a chromium substrate, the same results can be obtained.

[EB Exposure and Development]

A wafer on which the resist film obtained above had been applied was subjected to patternwise irradiation using an electron beam lithography apparatus (HL750 manufactured by Hitachi, Ltd., accelerating voltage: 50 keV). At that time, lithography was performed so that a 1:1 line-and-space was formed. After electron beam lithography, the film was heated on a hot plate at 100° C. for 60 seconds, developed for 30 seconds by puddling a 2.38%-by-mass aqueous tetramethylammonium hydroxide (TMAH) solution, and then rinsed with pure water. Thereafter, the water was rotated at a rotation speed of 4,000 rpm for 30 seconds and then heated at 95° C. for 60 seconds to obtain a resist pattern having a 1:1 line-and-space pattern with a line width of 50 nm,

[Evaluation]

(1) Resolution

The cross-sectional shape of the obtained pattern was observed with a scanning electron microscope (S-4300 manufactured by Hitachi, Ltd.). An exposure dose (electron beam irradiation dose) during resolution of a 1:1 line-and-space resist pattern with a line width of 50 nm was defined as a sensitivity (Eop), and a critical resolving power (a minimum line width with which a line and a space (line:space=1:1) were separated and resolved) at an exposure dose exhibiting the sensitivity was defined as a resolution (nm). The results are shown in Table 1.

(2) Cross-Sectional Shape of Pattern

The cross-sectional shape of a 1:1 line-and-space pattern with a line width of 50 nm at the exposure dose exhibiting the sensitivity was observed using a scanning electron microscope (S-4800 manufactured by Hitachi, Ltd.). The cross-sectional shape of the line pattern was rated as being "reversely tapered" in a case where a ratio represented by [Line width in the top part (surface part) of a line pattern/Line width in the middle of a line pattern (at the position of half the height of the line pattern)] is 1.2 or more, rated as being "slightly reversely tapered" in a case where the ratio is 1.05 or more and less than 1.2, rated as being "rectangular" in a case where the ratio is 0.95 or more and less than 1.05, and rated as being "tapered" in a case where the ratio is less than 0.95. The pattern shape is preferably "rectangular".

Moreover, in Table 1 below, the contents (% by mass) of the respective components excluding the solvents mean contents with respect to the total solid content. In addition, the content ratio (% by mass) of the solvent used with respect to all the solvents is described in Table 1 below.

Table 1 also shows a molecular weight of an acid diffusion control agent used, and a distance Ra between a Hansen solubility parameter ($HSP_1$) of the acid diffusion control agent and a Hansen solubility parameter ($HSP_2$) of air. Ra is a value calculated by the above-mentioned Expression (1), using $HSP_1$ calculated by a Y-MB method using HSPiP (4th edition 4.1.07) which is an HSP value calculation software, and $HSP_2$ (12.46, 0, 0) calculated by weighted-averaging HSP's of nitrogen and oxygen described in an HSPiP manual (ver. 4 e-Book Chapter 19).

TABLE 1

| Resist composition | Acid diffusion control agent | | | | Resin (A) | | Photoacid generator | | Solvent | | Cross-sectional shape of pattern | Resolution [nm] |
|---|---|---|---|---|---|---|---|---|---|---|---|---|
| | Type | Molecular weight | Ra | Content [% by mass] | Type | Content [% by mass] | Type | Content [% by mass] | T | Ratio [% by mass] | | |
| Example 101 R-1 | q-1 | 450.7 | 27.8 | 4 | a-1 | 76 | p-1 | 20 | S1/S2/S3 | 20/20/60 | Rectangular | 26 |
| Example 102 R-2 | q-2 | 462.5 | 18.9 | 2 | a-1 | 78 | p-1/p-2 | 10/10 | S1/S2/S3 | 20/20/60 | Rectangular | 36 |
| Example 103 R-3 | q-3 | 562.9 | 40.9 | 4 | a-1 | 76 | p-1 | 20 | S1/S2/S4 | 20/20/60 | Rectangular | 34 |
| Example 104 R-4 | q-4 | 467.7 | 26.0 | 8 | a-2 | 52 | p-1 | 40 | S1/S2/S3 | 20/20/60 | Rectangular | 30 |
| Example 105 R-5 | q-5 | 451.6 | 26.3 | 2 | a-7 | 78 | p-1 | 20 | S1/S2 | 80/20 | Rectangular | 32 |
| Example 106 R-6 | q-6 | 458.5 | 19.7 | 7 | a-3 | 63 | p-2 | 30 | S1/S2/S3 | 20/20/60 | Rectangular | 34 |
| Example 107 R-7 | q-7 | 579.9 | 39.2 | 4 | a-1 | 76 | p-1 | 20 | S1/S2/S3 | 20/20/60 | Rectangular | 32 |
| Example 108 R-8 | q-8 | 617.0 | 36.9 | 4 | a-1 | 76 | p-1 | 20 | S1/S2/S3 | 20/20/60 | Rectangular | 30 |
| Comparative Example 101 R-x1 | q-x1 | 458.5 | 14.2 | 4 | a-2 | 76 | p-1 | 20 | S1/S2/S3 | 20/20/60 | Reversely tapered | 45 |
| Comparative Example 102 R-x2 | q-x2 | 675.1 | 52.3 | 4 | a-2 | 76 | p-1 | 20 | S1/S2/S3 | 20/20/60 | — | — |

It was found that in Examples 101 to 108 using the composition of the embodiment of the present invention, the resolution was 36 nm or less and a high resolution was obtained. On the other hand, in Comparative Example 101 in which Ra was smaller than the range of the present invention, the resolution was insufficient, as compared with Examples. In Comparative Example 102 in which Ra was larger than the range of the present invention, the acid diffusion control agent was insoluble in the solvent, and thus, the resist composition could not be properly coated.

What is claimed is:

1. An actinic ray-sensitive or radiation-sensitive resin composition comprising:
   a resin having a solubility in a developer, which changes by an action of an acid;
   a compound that generates an acid upon irradiation with actinic rays or radiation; and
   an acid diffusion control agent,
   wherein a molecular weight of the acid diffusion control agent is 420 or more,
   a distance Ra between a Hansen solubility parameter of the acid diffusion control agent and a Hansen solubility parameter of air is from 15 $MPa^{0.5}$ to 45 $MPa^{0.5}$, and
   the acid diffusion control agent is a compound represented by General Formula (Q-1),

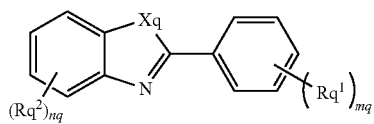

in General Formula (Q-1), $Rq^1$ and $Rq^2$ each independently represents a substituent, $Xq$ represents —NH—, —S—, or —O—, in a case where $Xq$ represents —NH—, the compound represented by General Formula (Q-1) is a compound represented by General Formula (Q11),

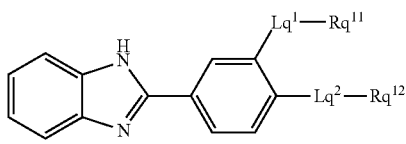

in General Formula (Q 11), $Rq^{11}$ and $Rq^{12}$ each independently represents an alkyl group or an aryl group, and $Lq^1$ and $Lq^2$ each independently represents a single bond, or —O—, —(C=O)—, an alkylene group, or a divalent linking group formed by combination of these groups, and in a case where $Xq$ represents —S— or —O—, $mq$ represents an integer of 0 to 5, in a case where $mq$ is 2 or more, a plurality of $Rq^1$'s may be the same as or different from each other, and in a case where $mq$ is 2 or more, the plurality of $Rq^1$'s may be bonded to each other to form a ring structure, and $nq$ represents an integer of 0 to 4, in a case where $nq$ is 2 or more, a plurality of $Rq^2$'s may be the same as or different from each other, and in a case where $nq$ is 2 or more, the plurality of $Rq^2$'s may be bonded to each other to form a ring structure.

2. The actinic ray-sensitive or radiation-sensitive resin composition according to claim 1, wherein Ra is from $17$ $MPa^{0.5}$ to $42$ $MPa^{0.5}$.

3. An actinic ray-sensitive or radiation-sensitive film formed of the actinic ray-sensitive or radiation-sensitive resin composition according to claim 1.

4. A pattern forming method comprising:

forming a resist film using the actinic ray-sensitive or radiation-sensitive resin composition according to claim 1;

exposing the resist film; and developing the exposed resist film using a developer.

5. A method for manufacturing an electronic device, comprising the pattern forming method according to claim 4.

* * * * *